(12) United States Patent
Jiang et al.

(10) Patent No.: US 11,708,410 B2
(45) Date of Patent: Jul. 25, 2023

(54) ANTIBODIES AND VARIANTS THEREOF AGAINST TIGIT

(71) Applicant: NANJING LEGEND BIOTECH CO., LTD., Jiangsu (CN)

(72) Inventors: Xinpo Jiang, Vancouver (CA); Shuai Yang, Jiangsu (CN); Chuan-Chu Chou, Westfield, NJ (US)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 185 days.

(21) Appl. No.: 15/733,364

(22) PCT Filed: Jan. 15, 2019

(86) PCT No.: PCT/CN2019/071711
§ 371 (c)(1),
(2) Date: Jul. 10, 2020

(87) PCT Pub. No.: WO2019/137548
PCT Pub. Date: Jul. 18, 2019

(65) Prior Publication Data
US 2021/0095028 A1    Apr. 1, 2021

(51) Int. Cl.
C07K 16/28     (2006.01)
A61P 35/00     (2006.01)
A61K 39/395    (2006.01)
A61K 45/06     (2006.01)
A61K 39/00     (2006.01)

(52) U.S. Cl.
CPC .... *C07K 16/2818* (2013.01); *A61K 39/39541* (2013.01); *A61K 45/06* (2013.01); *A61P 35/00* (2018.01); *A61K 2039/505* (2013.01); *C07K 2317/24* (2013.01); *C07K 2317/76* (2013.01); *C07K 2317/92* (2013.01)

(58) Field of Classification Search
CPC ............ C07K 16/2818; C07K 2317/24; C07K 2317/76; C07K 2317/92; A61P 35/00; A61K 39/39541; A61K 45/06; A61K 2039/505

See application file for complete search history.

(56) References Cited

U.S. PATENT DOCUMENTS 10,537,637 B2 * 1/2020 Sheng ................. A61K 38/1774
2016/0376365 A1 * 12/2016 Gurney ............ A61K 39/39558
424/133.1

FOREIGN PATENT DOCUMENTS

CN    103073644 A    5/2013
CN    107148430 A    9/2017
(Continued)

OTHER PUBLICATIONS

Kurtulos et al. TIGIT predominantly regulates the immune response via regulatory T cells. J Clin Invest. 2015;125(11):4053-4062 (Year: 2015).*

(Continued)

*Primary Examiner* — Joanne Hama
*Assistant Examiner* — Jessica Soto-Rodriguez
(74) *Attorney, Agent, or Firm* — Fish & Richardson P.C.

(57) ABSTRACT

The present application provides an antibody, such as a monoclonal antibody (mAb), or an antigen binding fragment thereof, that specifically recognizes TIGIT. Also provided are pharmaceutical compositions, or methods of making and using the antibody or antigen-binding fragment thereof.

23 Claims, 16 Drawing Sheets

Specification includes a Sequence Listing.

(56) References Cited

FOREIGN PATENT DOCUMENTS

| WO | 2016011264 | A1 | | 1/2016 | |
|---|---|---|---|---|---|
| WO | 2016028656 | A1 | | 2/2016 | |
| WO | 2016106157 | A1 | | 6/2016 | |
| WO | 2016106302 | A1 | | 6/2016 | |
| WO | 2016191643 | A2 | | 12/2016 | |
| WO | WO-2017031458 | A2 | * | 2/2017 | ....... A61K 39/39591 |
| WO | 2017053748 | A2 | | 3/2017 | |

OTHER PUBLICATIONS

Johnston et al. The Immunoreceptor TIGIT Regulates Antitumor and Antiviral CD8+ T Cell Effector Function. Cancer Cell, vol. 26, Issue 6, pp. 923-937 (Year: 2014).*

Herold et al. Determinants of teh assembkly and function of antibody variable domains. Nature Scientific Reports, 7:12276 (Year: 2017).*

Anderson et al. Lag-3, Trim-3, and TIGIT: Co-inhibitory Receptors with Specialized Functions in Immune Regulation. Immunity 44, pp. 989-1004 (Year: 2016).*

Bottino et al., "Identification of PVR (CD155) and Nectin-2 (CD112) as Cell Surface Ligands for the Human DNAM-1 (CD226) Activating Molecule", J. Exp. Med., vol. 198, No. 4, Aug. 18, 2003, pp. 557-567.

Joller et al., "Cutting Edge: TIGIT Has T Cell-Intrinsic Inhibitory Functions", J Immunol 2011; 186(3):1338-1342.

Li et al., "T-cell Immunoglobulin and ITIM Domain (TIGIT) Receptor/ Poliovirus Receptor (PVR) Ligand Engagement Suppresses Interferon-γ Production of Natural Killer Cells via B-Arrestin 2-mediated Negative Signaling", The Journal of Biological Chemistry, vol. 289, No. 25, pp. 17647-17657, Jun. 20, 2014.

Pende et al., "Expression of the DNAM-1 ligands, Nectin-2 (CD112) and poliovirus receptor (CD155), on dendritic cells: relevance for natural killer-dendritic cell interaction", Blood, Mar. 1, 2006, vol. 107, No. 5, pp. 2030-2036.

Reymond et al., "DNAM-1 and PVR Regulate Monocyte Migration through Endothelial Junctions", J. Exp. Med., vol. 199, No. 10, May 17, 2004, pp. 1331-1341.

Stengel et al., "Structure of TIGIT immunoreceptor bound to poliovirus receptor reveals a cell-cell adhesion and signaling mechanism that requires cis-trans receptor clustering", PNAS, Apr. 3, 2012, vol. 109, No. 14, 5399-5404.

Tahara-Hanaoka et al., "Functional characterization of DNAM-1 (CD226) interaction with its ligands PVR (CD155) and nectin-2 (PRR-2/CD112)", International Immunology, vol. 16, No. 4, pp. 533-538, 2004.

Yu et al., "The surface protein TIGIT suppresses T cell activation by promoting the generation of mature immunoregulatory dendritic cells", vol. 10, No. 1, pp. 48-57, Jan. 2009, Nature Immunology.

Zhu et al., "Identification of CD112R as a novel checkpoint for human T cells", JEM, 2016, vol. 213, No. 2, pp. 167-176.

Blake S J., et al., "Molecular Pathways: Targeting CD96 and TIGIT for Cancer Immunotherapy", Clinical Cancer Research, Nov. 1, 2016, American Association for Cancer Research, US, vol. 22, Nr: 21, pp. 5183-5188.

International Search Report for App. No. PCT/CN2019/071711, dated Apr. 17, 2019, 7 pages.

* cited by examiner

US 11,708,410 B2

ANTIBODIES AND VARIANTS THEREOF AGAINST TIGIT

CROSS REFERENCE TO RELATED APPLICATIONS

This application is a Section 371 of International Application No. PCT/CN2019/071711, filed on Jan. 15, 2019, which published in the English language on Jul. 18, 2019 under International Publication No. WO 2019/137548 A1, which claims priority to International Patent Application No. PCT/CN2018/072607, filed on Jan. 15, 2018, the contents of which are incorporated herein by reference in their entirely.

SUBMISSION OF SEQUENCE LISTING ON ASCII TEXT FILE

This application contains a sequence listing, which is submitted electronically via EFS-Web as an ASCII formatted sequence listing with a file name "065782 6US1 Sequence Listing" and a creation date of Jun. 5, 2020, and having a size of 61 kb. The sequence listing submitted via EFS-Web is part of the specification and is herein incorporated by reference in its entirety.

FIELD OF THE INVENTION

The application relates to antibodies or antigen binding fragments thereof capable of binding specifically to a TIGIT protein and uses of such agents. In some embodiments, the application relates to mouse and humanized monoclonal antibodies directed to TIGIT and uses of these antibodies. The antibodies or antigen binding fragments thereof are useful as diagnostics and for the treatment of diseases associated with the activity and/or expression of TIGIT.

BACKGROUND OF THE INVENTION

The immune system is a host defense system comprising a collection of cells, tissues, and organs that work together to protect against attacks by "foreign" invaders or abnormal cells arose by mutation. The invaders are primarily infection-causing organisms such as bacteria, viruses, parasites, and fungi. The capacity of the immune system to detect and destroy abnormal cells prevents the development of many cancers and helps to fight cancers. The immune system comprised of the central immune organs and the peripheral immune organs work together as one unit to fight infectious disease. The capability to fend off millions of structurally different foreign enemies shows the complexity of the immune system. This complexity is fulfilled by a dynamic communication network of organs, tissues, cells, and molecules. These organs, tissues, cells, and molecules cooperate with each other and keep the immune system in balance to fight foreign invasion and maintain self-tolerance at the same time.

Immune checkpoint proteins play an important role in regulating the immune response to maintain self-tolerance and to fight invaders. They are molecules that either trigger or block an immune response. The stimulatory immune checkpoint proteins promote immunity while the inhibitory immune checkpoint proteins put a brake on immune activity and prevent autoimmunity. The inhibitory immune checkpoint proteins, such as PD-1, and CTLA-4, expressed on T cells act as the brakes to suppress the immune responses. Blocking the inhibitory immune checkpoint proteins activates T cells.

Human tumors are the consequence of combination of genetic and epigenetic changes. When tumor cells form, some of the antigens on their surface may change. These so-called neo-antigens would be detected by the immune system and are to be destroyed as foreign objects. The abnormal cells are eliminated before they progress to advanced cancer stage. However, tumor cells develop multiple resistance mechanisms to evade and suppress the immune system. A common mechanism applied by tumors is to manipulate immune checkpoint pathways by overexpressing the inhibitory immune checkpoint modulators. Cancer immunotherapy exploits the host's immune system to treat cancer. The mechanisms ranging from activating effector cells to blocking inhibitory factors boosts the immune system and produces antitumor activities. Drugs blocking inhibitory immune checkpoint pathways have demonstrated promising clinical activities in various solid tumors.

PD-1 and CTLA-4 are two inhibitory immune checkpoint proteins widely studied. Monoclonal antibodies directed against PD-1 or CTLA-4 have revolutionized the management of patients with advanced-stage melanoma and have emerged as a successful cancer treatment for many other cancers. Moreover, not only has the blockade of PD-1 or CTLA-4 demonstrated tumor regression responses in cancer patients, but blockage of other inhibitory immune checkpoint proteins, such as TIM-3, LAG-3, or VISTA also has shown effective anti-tumor responses in many pre-clinical studies. These results underscore the importance to identify antibodies against the new inhibitory immune checkpoint proteins for effective cancer immunotherapy.

T-Cell Immunoreceptor with Ig and ITIM Domains (TIGIT) is an immune checkpoint protein expressed on both T cells and natural killer (NK) cells. TIGIT contains immunoglobulin (Ig) and immunoreceptor tyrosine-based inhibitory motif (ITIM) domains and functions as an inhibitory immune checkpoint protein to target both the adaptive and innate immune systems. ITIMs have been expressed in a large number of inhibitory receptors that negatively regulate immune cell activities. These receptors includes immunoglobulin (Ig) superfamily members, sialic acid binding lectin-like molecules (Siglecs), and C-type lectin receptors. When ITIM-containing receptors interact with their ligand, ITIMs are phosphorylated by Src-family tyrosine kinases. The phosphorylated ITIMs provide docking sites for Src homology 2 domain-containing phosphatases, including SHIP-1, Shp1, and Shp2. These phosphatases are able to dephosphorylate and inactivate the immunoreceptor tyrosine-based activation motif (ITAM)-containing receptors. Through this mechanism, ITIM-containing receptors inhibit signaling from ITAM-containing receptors in the immune system and keep the activation of immune system in check. TIGIT is expressed by activated cytotoxic T cells and regulatory T cells and might act as a key inhibitory immune checkpoint modulator to "turn off" the immune response.

CD28 and CTLA-4 have the opposite effects when they interact with their ligands, B7-1 or B7-2. The binding of B7-1 or B7-2 to CD28 has a stimulatory effect on the immune system and the binding of B7-1 or B7-2 to CTLA-4 has an inhibitory effect. CD226 and TIGIT are the reminiscent pair of CD28 and CTLA-4. The ligands for CD226 and TIGIT are CD112 and CD155 (also known as PVR). The activating CD226 and deactivating TIGIT compete for the same ligands, which can result in a delicate balance to switch on or switch off T cells.

Cancer immunotherapy is a treatment through boosting a patient's immune system to fight cancer. Blocking any inhibitory immune checkpoint modulator will tip the balance towards the activation state in the immune system. It is one of the tools in cancer immunotherapy. TIGIT is a promising new target of inhibitory immune checkpoint modulator. Developing an antagonist antibody specifically against TIGIT will block its inhibitory effect on T cells and increase immunity to fight cancer.

BRIEF SUMMARY OF THE INVENTION

The present application relates to targeted binding agents against a TIGIT protein, and methods of making and using thereof.

In a general aspect, the application relates to an isolated antibody or antigen-binding fragment thereof, comprising:
(a) a heavy chain variable domain (VH) comprising:
 i. a heavy chain complementarity determining region 1 (CDR1) comprising an amino acid sequence selected from the group consisting of SEQ ID NOs:27-39;
 ii. a heavy chain CDR2 comprising an amino acid sequence selected from the group consisting of SEQ ID NOs:40-52; and
 iii. a heavy chain CDR3 comprising an amino acid sequence selected from the group consisting of SEQ ID NOs:53-65; and
(b) a light chain variable domain (VL) comprising:
 i. a light chain CDR1 comprising an amino acid sequence selected from the group consisting of SEQ ID NOs: 66-78;
 ii. a light chain CDR2 comprising an amino acid sequence selected from the group consisting of SEQ ID NOs: 79-91; and
 iii. a light chain CDR3 comprising an amino acid sequence selected from the group consisting of SEQ ID NOs:92-104;
 wherein the antibody or antigen-binding fragment thereof is capable of specifically binding to TIGIT, preferably a human TIGIT.

The invention provides a mouse monoclonal antibody (70A11A8E6) or an antigen binding fragment that specifically binds to human TIGIT and comprise heavy chain variable regions, CDR1, CDR2, and CDR3 sequences comprising amino acid sequences of SEQ ID NOs: 27, 40, and 53, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 66, 79, and 92, respectively. In one embodiment, the anti-human TIGIT mouse monoclonal antibody of the present invention comprises the heavy chain and light chain variable domains of 70A11A8E6 comprising amino acid sequences of SEQ ID NOs: 1 and 14. It covers the sequences sharing at least 80%, 85%, 90% and 95% sequence identity with these disclosed sequence. In another embodiment, the mouse monoclonal antibody, 70A11A8E6, or an antigen binding fragment comprise the following functional characteristics: (a) binds to human TIGIT with a $K_D$ of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (11D8E12A4) or an antigen binding fragment that specifically binds to human TIGIT and comprise heavy chain variable regions, CDR1, CDR2, and CDR3 sequences comprising amino acid sequences of SEQ ID NOs: 28, 41, and 54, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 67, 80, and 93, respectively. In one embodiment, the anti-human TIGIT mouse monoclonal antibody of the present invention comprises the heavy chain and light chain variable domains of 11D8E12A4 comprising amino acid sequences of SEQ ID NOs: 2 and 15. It covers the sequences sharing at least 80%, 85%, 90% and 95% sequence identity with these disclosed sequence. In another embodiment, the mouse monoclonal antibody, 11D8E12A4, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (16F10H12C11) or an antigen binding fragment that specifically binds to human TIGIT and comprise heavy chain variable regions, CDR1, CDR2, and CDR3 sequences comprising amino acid sequences of SEQ ID NOs: 29, 42, and 55, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 68, 81, and 94, respectively. In one embodiment, the anti-human TIGIT mouse monoclonal antibody of the present invention comprises the heavy chain and light chain variable domains of 16F10H12C11 comprising amino acid sequences of SEQ ID NOs: 3 and 16. It covers the sequences sharing at least 80%, 85%, 90% and 95% sequence identity with these disclosed sequence. In another embodiment, the mouse monoclonal antibody, 16F10H12C11, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (8F2D8E7) or an antigen binding fragment that specifically binds to human TIGIT and comprise heavy chain variable regions, CDR1, CDR2, and CDR3 sequences comprising amino acid sequences of SEQ ID NOs: 30, 43, and 56, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 69, 82, and 95, respectively. In one embodiment, the anti-human TIGIT mouse monoclonal antibody of the present invention comprises the heavy chain and light chain variable domains of 8F2D8E7 comprising amino acid sequences of SEQ ID NOs: 4 and 17. It covers the sequences sharing at least 80%, 85%, 90% and 95% sequence identity with these disclosed sequence. In another embodiment, the mouse monoclonal antibody, 8F2D8E7, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (48B5G4E12) or an antigen binding fragment that specifically binds to human TIGIT and comprise heavy chain variable regions, CDR1, CDR2, and CDR3 sequences comprising amino acid sequences of SEQ ID NOs: 31, 44, and 57, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 70, 83, and 96, respectively. In one embodiment, the anti-human TIGIT mouse monoclonal antibody of the present invention comprises the heavy chain and light chain variable domains of 48B5G4E12 comprising amino acid sequences of SEQ ID NOs: 5 and 18. It covers the sequences sharing at least 80%, 85%, 90% and 95% sequence identity with these disclosed sequence. In another embodiment, the mouse monoclonal antibody, 48B5G4E12, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (139E2C2D2) or an antigen binding fragment that specifically binds to human TIGIT and comprise heavy chain variable regions, CDR1, CDR2, and CDR3 sequences comprising amino acid sequences of SEQ ID NOs: 32, 45, and 58, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 71, 84, and 97, respectively. In one embodiment, the anti-human TIGIT mouse monoclonal antibody of the present invention comprises the heavy chain and light chain variable domains of 139E2C2D2 comprising amino acid sequences of SEQ ID NOs: 6 and 19. It covers the sequences sharing at least 80%, 85%, 90% and 95% sequence identity with these disclosed sequence. In another embodiment, the mouse monoclonal antibody, 139E2C2D2, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (128E3G7F5) or an antigen binding fragment that specifically binds to human TIGIT and comprise heavy chain variable regions, CDR1, CDR2, and CDR3 sequences comprising amino acid sequences of SEQ ID NOs: 33, 46, and 59, respectively. They also comprise light chain variable regions, CDR1, CDR2, and CDR3 sequences comprising amino acid sequences of SEQ ID NOs: 72, 85, and 98, respectively. In one embodiment, the anti-human TIGIT mouse monoclonal antibody of the present invention comprises the heavy chain and light chain variable domains of 128E3G7F5 comprising amino acid sequences of SEQ ID NOs: 7 and 20. It covers the sequences sharing at least 80%, 85%, 90% and 95% sequence identity with these disclosed sequence. In another embodiment, the mouse monoclonal antibody, 128E3G7F5, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (121C2F10B5) or an antigen binding fragment that specifically binds to human TIGIT and comprise heavy chain variable regions, CDR1, CDR2, and CDR3 sequences comprising amino acid sequences of SEQ ID NOs: 34, 47, and 60, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 73, 86, and 99, respectively. In one embodiment, the anti-human TIGIT mouse monoclonal antibody of the present invention comprises the heavy chain and light chain variable domains of 121C2F10B5 comprising amino acid sequences of SEQ ID NOs: 8 and 21. It covers the sequences sharing at least 80%, 85%, 90% and 95% sequence identity with these disclosed sequence. In another embodiment, the mouse monoclonal antibody, 121C2F10B5, or an antigen binding fragment comprise the following functional characteristics: (a) binds to human TIGIT with a $K_D$ of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (104G12E12G2) or an antigen binding fragment that specifically binds to human TIGIT and comprise heavy chain variable regions, CDR1, CDR2, and CDR3 sequences comprising amino acid sequences of SEQ ID NOs: 35, 48, and 61, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 74, 87, and 100, respectively. In one embodiment, the anti-human TIGIT mouse monoclonal antibody of the present invention comprises the heavy chain and light chain variable domains of 104G12E12G2 comprising amino acid sequences of SEQ ID NOs: 9 and 22. It covers the sequences sharing at least 80%, 85%, 90% and 95% sequence identity with these disclosed sequence. In another embodiment, the mouse monoclonal antibody, 104G12E12G2, or an antigen binding fragment comprise the following functional characteristics: (a) binds to human TIGIT with a $K_D$ of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (83G6H11C12) or an antigen binding fragment that specifically binds to human TIGIT and comprise heavy chain variable regions, CDR1, CDR2, and CDR3 sequences comprising amino acid sequences of SEQ ID NOs: 36, 49, and 62, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 75, 88, and 101, respectively. In one embodiment, the anti-human TIGIT mouse monoclonal antibody of the present invention comprises the heavy chain and light chain variable domains of 83G6H11C12 comprising amino acid sequences of SEQ ID NOs: 10 and 23. It covers the sequences sharing at least 80%, 85%, 90% and 95% sequence identity with these disclosed sequence. In another embodiment, the mouse monoclonal antibody, 83G6H11C12, or an antigen binding fragment comprise the following functional characteristics: (a) binds to human TIGIT with a $K_D$ of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (92E9D4B4) or an antigen binding fragment that specifically binds to human TIGIT and comprise heavy chain variable regions, CDR1, CDR2, and CDR3 sequences comprising amino acid sequences of SEQ ID NOs: 37, 50, and 63, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 76, 89, and 102, respectively. In one embodiment, the anti-human TIGIT mouse monoclonal antibody of the present invention comprises the heavy chain and light chain variable domains of 92E9D4B4 comprising amino acid sequences of SEQ ID NOs: 11 and 24. It covers the sequences sharing at least 80%, 85%, 90% and 95% sequence identity with these disclosed sequence. In another embodiment, the mouse monoclonal antibody, 92E9D4B4, or an antigen binding fragment comprise the following functional characteristics: (a) binds to human TIGIT with a $K_D$ of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (100C4E7D11 also referred to herein as "100C4") or an antigen binding fragment that specifically binds to human TIGIT and comprise heavy chain variable regions, CDR1, CDR2, and CDR3 sequences comprising amino acid sequences of SEQ ID NOs: 38, 51, and 64, respectively. The mouse monoclonal antibody or antigen binding fragment that specifically binds to human TIGIT can also comprise light chain variable regions, CDR1, CDR2, and CDR3 sequences comprising amino acid sequences of SEQ ID NOs: 77, 90, and 103, respectively. In one embodiment, the anti-human TIGIT mouse monoclonal antibody of the present invention comprises the heavy chain and light chain variable domains of 100C4E7D11 comprising amino acid sequences of SEQ ID NOs: 12 and 25. The humanized VH sequences of SEQ ID NOs: 105-108 have the CDRs of SEQ ID Nos: 38, 51, and 64 and the humanized VL sequences of SEQ ID NOs: 113-117 have the CDRs of SEQ ID NOs: 77, 90, and 103. It covers the sequences sharing at least 80%, 85%, 90% and 95% sequence identity with these disclosed sequence. In another embodiment, the mouse monoclonal antibody 100C4E7D11, the antibodies made by the combinations of one of the VH sequences of SEQ ID NOs:12, and 105-108 and one of the VL sequences of SEQ ID NOs:25, and 113-117, or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

The invention provides a mouse monoclonal antibody (64G1E9B4, also referred to herein as "64G1") or an antigen binding fragment that specifically binds to human TIGIT and comprise heavy chain variable regions, CDR1, CDR2, and CDR3 sequences comprising amino acid sequences of SEQ ID NOs: 39, 52, and 65, respectively. They also comprise light chain variable regions, CDR1, CDR2, and CDR3 sequences comprising amino acid sequences of SEQ ID NOs: 78, 91, and 104, respectively. In one embodiment, the anti-human TIGIT mouse monoclonal antibody of the present invention comprises the heavy chain and light chain variable domains of 64G1E9B4 comprising amino acid sequences of SEQ ID NOs: 13 and 26. In one embodiment, the antibody comprises one amino acid substitution in the heavy chain CDR of SEQ ID NO: 52, wherein the substitution is made at position 7D, and wherein residue 7D is substituted to G (SEQ ID NO: 128). In one embodiment, the antibody comprises one amino acid substitution in the heavy chain CDR of SEQ ID NO: 65, wherein the substitution is made at position 8M, and wherein residue 8M is substituted to F or L (SEQ ID NO: 129 or 130, respectively). In one embodiment, the antibody comprises one amino acid substitution in the light chain CDR of SEQ ID NO: 78, wherein the substitution is made at position 1K, and wherein residue 1K is substituted to R (SEQ ID NO: 131). The humanized VH sequences of SEQ ID NOs: 109-112 have the CDRs of SEQ ID NOs: 39, 52, and 65 and the humanized VL sequence of SEQ ID NO: 118 has the CDRs of SEQ ID NOs: 78, 91, and 104. In some embodiments, the CDR substitutions described above can be made in the corresponding CDRs of the VH sequences of SEQ ID NOs:109-112, and the CDR substitutions described above can be made in the corresponding CDRs of the VL sequences of SEQ ID NO:118. It covers the sequences sharing at least 80%, 85%, 90% and 95% sequence identity with these disclosed sequence. In another embodiment, the mouse monoclonal antibody 64G1E9B4, the antibodies made by the combinations of one of the VH sequences of SEQ ID NOs:13, 109-112, or of SEQ ID NOs:109-112 substituted its corresponding CDRs with CDR substitutions mentioned above (e.g., SEQ ID NOs: 132 or 134) and one of the VL sequences of SEQ ID NOs:26, 118, or of SEQ ID NO:118 substituted its corresponding CDRs with CDR substitutions mentioned above (e.g., SEQ ID NO: 133 or 135), or an antigen binding fragment comprise the following functional characteristics: (a) binds to human TIGIT with a KD of 20 nM or less as determined by surface plasmon resonance (BIAcore); (b) has cross-reactivity to cynomolgous TIGIT; (c) block the interaction between human TIGIT and its ligand, CD155; (d) activate T cell in a reporter assay; (e) stimulate IL-2 production in Jurkat cells.

An antibody or antigen-binding fragment thereof of the application can be rodent, chimeric, human, partially humanized, or fully humanized. It can also be bispecific further comprising a second antibody moiety capable of specifically binding to a second antigen, such as CTLA-4, PD-L1, TIM-3 or LAG-3. Preferably, the second antibody moiety is a single domain antibody (sdAb).

Further provided is a pharmaceutical composition comprising any one of the isolated anti-TIGIT antibodies or antigen binding fragments thereof of the application, and a pharmaceutical acceptable carrier.

Another aspect of the application provides a method of treating an individual having a TIGIT-related disease, comprising administering to the individual an effective amount of any one of the pharmaceutical composition described above. In some embodiments, the TIGIT related disease is cancer. In some embodiments, the cancer is a solid tumor, such as a colon cancer. In some embodiments, the method further comprises administering to the individual an additional cancer therapy, such as a surgery, radiation, chemotherapy, immunotherapy, hormone therapy, or a combination thereof. In some embodiments, the TIGIT related disease is a pathogenic infection. In some embodiments, the pharmaceutical composition is administered systemically, such as intravenously (i.v.). In some embodiments, the pharmaceutical composition is administered locally, such as intratumorally. In some embodiments, the individual is a human.

Other aspects, features and advantages of the invention will be apparent from the following disclosure, including the detailed description of the invention and its preferred embodiments and the appended claims.

BRIEF DESCRIPTION OF THE DRAWINGS

FIG. 1B: mouse #8100; FIG. 1C: mouse #8771). The test bleed was screened by a FACS study on CHO cells over-expressed with human TIGIT. The mouse with high TIGIT binding signal indicated higher titer and was selected for the final boost before cell fusion.

FIG. 2B: 16F10H12C11; FIG. 2C: 11D8E12A4; FIG. 2D: 48B5G4E12; FIG. 2E: 70A11A8E6; FIG. 2F: 139E2C2D2; FIG. 2G: 104G12E12G2; FIG. 2H: 64G1E9B4; FIG. 2I: 83G6H11C12; FIG. 2J: 92E9D4B4; FIG. 2K: 100C4E7D11; FIG. 2L: 128E3G7F5; and FIG. 2M: 121C2F10B5). The supernatants collected from hybridoma subclones were screened by a FACS study on CHO cells over-expressed with human TIGIT. The subclones with the high TIGIT binding signals were selected for the purifications.

DETAILED DESCRIPTION OF THE INVENTION

Figure 1A:
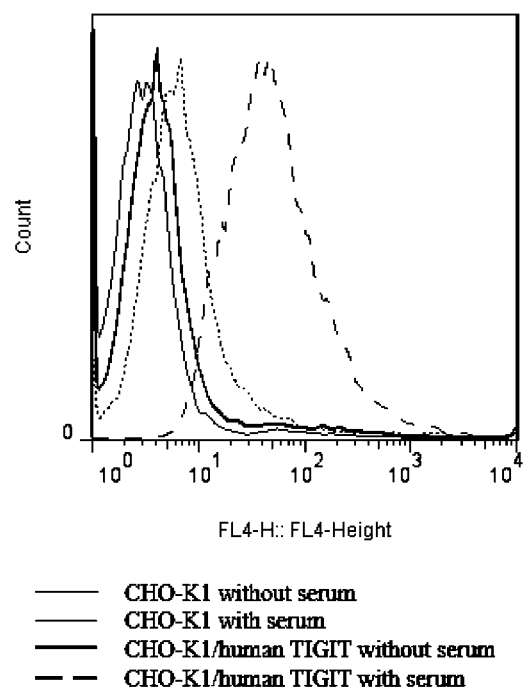
FIGS. 1A-1C depict serum antibody titer tests by fluorescence-activated cell sorting (FACS) on CHO cells overexpressed with human TIGIT. The serum was collected from each immunized mouse for the titer test (FIG. 1A: mouse #8087.

The present application provides the anti-human TIGIT monoclonal antibodies and their application. The disclosure pertains to the gene sequences of the stated heavy chain variable domains ($V_H$) and the light chain variable domains ($V_L$) of the mouse anti-human TIGIT monoclonal antibodies clones, 70A11A8E6, 11D8E12A4, 16F10H12C11, 8F2D8E7, 48B5G4E12, 139E2C2D2, 128E3G7F5, 121C2F10B5, 104G12E12G2, 83G6H11C12, 92E9D4B4, 100C4E7D11, and 64G1E9B4. It also pertains to the gene sequences of the stated heavy chain variable domains ($V_H$) and the light chain variable domains ($V_L$) after the humanization or post-translational modification on some of these mouse anti-human TIGIT monoclonal antibodies clones. The disclosure pertains to methods of the generation of the anti-human TIGIT monoclonal antibodies.

The present application provides the chimeric anti-human TIGIT monoclonal antibodies by fusing variable domains of the heavy and light chains of the disclosed clones with the constant region of human IgG1. The present application provides the humanized forms of the heavy chain variable domains ($V_H$) and the light chain variable domains ($V_L$) of the mouse anti-human TIGIT monoclonal antibodies clones. The humanized anti-human TIGIT monoclonal antibodies were generated by fusing the humanized variable domains of the heavy and light chains of the disclosed clones with the constant region of human IgG1.

I. Definitions

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al, Short Protocols in Molecular Biology, 3rd ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes 10% of the recited value. For example, a concentration of 1 mg/mL includes 0.9 mg/mL to 1.1 mg/mL. Likewise, a concentration range of 1 mg/mL to 10 mg/mL includes 0.9 mg/mL to 11 mg/mL. As used herein, the use of a numerical range expressly includes all possible subranges, all individual numerical values within that range, including integers within such ranges and fractions of the values unless the context clearly indicates otherwise.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the invention contemplate any one or more of these aspects of treatment.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition can: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "antibody," "antibody moiety" or "antibody construct" is used in the broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for and F isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs" (Variable domain of the heavy chain of the Heavy chain antibody). Some $V_H$Hs can also be known as nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and can include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain can be referred to as "$V_H$" and "VL", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H$H". $V_H$H is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, deamidations) that can be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the application can be made by a variety of techniques, including, for example, the hybridoma method (e.g., Kohler and Milstein., Nature, 256:495-97 (1975); Hongo et al., Hybridoma, 14 (3): 253-260 (1995), Harlow et al., Antibodies: A Laboratory Manual, (Cold Spring Harbor Laboratory Press, 2″ ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Nat'l. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Nat'l. Acad. Sci. USA 90: 2551(1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994);

Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The terms "full-length antibody," "intact antibody," or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_H H$) and an Fc region. The constant domains can be native sequence constant domains (e.g., human native sequence constant domains) or amino acid sequence variants thereof. In some cases, the intact antibody can have one or more effector functions.

An "antibody fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; linear antibodies (see U.S. Pat. No. 5,641,870, Example 2; Zapata et al., *Protein Eng.* 8(10): 1057-1062); single-chain antibody molecules; single-domain antibodies (such as $V_H H$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

The term "constant domain" refers to the portion of an immunoglobulin molecule having a more conserved amino acid sequence relative to the other portion of the immunoglobulin, the variable domain, which contains the antigen-binding site. The constant domain contains the $C_H 1$, $C_H 2$ and $C_H 3$ domains (collectively, CH) of the heavy chain and the CHL (or CL) domain of the light chain.

The "light chains" of antibodies (immunoglobulins) from any mammalian species can be assigned to one of two clearly distinct types, called kappa ("κ") and lambda (" "), based on the amino acid sequences of their constant domains.

"Fv" is the minimum antibody fragment which contains a complete antigen-recognition and—binding site. This fragment consists of a dimer of one heavy—and one light—chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l. Acad. Sci. USA*, 81:6851-6855 (1984)). "Humanized antibody" is used as a subset of "chimeric antibodies".

"Humanized" forms of non-human (e.g., llama or camelid) antibodies are antibodies that contain minimal sequence derived from non-human immunoglobulin. In some embodiments, a humanized antibody is a human immunoglobulin (recipient antibody) in which residues from an CDR (hereinafter defined) of the recipient are replaced by residues from an CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies can comprise residues that are not found in the recipient antibody or in the donor antibody. These modifications can be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions can include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, Biochem. Soc. *Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest*, 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

| | | HVR delineations. | | |
|---|---|---|---|---|
| Loop | Kabat | AbM | Chothia | Contact |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs can comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The amino acid residues of a single-domain antibody (such as $V_HH$) are numbered according to the general numbering for VH domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, *J. Immunol. Methods* 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDRs can vary and cannot correspond to the total number of amino acid residues indicated by the Kabat numbering (that is, one or more positions according to the Kabat numbering cannot be occupied in the actual sequence, or the actual sequence can contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence can contain fewer or additional amino acids corresponding to a shortening of, or insertion into, a FR or HVR of the variable domain. For example, a heavy-chain variable domain can include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues can be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the $V_L$, the subgroup can be subgroup kappa I, kappa II, kappa III or kappa IV as in Kabat et al., supra. Additionally, for the VH, the subgroup can be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework can comprise the same amino acid sequence thereof, or it can contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *BiolTechnology* 10:779-783 (1992) describes affinity maturation by $V_H$- and $V_L$-domain shuffling. Random mutagenesis of CDR and/or framework residues is described by, for example: Barbas et al. *Proc Nat'l. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

As use herein, the term "specifically binds," "specifically recognizes," or is "specific for" refers to measurable and reproducible interactions such as binding between a target and an antigen binding protein (such as a mAb), which is determinative of the presence of the target in the presence of a heterogeneous population of molecules including biological molecules. For example, an antigen binding protein (such as a mAb) that specifically binds a target (which can be an epitope) is an antigen binding protein (such as a mAb) that binds this target with greater affinity, avidity, more readily, and/or with greater duration than it binds other targets. In some embodiments, the extent of binding of an antigen binding protein (such as a mAb) to an unrelated target is less than about 10% of the binding of the antigen binding protein (such as a mAb) to the target as measured, e.g., by a radioimmunoassay (RIA). In some embodiments, an antigen binding protein (such as a mAb) that specifically binds a target has a dissociation constant ($K_D$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antigen binding protein specifically binds an epitope on a protein that is conserved among the protein from different species. In some embodiments, specific binding can include, but does not require, exclusive binding.

The term "specificity" refers to selective recognition of an antigen binding protein (such as a mAb) for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. That is, for example, the terms "anti-TIGIT/PD-L1," "anti-PD-L1/TIGIT," "TIGITxPD-L1," "PD-L1xTIGIT," "PD-L1-TIGIT," and "TIGIT-PD-L1" can be used interchangeably to refer to bispecific antibodies that specifically bind to both TIGIT and PD-L1. The term "monospecific" as used herein denotes an antigen binding protein (such as a mAb) that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent," "tetravalent," "pentavalent," and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation comprises an N297A or DANA mutation (D265A and/or N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and natural killer (NK) cells. Alternatively, or additionally, ADCC activity of the molecule of interest can be assessed in vivo, e.g., in an animal model such as that disclosed in Clynes et al., *Proc. Nat'l. Acad. Sci. USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region can be removed, for example, during production or purification of the antibody, or by recombinantly engineering the nucleic acid encoding a heavy chain of the antibody. Accordingly, a composition of intact antibodies can comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), can be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_D$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1} s^{1}$. The term equilibrium dissociation constant "$K_D$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of $K_D$ presupposes that all binding agents are in solution. In the case where the antibody is tethered to a cell wall, e.g., in a yeast expression system, the corresponding equilibrium rate constant is expressed as $EC_{50}$, which gives a good approximation of $K_D$. The affinity constant, $K_a$, is the inverse of the dissociation constant, $K_D$, expressed in units of $M^1$.

The dissociation constant ($K_D$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (moles per liter). An antibody or antigen-binding fragment thereof that specifically binds to a target can have a dissociation constant ($K_D$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M or $\leq 10^{-12}$ M.

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between PD-L1 and B7-1, or component of a process, i.e. an enzyme, cell, cell receptor or microorganism) by half. The values are typically expressed as molar concentration. $IC_{50}$ is comparable to an $EC_{50}$ for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody (such as an anti-PD-L1 mAb) needed to neutralize 50% of the antigen bioactivity (such as PD-L1 bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny cannot be completely identical in nucleic acid content to a parent cell, but can contain mutations. Mutant progeny that have the same function or biological activity as screened or selected for in the originally transformed cell are included herein.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X."

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

II. Anti-TIGIT Construct

Anti-TIGIT Monoclonal Antibody

An isolated anti-TIGIT construct described herein comprises a monoclonal antibody (mAb) moiety that specifically recognizes or binds to TIGIT (or "anti-TIGIT mAb"). In some embodiments of the invention, an isolated anti-TIGIT construct is a full-length IgG. TIGIT Similar in structure to the larger PVR-nectin family of molecules, TIGIT protein contains an extracellular IgV domain, a type 1 transmembrane region, and a cytoplasmic tail containing an ITIM and an immunoglobulin tail tyrosine (ITT)-like motif Engagement of TIGIT through CD155 induces phosphorylation of TIGIT through Fyn and Lck and the recruitment of SHIP1 through the cytosolic adaptor Grb2. Recruitment of SHIP1 to the TIGIT tail blocks signal transduction through the PI3K and MAPK pathways and results in NK cell inhibition. Additionally, upon phosphorylation, the ITT-like motif of TIGIT binds β-arrestin 2 and recruits SHIP1 to limit NF-κB signaling. An exemplary amino acid sequence of human TIGIT is disclosed at Genbank Accession Number NP_776160.2.

According to embodiments of the invention, a human TIGIT sequence is at least 90% identical in amino acids sequence to human TIGIT of Genbank Accession Number NP_776160.2 and contains amino acid residues that identify the amino acid sequence as being human when compared to TIGIT amino acid sequences of other species (e.g., murine). In some embodiments, a human TIGIT can be at least about 95%, 96%, 97%, 98%, or 99% identical in amino acid sequence to TIGIT of Genbank Accession Number NP_776160.2. In some embodiments, a human TIGIT sequence will display no more than 10 amino acid differences from the TIGIT of Genbank Accession Number NP_776160.2. In some embodiments, a human TIGIT can display no more than 5, 4, 3, 2, or 1 amino acid difference from the TIGIT of Genbank Accession Number NP_776160.2. Percent identity can be determined as described herein. In some embodiments, an anti-TIGIT mAb described herein specifically binds to a TIGIT polypeptide with 100% amino acid sequence identity to the TIGIT of Genbank Accession Number NP_776160.2. In some embodiments, an anti-TIGIT mAb of the application specifically binds to a TIGIT polypeptide comprising the amino acid sequence of SEQ ID NO: 122.

In some embodiments, an anti-TIGIT mAb of the application can cross-react with TIGIT from species other than human, or other proteins which are structurally related to human TIGIT (e.g., human TIGIT homologs). In some embodiments, an anti-TIGIT mAb of the application is completely specific for human TIGIT and not exhibit species or other types of cross-reactivity.

Antibody Affinity

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

In some embodiments, the $K_D$ of the binding between the anti-TIGIT mAb and TIGIT is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-5}$ M to about $10^{-12}$ M, about $10^{-6}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-5}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-7}$ M to about $10^{-10}$ M, about $10^{-8}$ M to about $10^{-10}$ M, about $10^{-5}$ M to about $10^{-9}$ M, about $10^{-7}$ M to about $10^{-9}$ M, about $10^{-5}$ M to about $10^{-8}$ M, or about $10^{-6}$ M to about $10^{-8}$ M.

In some embodiments, the $K_{on}$ of the binding between the anti-TIGIT mAb and TIGIT is about $102$ $M^{-1}s^{-1}$ to about $10^{-4}$ $M^{-1}s^{-1}$, about $10^{-4}$ $M^{-1}s^{-1}$ to about $10^{-6}$ $M^{-1}s^{-1}$, about $106$ $M^{-1}s^{-1}$ to about $10^{-7}$ $M^{-1}s^{-1}$, about $10^{-2}$ $M^{-1}s^{-1}$ to about $10^{-7}$ $M^{-1}s^{-1}$, about $10^{-3}$ $M^{1}s^{-1}$ to about $10^{-7}$ $M^{-1}s^{-1}$, about $10^{-4}$ $M^{-1}s^{-1}$ to about $10^{-7}$ $M^{-1}s^{-1}$, about $10^{-5}$ $M^{-1}s^{-1}$ to about $10^{-7}$ $M^{-1}s^{-1}$, about $10^{-3}$ $M^{-1}s^{-1}$ to about $10^{-6}$ $M^{-1}s^{-1}$, or about $10^{-4}$ $M^{-1}s^{-1}$ to about $106$ $M^{-1}s^{-1}$.

In some embodiments, the $K_{off}$ of the binding between the anti-TIGIT mAb and TIGIT is about $1$ $s^{-1}$ to about $10^{-2}$ $s^{-1}$, about $10^{-2}$ $s^{-1}$ to about $10^{-4}$ $s^{-1}$, about $10^{-4}$ $s^{-1}$ to about $10^{-5}$ $s^{-1}$, about $10^{-5}$ $s^{-1}$ to about $10^{-6}$ $s^{-1}$, about $1$ $s^{-1}$ to about $10^{-6}$ $s^{-1}$, about $10^{-2}$ $s^{-1}$ to about $10^{-6}$ $s^{-1}$, about $10^{-3}$ $s^{-1}$ to about $10^{-6}$ $s^{-1}$, about $10^{-4}$ $s^{-1}$ to about $10^{-6}$ $s^{-1}$, about $10^{-2}$ $s^{-1}$ to about $10^{-5}$ $s^{-1}$, or about $10^{-3}$ $s^{-1}$ to about $10^{-5}$ $s^{-1}$.

In some embodiments, the $IC_{50}$ of the anti-TIGIT mAb is less than 10 nM in a FACS study that the anti-TIGIT mAb competitively block the binding of CD155 (also known as PVR; 0.5 µg/ml) on human TIGIT overexpressed CHO-K1 cells. In some embodiments, the $IC_{50}$ of the anti-TIGIT mAb is less than 500 nM in an inhibition of ligand binding by FACS analysis (competition binding assay), or cell based cytokine release assay. In some embodiments, the $IC_{50}$ of the anti-TIGIT mAb is less than 1 nM, about 1 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM.

Chimeric or Humanized Antibodies

In some embodiments, the anti-TIGIT antibody provided herein is a chimeric antibody. Certain chimeric antibodies are described, e.g., in U.S. Pat. No. 4,816,567; and Morrison et al., *Proc. Nat'l. Acad. Sci. USA,* 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci.* USA 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that can be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Nat'l. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the mAbs are modified, such as humanized, without diminishing the native affinity of the domain for antigen and while reducing its immunogenicity with respect to a heterologous species. For example, the amino acid residues of the antibody heavy chain and light chain variable domains (VH and VL) can be determined, and one or more of the mouse amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of mouse monoclonal antibodies requires the introduction and mutagenesis of a limited amount of amino acids in two chains, the light and the heavy chain and the preservation of the assembly of both chains.

Human Antibodies

In some embodiments, the anti-TIGIT antibody, particularly mAb, provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Transgenic mice or rats capable of producing fully human single-domain antibodies are known in the art. See, e.g., US20090307787A1, U.S. Pat. No. 8,754,287, US20150289489A1, US20100122358A1, and WO2004049794.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals can be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Nat'l. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies can also be generated by isolating Fv clone variable domain sequences selected from human-derived phage display libraries. Such variable domain sequences can then be combined with a desired human constant domain. Techniques for selecting human antibodies from antibody libraries are described below.

Library-Derived Antibodies

Antibodies of the present application can be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Nat'l. Acad. Sci. USA* 101(34): 12467-12472 (2004); and Lee et al., *J. Immunol. Methods* 284(1-2): 119-132(2004). Methods for constructing single-domain antibody libraries have been described, for example, see U.S. Pat. No. 7,371,849.

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Biological Activities

The biological activity of anti-TIGIT mAb described herein can be determined by measuring its half maximal inhibitory concentration ($IC_{50}$), which is a measure of the effectiveness of an antibody in inhibiting a specific biological or biochemical function (such as inhibiting the binding between TIGIT and its ligand, CD155 (also known as PVR)). For example, here $IC_{50}$ can be used to indicate the effective concentration of anti-TIGIT mAb needed to neutralize 50% of TIGIT bioactivity in vitro. $IC_{50}$ is comparable to an $EC_{50}$ for agonist drug or other substance (such as an antibody). $EC_{50}$ also represents the plasma concentration required for obtaining 50% of a maximum effect in vivo. $IC_{50}$ or $EC_{50}$ can be measured by assays known in the art, for example, bioassays such as inhibition of ligand binding by FACS analysis (competition binding assay), cell based cytokine release assay, or luciferase reporter assay.

For example, the blockade of ligand binding can be studied using flow cytometry. CHO cells expressing human TIGIT can be dissociated from adherent culture flasks and mixed with varying concentrations of anti-TIGIT mAb for test, and a constant concentration of labeled-CD155 protein (such as biotin-labeled hCD155/Fc protein). An anti-TIGIT antibody positive control can be employed, such as Atezolizumab. The mixture is equilibrated for 30 minutes at room temperature, washed three times with FACS buffer (PBS containing 1% BSA). Then, an antibody specifically recognizing the labeled CD155 protein of constant concentration (such as PE/Cy5 Streptavidin secondary antibody) is added and incubated for 15 minutes at room temperature. Cells are washed with FACS buffer and analyzed by flow cytometry. Data can be analyzed with Prism (GraphPad Software, San Diego, Calif.) using non-linear regression to calculate $IC_{50}$. The results from the competition assay will demonstrate the ability of anti-TIGIT mAbs in inhibiting the interaction between labeled-CD155 and TIGIT.

The biological activity of anti-TIGIT mAb can also be tested by TIGIT-based blockade assay for cytokine release. In dendritic cells, TIGIT ligation of CD155 inhibits IL-12p40 production and induces IL10 production, thus generating tolerogenic dendritic cells that suppress T cell proliferation and IFN-γ production from responding T cells (Yu et al., 2009). TIGIT further acts in effector T cells to induce a shift from a Type 1 or Type-17 domination to an IL-10 dominated immune response. TIGIT deficient mice exhibit an increase in frequency of cells that are IFN-γ+ as well as IL-17+ CD-4+ T cells while simultaneously showing a near complete loss in IL-10 production after immunization with an antigen (Joller et al., 2011). Thus, blockade of TIGIT pathways by anti-TIGIT antibodies can be studied using a variety of bioassays that monitor T-cell proliferation, IFN-γ release, or IL10 secretion.

In some embodiments, an anti-TIGIT antibody, particularly an anti-TIGIT mAb, of the application blocks or antagonizes signals transduced by the CD155 ligand. In some embodiments, an anti-TIGIT mAb can bind to an epitope on TIGIT so as to inhibit TIGIT from interacting with CD155. In some embodiments, an anti-TIGIT mAb can reduce the binding of TIGIT to CD155 by at least about any of 5%, 10%, 20%, 25%, 30%, 40%, 50%, 60%, 70%, 75%, 80%, 90%, 95%, 99% or 99.9% under conditions in which the ratio of antibody combining site to TIGIT ligand binding site is greater than 1:1 and the concentration of antibody is greater than $10^{-8}$ M.

In some embodiments, there is provided an anti-TIGIT mAb comprising a heavy chain variable domain (VH) with a heavy chain CDR1 comprising the amino acid sequence of any one of SEQ ID NOs:27-39, or a variant thereof comprising up to about 3 (such as about any of 1, 2, or 3) amino acid substitutions; a heavy chain CDR2 comprising the amino acid sequence of any one of SEQ ID NOs:40-52, or a variant thereof comprising up to about 3 (such as about any of 1, 2, or 3) amino acid substitutions; and a heavy CDR3 comprising the amino acid sequence of any one of SEQ ID NOs:53-65, or a variant thereof comprising up to about 3 (such as about any of 1, 2, or 3) amino acid substitutions; and a light chain variable domain (VL) with a light chain CDR1 comprising the amino acid sequence of any one of SEQ ID NOs:66-78, or a variant thereof comprising up to about 3 (such as about any of 1, 2, or 3) amino acid substitutions; a light chain CDR2 comprising the amino acid sequence of any one of SEQ ID NOs:79-91, or a variant thereof comprising up to about 3 (such as about any of 1, 2, or 3) amino acid substitutions; and a light chain CDR3 comprising the amino acid sequence of any one of SEQ ID NOs:92-104, or a variant thereof comprising up to about 3 (such as about any of 1, 2, or 3) amino acid substitutions. In some embodiments, the $K_D$ of the binding between the anti-TIGIT mAb and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT antibody is rodent, chimeric, human, partially humanized, or fully humanized.

In some embodiments, the anti-TIGIT mAb comprises a VH CDR3 comprising the amino acid sequence of any one of SEQ ID NOs:53-65 and a VL CDR3 comprising the amino acid sequence of any one of SEQ ID NOs:92-104, and the amino acid substitutions are in CDR1 and/or CDR2 of VH and VL domains.

Thus, in some embodiments, there is provided an anti-TIGIT mAb comprising a heavy chain variable domain (VH) with a CDR1 comprising the amino acid sequence of any one of SEQ ID NOs:27-39, or a variant thereof comprising up to about 3 (such as about any of 1, 2, or 3) amino acid substitutions; a CDR2 comprising the amino acid sequence of any one of SEQ ID NOs:40-52, or a variant thereof comprising up to about 3 (such as about any of 1, 2, or 3) amino acid substitutions; and a CDR3 comprising the amino acid sequence of any one of SEQ ID NOs:53-65; and a light chain variable domain (VL) with a CDR1 comprising the amino acid sequence of any one of SEQ ID NOs:66-78, or a variant thereof comprising up to about 3 (such as about any of 1, 2, or 3) amino acid substitutions; a CDR2 comprising the amino acid sequence of any one of SEQ ID NOs:79-91, or a variant thereof comprising up to about 3 (such as about any of 1, 2, or 3) amino acid substitutions; and a CDR3 comprising the amino acid sequence of any one of SEQ ID NOs:92-104. In some embodiments, the $K_D$ of the binding between the anti-TIGIT mAb and TIGIT is about $10^{-5}$ M to about $10^{-12}$ M (such as about $10^{-7}$ M to about $10^{-12}$ M, or about $10^{-8}$ M to about $10^{-12}$ M), or less. In some embodiments, the anti-TIGIT mAb is rodent, chimeric, human, partially humanized, or fully humanized.

In some embodiments, there is provided an anti-TIGIT mAb comprising a heavy chain variable domain (VH) with a CDR1 comprising an amino acid sequence of any one of SEQ ID NOs:27-39; a CDR2 comprising an amino acid sequence of any one of SEQ ID NOs:40-52; and a CDR3 comprising an amino acid sequence of any one of SEQ ID NOs:53-65; and a light chain variable domain (VL) with a CDR1 comprising the amino acid sequence of any one of SEQ ID NOs:66-78; a CDR2 comprising the amino acid sequence of any one of SEQ ID NOs:79-91; and a CDR3 comprising the amino acid sequence of any one of SEQ ID NOs:92-104. In some embodiments, the $K_D$ of the binding between the anti-TIGIT mAb and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT mAb is rodent, chimeric, human, partially humanized, or fully humanized.

In some embodiments, an antibody or antigen binding fragment of the application comprises the sequences of the CDRs provided in Tables 17 and 18.

The CDRs can be combined in various pair-wise combinations to generate a number of humanized anti-TIGIT antibodies. Humanized substitutions will be clear to those skilled in the art. For example, potentially useful humanizing substitutions can be determined by comparing the FR sequences of a naturally occurring VH or VL with the corresponding FR sequences of one or more closely related human VH or VL, then introducing one or more of such potentially useful humanizing substitutions into said VH or VL using methods known in the art (also as described herein). The humanized heavy chains and light chains are paired. The resulting humanized antibodies can be tested for their TIGIT binding affinity, for stability, for ease and level of expression, and/or for other desired properties. An anti-TIGIT mAb described herein can be partially or fully humanized. Preferably, the resulting humanized antibody, such as humanized mAb, or an antigen binding fragment thereof, binds to TIGIT with $K_D$, $K_{on}$, $K_{off}$ described herein.

In some embodiments, there is provided an anti-TIGIT humanized mAb or an antigen binding fragment thereof, comprising a VH domain comprising the amino acid sequence of any one of SEQ ID NOs:1-13, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:1-13; and a VL domain comprising the amino acid sequence of any one of SEQ ID NOs:14-26, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:14-26. In some embodiments, there is provided an anti-TIGIT mAb comprising a VH domain comprising the amino acid sequence of any one of SEQ ID NOs:1-13, or a variant thereof comprising up to about 3 (such as about any of 1, 2, or 3) amino acid substitutions in the VH domain; and a VL domain comprising the amino acid sequence of any one of SEQ ID NOs:14-26, or a variant thereof comprising up to about 3 (such as about any of 1, 2, or 3) amino acid substitutions in the VL domain. In some embodiments, an anti-TIGIT mAb or an antigen binding fragment thereof comprises a variant of a VH domain having the amino acid sequence of any one of SEQ ID NOs:1-13, wherein the variant comprises amino acid substitutions in CDRs, such as the CDR1, and/or the CDR2, and/or the CDR3 of the VH; and a variant of a VL domain having the amino acid sequence of any one of SEQ ID NOs:14-26, wherein the variant comprises amino acid substitutions in CDRs, such as the CDR1, and/or the CDR2, and/or the CDR3 of any one of the VL. In some embodiments, an anti-TIGIT mAb or an antigen binding fragment thereof comprises a variant of a VH domain having the amino acid sequence of any one of SEQ ID NOs:1-13, wherein the variant comprises amino acid substitutions in FRs, such as the FR1, and/or the FR2, and/or the FR3, and/or the FR4 of any one of the VH; and a variant of a VL domain having the amino acid sequence of any one of SEQ ID NOs:14-26, wherein the variant comprises amino acid substitutions in FRs, such as the FR1, and/or the FR2, and/or the FR3, and/or the FR4 of any one of SEQ ID NOs:14-26.

In some embodiments, there is provided an anti-TIGIT antibody, such as an mAb (hereinafter referred to as "competing anti-TIGIT antibody or competing anti-TIGIT mAb"), or an antigen binding fragment thereof, that specifically binds to TIGIT competitively with any one of the anti-TIGIT mAb described herein. In some embodiments, competitive binding can be determined using an ELISA assay. For example, in some embodiments, there is provided an anti-TIGIT mAb that specifically binds to TIGIT competitively with an anti-TIGIT mAb comprising the VH amino acid sequence of any one of SEQ ID NOs:1-13 and the VL amino acid sequence of any one of SEQ ID NOs:14-26, respectively. For another example, in some embodiments, there is provided an anti-TIGIT mAb that specifically binds to TIGIT competitively with an anti-TIGIT mAb comprising a heavy chain variable domain (VH) with a CDR1 comprising the amino acid sequence of any one of SEQ ID NOs:27-39; a CDR2 comprising the amino acid sequence of any one of SEQ ID NOs:40-52; and a CDR3 comprising the amino acid sequence of any one of SEQ ID NOs:53-65; and a light chain variable domain (VL) with a CDR1 comprising the amino acid sequence of any one of SEQ ID NOs:66-78; a CDR2 comprising the amino acid sequence of any one of SEQ ID NOs:79-91; and a CDR3 comprising the amino acid sequence of any one of SEQ ID NOs:92-104. For another example, in some embodiments, there is provided an anti-TIGIT mAb that specifically binds to TIGIT competitively with any anti-TIGIT mAb described in Tables 17 and 18. In some embodiments, the $K_D$ of the binding between the competing anti-TIGIT mAb and TIGIT is about $10^{-5}$ M to about $10^{-12}$ M (such as about $10^{-7}$ M to about $10^{-12}$ M, or about $10^{-8}$ M to about $10^{-12}$ M), or less. In some embodiments, the competing anti-TIGIT mAb is rodent, chimeric, human, partially humanized, or fully humanized.

Construct Comprising the Anti-TIGIT mAb

The anti-TIGIT construct comprising the anti-TIGIT mAb can be of any possible format.

In some embodiments, the anti-TIGIT construct comprising the anti-TIGIT mAb can further comprise additional polypeptide sequences, such as one or more antibody moieties. Such additional polypeptide sequences can or cannot change or otherwise influence the (biological) properties of the anti-TIGIT mAb, and can or cannot add further functionality to the anti-TIGIT mAb described herein. In some embodiments, the additional polypeptide sequences confer one or more desired properties or functionalities to the anti-TIGIT mAb of the application. In some embodiments, the anti-TIGIT construct is a chimeric antigen receptor (CAR) comprising an extracellular antigen binding domain comprising one or more anti-TIGIT binding moiety described herein.

In some embodiments, the additional polypeptide sequences can be a second antibody moiety (such as sdAb, scFv) that specifically recognizes a second antigen. In some embodiments, the second antigen is not TIGIT. In some embodiments, the second antibody moiety specifically recognizes the same epitope on TIGIT as the anti-TIGIT mAb described herein. In some embodiments, the second antibody moiety specifically recognizes a different epitope on TIGIT as the anti-TIGIT mAb described herein.

In some embodiments, the additional polypeptide sequences can increase the molecule's stability, solubility, or absorption, reduce immunogenicity or toxicity, eliminate or attenuate undesirable side effects, and/or confer other advantageous properties to and/or reduce undesired properties of the anti-TIGIT construct of the invention, compared to the anti-TIGIT mAb described herein per se.

Full-Length IgG

In some embodiments, an anti-TIGIT mAb is a full-length IgG. In some embodiments, the anti-TIGIT mAb comprises the constant regions of IgG, such as any of IgG1, IgG2, IgG3, or IgG4. In some embodiments, the constant region is human constant region. In some embodiments, the constant region is human IgG1 constant region.

Thus in some embodiments, there is provided an anti-TIGIT full-length IgG comprising a heavy chain, wherein the variable region (VH) comprises a CDR1 comprising the amino acid sequence of any one of SEQ ID NOs:27-39, or a variant thereof comprising up to about 3 (such as about any of 1, 2, or 3) amino acid substitutions; a CDR2 comprising the amino acid sequence of any one of SEQ ID NOs:40-52, or a variant thereof comprising up to about 3 (such as about any of 1, 2, or 3) amino acid substitutions; and a CDR3 comprising the amino acid sequence of any one of SEQ ID NOs:53-65, or a variant thereof comprising up to about 3 (such as about any of 1, 2, or 3) amino acid substitutions, and wherein the VH is fused to the heavy chain constant regions (hinge, $C_H1$, $C_H2$ and $C_H3$) of an immunoglobulin; and a light chain, wherein the variable region (VL) comprises a CDR1 comprising the amino acid sequence of any one of SEQ ID NOs:66-78, or a variant thereof comprising up to about 3 (such as about any of 1, 2, or 3) amino acid substitutions; a CDR2 comprising the amino acid sequence of any one of SEQ ID NOs:79-91, or a variant thereof comprising up to about 3 (such as about any of 1, 2, or 3) amino acid substitutions; and a CDR3 comprising the amino acid sequence of any one of SEQ ID NOs:92-104, or a variant thereof comprising up to about 3 (such as about any of 1, 2, or 3) amino acid substitutions, and wherein the VL is fused to the light chain constant region (CL) of an immunoglobulin. In some embodiments, there is provided an anti-TIGIT full-length IgG comprising a heavy chain, wherein the variable region (VH) comprises a CDR1 comprising the amino acid sequence of any one of SEQ ID NOs:27-39; a CDR2 comprising the amino acid sequence of any one of SEQ ID NOs:40-52; and a CDR3 comprising the amino acid sequence of any one of SEQ ID NOs:53-65, or a variant thereof comprising up to about 3 (such as about any of 1, 2, or 3) amino acid substitutions, and wherein the VH is fused to the heavy chain constant regions (hinge, $C_H1$, $C_H2$ and $C_H3$) of an immunoglobulin; and a light chain, wherein the variable region (VL) comprises a CDR1 comprising the amino acid sequence of any one of SEQ ID NOs:66-78; a CDR2 comprising the amino acid sequence of any one of SEQ ID NOs:79-91; and a CDR3 comprising the amino acid sequence of any one of SEQ ID NOs:92-104, or a variant thereof comprising up to about 3 (such as about any of 1, 2, or 3) amino acid substitutions, and wherein the VL is fused to the light chain constant region (CL) of an immunoglobulin. In some embodiments, the constant regions are human IgG1 constant region. In some embodiments, the $K_D$ of the binding between the full-length anti-TIGIT IgG and TIGIT is about $10^{-5}$ M to about $10^{-12}$ M (such as about $10^{-7}$ M to about $10^{-12}$ M, or about $10^{-8}$ M to about $10^{-12}$ M), or less. In some embodiments, the full-length anti-TIGIT IgG is rodent, chimeric, human, partially humanized, or fully humanized.

In some embodiments, there is provided a full-length anti-TIGIT mAb comprising the heavy chain amino acid sequence of any one of SEQ ID NOs:1-13, and light chain amino acid sequence of any one of SEQ ID NOs:14-26.

In some embodiments, there is also provided a full-length anti-TIGIT IgG (hereinafter referred to as "competing anti-TIGIT IgG") that specifically binds to TIGIT competitively with any one of the full-length anti-TIGIT IgG described herein. Competitive binding can be determined using an ELISA assay. For example, in some embodiments, there is provided an anti-TIGIT IgG that specifically binds to TIGIT competitively with an anti-TIGIT IgG comprising the heavy chain amino acid sequence of any one of SEQ ID NOs:1-13, and light chain amino acid sequence of any one of SEQ ID NOs:14-26. For another example, in some embodiments, there is provided an anti-TIGIT IgG that specifically binds to TIGIT competitively with an anti-TIGIT IgG comprising a heavy chain, wherein the variable region (VH) comprises a CDR1 comprising the amino acid sequence of any one of SEQ ID NOs:27-39; a CDR2 comprising the amino acid sequence of any one of SEQ ID NOs:40-52; and a CDR3 comprising the amino acid sequence of any one of SEQ ID NOs:53-65; and a light chain, wherein the variable region (VL) comprises a CDR1 comprising the amino acid sequence of any one of SEQ ID NOs:66-78; a CDR2 comprising the amino acid sequence of any one of SEQ ID NOs:79-91; and a CDR3 comprising the amino acid sequence of any one of SEQ ID NOs:92-104. In some embodiments, the $K_D$ of the binding between the competing anti-TIGIT IgG and TIGIT is about $10^{-5}$ M to about $10^{-1}$ M (such as about $10^{-7}$ M to about $10^{-12}$ M, or about $10^{-8}$ M to about $10^{-12}$ M) or less. In some embodiments, the competing anti-TIGIT IgG is rodent, chimeric, human, partially humanized, or fully humanized.

Multivalent and/or Multispecific Antibodies

In some embodiments, the anti-TIGIT construct comprises an anti-TIGIT mAb described herein fused to one or more other antibody moiety (such as an antibody moiety that specifically recognizes another antigen). The one or more other antibody moiety can be of any antibody or antibody fragment format, such as an sdAb, a full-length antibody, a Fab, a Fab', a (Fab')$_2$, an Fv, a single chain Fv (scFv), an scFv-scFv, a minibody, or a diabody. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. For a review of multispecific antibodies, see Weidle et al., Cancer Genomics Proteomics, 10(1):1-18, 2013; Geering and Fussenegger, Trends Biotechnol., 33(2):65-79, 2015; Stamova et al., *Antibodies*, 1(2):172-198, 2012. Diabodies are antibody fragments with two antigen-binding sites that can be bivalent or bispecific. See, for example, EP 404,097; WO 1993/01161; Hudson et al., *Nat. Med.* 9:129-134 (2003); and Hollinger et al., *Proc. Nat'l. Acad. Sci. USA* 90: 6444-6448 (1993). Triabodies and tetrabodies are also described in Hudson et al., *Nat. Med.* 9:129-134 (2003). Antibody fragments can be made by various techniques, including but not limited to proteolytic digestion of an intact antibody as well as production by recombinant host cells (e.g. *E. coli* or phage), as described herein. In some embodiments, the one or more other antibody moiety is antibody mimetics, which are small engineered proteins comprising antigen-binding domains reminiscent of antibodies (Geering and Fussenegger, *Trends Biotechnol.*, 33(2):65-79, 2015). These molecules are derived from existing human scaffold proteins and comprise a single polypeptide. Exemplary antibody mimetics that can be comprised within the anti-TIGIT construct described herein can be, but are not limited to, a designed ankyrin repeat protein (DARPin; comprising 3-5 fully synthetic ankyrin repeats flanked by N- and C-terminal Cap domains), an avidity multimer (avimer; a high-affinity protein comprising multiple A domains, each domain with low affinity for a target), or an Anticalin (based on the scaffold of lipocalins, with four accessible loops, the sequence of each can be randomized).

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies can also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Nat'l. Acad. Sci. USA,* 90:6444-6448 (1993)); and using single-chain Fv (scFv) dimers (see, e.g., Gruber et al., *J. Immunol.,* 152:5368 (1994)); and preparing trispecific antibodies as described, e.g., in Tutt et al. *J. Immunol.* 147: 60 (1991); and creating polypeptides comprising tandem single-domain antibodies (see, e.g., U.S. Patent Application No. 20110028695; and Conrath et al. *J. Biol. Chem.,* 2001; 276(10):7346-50). Engineered antibodies with three or more functional antigen binding sites, including "Octopus antibodies," are also included herein (see, e.g., US2006/0025576A1).

Peptide Linkers

In some embodiments, the two or more antibody moieties within the anti-TIGIT construct can be optionally connected by a peptide linker. The length, the degree of flexibility and/or other properties of the peptide linker(s) used in the anti-TIGIT construct can have some influence on properties, including but not limited to the affinity, specificity or avidity for one or more particular antigens or epitopes. For example, longer peptide linkers can be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker can have a naturally occurring sequence, or a non-naturally occurring sequence. For example, a sequence derived from the hinge region of heavy chain only antibodies can be used as the linker. See, for example, WO1996/34103. In some embodiments, the peptide linker is a mutated human IgG1 hinge (EPKSSDKTH-TSPPSP, SEQ ID NO: 121). In some embodiments, the peptide linker is a flexible linker. Exemplary flexible linkers include glycine polymers (G)$_n$ (SEQ ID NO:123), glycine-serine polymers (including, for example, (GS)$_n$ (SEQ ID NO:124), (GSGGS)$_n$ (SEQ ID NO:125), (GGGS)$_n$ (SEQ ID NO:126), and (GGGGS)$_n$ (SEQ ID NO:127), where n is an integer of at least one), glycine-alanine polymers, alanine-serine polymers, and other flexible linkers known in the art. In some embodiments, the peptide linker comprises the amino acid sequence of GGGGSGGGS (SEQ ID NO: 119). In some embodiments, the peptide linker comprises the amino acid sequence of SEQ ID NO: 120 (GGGGSGGGGSGGGGS).

Bispecific Antibodies

In some embodiments, an isolated antibody or antigen binding fragment of the application is a bispecific or multispecific antibody that comprises an anti-TIGIT IgG described herein fused to a second antibody moiety, wherein the second antibody moiety binds specifically to another antigen, preferably another inhibitory immune checkpoint molecules.

In an embodiment, the other antigen is CTLA-4 and the second antibody moiety comprises an antibody or antigen binding fragment that binds specifically to CTLA-4, such as an anti-CTLA-4 mAb, preferably an anti-CTLA-4 sdAb. The isolated antibody or antigen binding fragment comprising bi-specificity against TIGIT and CTLA-4 can be hereinafter referred to as "anti-TIGIT/CTLA-4 antibody," "anti-TIGIT/CTLA-4 construct," or "TIGIT×CTLA-4 antibody."

In an embodiment, the other antigen is PD-L1 and the second antibody moiety comprises an antibody or antigen binding fragment that binds specifically to PD-L1, such as an anti-PD-L1 mAb, preferably an anti-PD-L1 sdAb. The isolated antibody or antigen binding fragment comprising bi-specificity against TIGIT and PD-L1 can be hereinafter referred to as "anti-TIGIT/PD-L1 antibody," "anti-TIGIT/PD-L1 construct," or "TIGIT×PD-L1 antibody."

In an embodiment, the other antigen is TIM-3 and the second antibody moiety comprises an antibody or antigen binding fragment that binds specifically to TIM-3, such as an anti-TIM-3 mAb, preferably an anti-TIM3 sdAb. The isolated antibody or antigen binding fragment comprising bi-specificity against TIGIT and TIM-3 can be hereinafter referred to as "anti-TIGIT/TIM-3 antibody," "anti-TIGIT/TIM-3 construct," or "TIGIT×TIM-3 antibody."

In an embodiment, the other antigen is LAG-3 and the second antibody moiety comprises an antibody or antigen binding fragment that binds specifically to LAG-3, such as an anti-LAG-3 mAb, preferably an anti-LAG-3 sdAb. The isolated antibody or antigen binding fragment having bi-specificity against TIGIT and LAG-3 can be hereinafter referred to as "anti-TIGIT/LAG-3 antibody," "anti-TIGIT/LAG-3 construct," or "TIGIT×LAG-3 antibody."

CTLA-4, PD-L1, TIM-3 and LAG-3, similar to TIGIT, are inhibitory immune checkpoint molecules.

In some embodiments, there is provided an isolated anti-TIGIT construct comprising a full-length IgG specifically recognizing TIGIT and an sdAb selected from the group consisting of an anti-CTLA-4 sdAb, an anti-PD-L1 sdAb, an anti-TIM-3 sdAb, and an anti-LAG-3 sdAb, wherein the anti-TIGIT IgG comprises a heavy chain, wherein the variable region (VH) comprises a CDR1 comprising the amino acid sequence of any one of SEQ ID NOs:27-39, or a variant thereof comprising up to about 3 (such as about any of 1, 2, or 3) amino acid substitutions; a CDR2 comprising the amino acid sequence of any one of SEQ ID NOs:40-52, or a variant thereof comprising up to about 3 (such as about any of 1, 2, or 3) amino acid substitutions; and a CDR3 comprising the amino acid sequence of any one of SEQ ID NOs:53-65, or a variant thereof comprising up to about 3 (such as about any of 1, 2, or 3) amino acid substitutions, and wherein the VH is fused to the heavy chain constant regions (hinge, $C_H1$, $C_H2$ and $C_H3$) of an immunoglobulin; and a light chain, wherein the variable region (VL) comprises a CDR1 comprising the amino acid sequence of any one of SEQ ID NOs:66-78, or a variant thereof comprising up to about 3 (such as about any of 1, 2, or 3) amino acid substitutions; a CDR2 comprising the amino acid sequence of any one of SEQ ID NOs:79-91, or a variant thereof comprising up to about 3 (such as about any of 1, 2, or 3) amino acid substitutions; and a CDR3 comprising the amino acid sequence of any one of SEQ ID NOs:92-104, or a variant thereof comprising up to about 3 (such as about any of 1, 2, or 3) amino acid substitutions, and wherein the VL is fused to the light chain constant region (CL) of an immunoglobulin. In some embodiments, the N terminus of the sdAb is fused to the C terminus of at least one of the heavy chains of the full-length antibody specifically recognizing TIGIT. In some embodiments, the C terminus of the sdAb is fused to the N terminus of at least one of the heavy chains of the full-length antibody specifically recognizing TIGIT. In some embodiments, the N terminus of the sdAb is fused to the C terminus of at least one of the light chains of the full-length antibody specifically recognizing TIGIT. In some embodiments, the C terminus of the sdAb is fused to the N terminus of at least one of the light chains of the full-length antibody specifically recognizing TIGIT. In some embodiments, the full-length IgG specifically recognizing TIGIT and the second binding moiety sdAb are optionally connected by a peptide linker. In some embodiments, the peptide linker comprises the amino acid sequence of SEQ ID NO:119-121. In some embodiments, the $K_D$ of the binding between the anti-TIGIT mAb and TIGIT is about $10^{-5}$ M to about $10^{-12}$ M (such as about $10^{-7}$ M to about $10^{-12}$ M, or about $10^{-8}$ M to about $10^{-12}$ M), or less. In some embodiments, the anti-TIGIT IgG is rodent, chimeric, human, partially humanized, or fully humanized.

In some embodiments, there is provided an anti-TIGIT construct comprising a full-length IgG specifically recognizing TIGIT and an sdAb selected from the group consisting of an anti-CTLA-4 sdAb, an anti-PD-L1 sdAb, an anti-TIM4-3 sdAb, and an anti-LAG-3 sdAb, wherein the full-length IgG comprises a VH domain comprising the amino acid sequence of any one of SEQ ID NOs:1-13, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:1-13 and wherein the VH is fused to the heavy chain constant regions (hinge, $C_H1$, $C_H2$ and $C_H3$) of an immunoglobulin; and a VL domain comprising the amino acid sequence of any one of SEQ ID NOs:14-26, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:14-26 and wherein the VL is fused to the light chain constant regions (CL) of an immunoglobulin. In some embodiments, there is provided an isolated anti-TIGIT construct comprising a full-length IgG specifically recognizing TIGIT and an sdAb selected from the group consisting of an anti-CTLA-4 sdAb, an anti-PD-L1 sdAb, an anti-TIM-3 sdAb, and an anti-LAG-3 sdAb, wherein the full-length IgG comprises a VH domain comprising the amino acid sequence of any one of SEQ ID NOs:1-13, or a variant thereof comprising up to about 3 (such as about any of 1, 2, or 3) amino acid substitutions in the VH domain and wherein the VH is fused to the heavy chain constant regions (hinge, $C_H1$, $C_H2$ and $C_H3$) of an immunoglobulin; and a VL domain comprising the amino acid sequence of any one of SEQ ID NOs:14-26, or a variant thereof comprising up to about 3 (such as about any of 1, 2, or 3) amino acid substitutions in the VL domain and wherein the VL is fused to the light chain constant regions (CL) of an immunoglobulin.

In some embodiments, the anti-TIGIT full-length IgG comprising the VH domain comprising the amino acid sequence of any one of SEQ ID NOs:1-13 or a variant thereof comprises amino acid substitutions in CDRs, such as the CDR1, and/or the CDR2, and/or the CDR3 of any one of SEQ ID NOs:1-13, and where in the VH is fused to the heavy chain constant regions (hinge, $C_H1$, $C_H2$ and $C_H3$) of an immunoglobulin; and the VL domain comprising the amino acid sequence of any one of SEQ ID NOs:14-26 or a variant thereof comprises amino acid substitutions in CDRs, such as the CDR1, and/or the CDR2, and/or the CDR3 of any one of SEQ ID NOs:14-26, and where in the VH fused to the light chain constant regions (CL) of an immunoglobulin. In some embodiments, the anti-TIGIT full-length IgG comprising the VH domain comprising the amino acid sequence of any one of SEQ ID NOs:1-13 or a variant thereof comprises CDR1, CDR2, and CDR3 of any one of SEQ ID NOs:1-13, and the amino acid substitutions are in FRs, such as the FR1, and/or the FR2, and/or the FR3, and/or the FR4 of any one of SEQ ID NOs:1-13, and wherein the VH is fused to the heavy chain constant regions (hinge, $C_H1$, $C_H2$ and $C_H3$) of an immunoglobulin; and the VL domain comprising the amino acid sequence of any one of SEQ ID NOs:14-26 or a variant thereof comprises CDR1, CDR2, and CDR3 of any one of SEQ ID NOs:14-26, and the amino acid substitutions are in FRs, such as the FR1, and/or the FR2, and/or the FR3, and/or the FR4 of any one of SEQ ID NOs:14-26, and wherein the VL is fused to the light chain constant regions (CL) of an immunoglobulin. In some embodiments, the anti-TIGIT full-length IgG comprising the VH domain comprising the amino acid sequence of any one of SEQ ID NOs:1-13 or a variant thereof comprises amino acid substitutions in both CDRs and FRs, and wherein the VH is fused to the heavy chain constant regions (hinge, $C_H1$, $C_H2$ and $C_H3$) of an immunoglobulin; and the VL domain comprising the amino acid sequence of any one of SEQ ID NOs:14-26 or a variant thereof comprises amino acid substitutions in both CDRs and FRs, and wherein the VL is fused to the light chain constant regions (CL) of an immunoglobulin. In some embodiments, there is provided an isolated anti-TIGIT construct comprising a full-length IgG specifically recognizing TIGIT and an sdAb selected from the group consisting of an anti-CTLA-4 sdAb, an anti-PD-L1 sdAb, an anti-TIM4-3 sdAb, and an anti-LAG-3 sdAb, wherein the full-length IgG comprises a VH domain comprising the amino acid sequence of any one of SEQ ID NOs:1-13 fused to the heavy chain constant regions (hinge, $C_H1$, $C_H2$ and $C_H3$) of an immunoglobulin; and a VL domain comprising the amino acid sequence of any one of SEQ ID NOs:14-26 fused to the light chain constant regions (CL) of an immunoglobulin. In some embodiments, the N terminus of the sdAb is fused to the C terminus of at least one of the heavy chains of the full-length antibody specifically recognizing TIGIT. In some embodiments, the C terminus of the sdAb is fused to the N terminus of at least one of the heavy chains of the full-length antibody specifically recognizing TIGIT. In some embodiments, the N terminus of the sdAb is fused to the C terminus of at least one of the light chains of the full-length antibody specifically recognizing TIGIT. In some embodiments, the C terminus of the sdAb is fused to the N terminus of at least one of the light chains of the full-length antibody specifically recognizing TIGIT. In some embodiments, the full-length IgG specifically recognizing TIGIT and the second binding moiety sdAb are optionally connected by a peptide linker. In some embodiments, the peptide linker comprises the amino acid sequence of SEQ ID NO: 119-121. In some embodiments, the $K_D$ of the binding between the anti-TIGIT mAb and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT mAb is rodent, chimeric, human, partially humanized, or fully humanized.

In some embodiments, there is also provided an anti-TIGIT construct comprising a full-length IgG specifically recognizing TIGIT (hereinafter referred to as "competing anti-TIGIT construct") that specifically binds to TIGIT competitively with any one of the anti-TIGIT/CTLA-4 constructs, anti-TIGIT/PD-L1 constructs, anti-TIGIT/TIM-3 constructs or anti-TIGIT/LAG-3 constructs described herein.

Anti-PD-L1 Antibody Variants

In some embodiments, amino acid sequence variants of the antibodies provided herein are contemplated. For example, it can be desirable to improve the binding affinity and/or other biological properties of the antibody. Amino acid sequence variants of an antibody can be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions can be introduced into an antibody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids can be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which can be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) can be made in HVRs, e.g., to improve antibody affinity. Such alterations can be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding can be specifically identified, e.g., using alanine scanning mutagenesis or modeling. CDR-H3 and CDR-L3 in particular are often targeted.

In some embodiments, substitutions, insertions, or deletions can occur within one or more HVRs so long as such alterations do not substantially reduce the ability of the antibody to bind antigen. For example, conservative alterations (e.g., conservative substitutions as provided herein) that do not substantially reduce binding affinity can be made in HVRs. Such alterations can be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that can be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions can be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues can be targeted or eliminated as candidates for substitution. Variants can be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an anti-TIGIT construct provided herein is altered to increase or decrease the extent to which the construct is glycosylated. Addition or deletion of glycosylation sites to an antibody can be conveniently accomplished by altering the amino acid sequence such that one or more glycosylation sites is created or removed.

Where the anti-TIGIT construct comprises an Fc region, the carbohydrate attached thereto can be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide can include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PD-L1 construct of the present application can be made in order to create antibody variants with certain improved properties.

In some embodiments, antibody variants are provided having a carbohydrate structure that lacks fucose attached (directly or indirectly) to an Fc region. For example, the amount of fucose in such antibody can be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 can also be located about 3 amino acids upstream or downstream of position 297, i.e., between positions 294 and 300, due to minor sequence variations in antibodies. Such fucosylation variants can have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-TIGIT construct variants are further provided with bisected oligosaccharides, e.g., in which a biantennary oligosaccharide attached to the Fc region of the antibody is bisected by GlcNAc. Such antibody variants can have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants can have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications can be introduced into the Fc region of the anti-TIGIT construct provided herein, thereby generating an Fc region variant. The Fc region variant can comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-TIGIT construct variant that possesses some but not all effector functions, which make it a desirable candidate for applications in which the half-life of the anti-TIGIT construct in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'Acad. Sci.* USA 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods can be employed (see, for example, ACTI™ non-radioactive cytotoxicity assay for flow cytometry (Cell Technology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *Proc. Nat'Acad. Sci.* USA 95:652-656 (1998). C1q binding assays can also be carried out to confirm that the antibody is unable to bind C1q and hence lacks CDC activity. See, e.g., C1q and C3c binding ELISA in WO 2006/029879 and WO 2005/100402. To assess complement activation, a CDC assay can be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an anti-TIGIT construct variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, there is provided an anti-TIGIT construct (e.g., a HCAb) variant comprising a variant Fc region comprising one or more amino acid substitutions which increase half-life and/or improve binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-TIGIT constructs (such as full-length IgG or anti-TIGIT IgG fused to an sdAb) comprising any of the Fc variants described herein, or combinations thereof, are contemplated.

d) Cysteine Engineered Antibody Variants

In some embodiments, it can be desirable to create cysteine engineered anti-TIGIT constructs, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and can be used to conjugate the antibody to other moieties, such as drug moieties or linker-drug moieties, to create an immunoconjugate, as described further herein. In some embodiments, any one or more of the following residues can be substituted with cysteine: A118 (EU numbering) of the heavy chain; and S400 (EU numbering) of the heavy chain Fc region. Cysteine engineered anti-TIGIT constructs can be generated as described, e.g., in U.S. Pat. No. 7,521,541.

e) Antibody Derivatives

In some embodiments, an anti-TIGIT construct provided herein can be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water. The polymer can be of any molecular weight, and can be branched or unbranched. The number of polymers attached to the antibody can vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an anti-TIGIT construct and nonproteinaceous moiety that can be selectively heated by exposure to radiation are provided. In some embodiments, the nonproteinaceous moiety is a carbon nanotube (Kam et al., *Proc. Nat'l. Acad. Sci. USA* 102: 11600-11605 (2005)). The radiation can be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-TIGIT construct provided herein (such as anti-TIGIT IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody) can be further modified to contain one or more biologically active protein, polypeptides or fragments thereof. "Bioactive" or "biologically active" as used herein means showing biological activity in the body to carry out a specific function. For example, it can mean the combination with a particular biomolecule such as protein, DNA, etc., and then promotion or inhibition of the activity of such biomolecule. In some embodiments, the bioactive protein or fragments thereof have immunostimulatory/immunoregulatory, membrane transport, or enzymatic activities.

In some embodiments, the bioactive protein or fragments thereof that can be fused with the anti-TIGIT construct described herein is a ligand, such as lymphokines and cellular factors which interact with specific cellular receptor. Lymphokines are low molecular weight proteins which are secreted by T cells when antigens or lectins stimulate T cell growth. Examples of lymphokines include, but are not limited to, interferon-α, interferon-γ, interleukin-1 (IL-1), interleukin-2 (IL-2), interleukin-3 (IL-3), tumor necrosis factor (TNF), a colony stimulating factor (e.g. CSF-1, G-CSF or GM-CSF), chemotaxins, macrophage migration inhibitory factor (MIF), macrophage-activating factor (MAF), NK cell activating factor, T cell replacing factor, leukocyte-inhibitory factor (LIF), lymphotoxins, osteoclast-activating factor (OAF), soluble immune response suppressor (SIRS), growth-stimulating factor, monocyte growth factor, etc. Cellular factors which can be incorporated into the anti-TIGIT fusion proteins of the invention include but are not limited to tumor necrosis factor α (TNFα), interferons (IFNs), and nerve growth factor (NGF), etc.

III. Pharmaceutical Compositions

Further provided by the present application are pharmaceutical compositions comprising any one of the anti-TIGIT constructs comprising a full-length IgG specifically recognizing TIGIT as described herein (such as anti-TIGIT IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody), and optionally a pharmaceutically acceptable carrier. Pharmaceutical compositions can be prepared by mixing an anti-TIGIT construct described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the anti-TIGIT construct comprising anti-TIGIT mAb described here essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation can be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of anti-TIGIT construct described herein can comprise less than about 10% (preferably less than about 5%) of the anti-TIGIT construct present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™ polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers can comprise histidine and trimethylamine salts such as Tris.

Preservatives are added to retard microbial growth, and are typically present in a range from 0.2%-1.0% (w/v). The addition of a preservative can, for example, facilitate the production of a multi-use (multiple-dose) formulation. Suitable preservatives for use in the present application include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition can be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally.

Sustained-release preparations can be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), orpoly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The pharmaceutical compositions herein can also contain more than one active compound as necessary for the particular indication being treated, preferably those with complementary activities that do not adversely affect each other. Alternatively, or in addition, the composition can comprise a cytotoxic agent, chemotherapeutic agent, cytokine, immunosuppressive agent, or growth inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Uses or Applications

The anti-TIGIT construct comprising mAb specifically recognizing TIGIT as described herein (such as anti-TIGIT full-length IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody), and the compositions (such as pharmaceutical compositions) thereof are useful for a variety of applications, such as in diagnosis, molecular assays, and therapy.

One aspect of the invention provides a method of treating a TIGIT related disease or a condition in an individual in need thereof, comprising administering to the individual an effective amount of a pharmaceutical composition comprising the anti-TIGIT construct described herein. In some embodiments, the TIGIT related disease is cancer. In some embodiments, the TIGIT related disease is pathogenic infection, such as viral infection.

The application contemplates, in part, protein constructs (such as anti-TIGIT full-length IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody), nucleic acid molecules and/or vectors encoding thereof, host cells comprising nucleic acid molecules and/or vectors encoding thereof, that can be administered either alone or in any combination with another therapy, and in at least some aspects, together with a pharmaceutically acceptable carrier or excipient. In some embodiments, prior to administration of the anti-TIGIT construct, they can be combined with suitable pharmaceutical carriers and excipients that are well known in the art.

The compositions prepared according to the disclosure can be used for the treatment or delaying of worsening of cancer.

In some embodiments, there is provided a method of treating cancer comprising administering to the individual an effective amount of a pharmaceutical composition comprising an isolated anti-TIGIT construct comprising a mAb specifically recognizing TIGIT (such as anti-TIGIT full-length IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody). In some embodiments, the cancer is a solid tumor (such as colon cancer). In some embodiments, the pharmaceutical composition is administered systemically (such as intravenously). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein can be used as a first therapy, second therapy, third therapy, or combination therapy with other types of cancer therapies known in the art, such as chemotherapy, surgery, hormone therapy, radiation, gene therapy, immunotherapy (such as T-cell therapy), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method can be carried out before the primary/definitive therapy). In some embodiments, the method is used to treat an individual who has previously been treated. In some embodiments, the cancer has been refractory to prior therapy. In some embodiments, the method is used to treat an individual who has not previously been treated.

In some embodiments, the method is suitable for treating cancers with aberrant TIGIT expression, activity and/or signaling include, by way of non-limiting example, melanoma, prostate cancer, lung cancer, colon cancer, gastric cancer, ovarian cancer, breast cancer, and glioblastoma.

Thus in some embodiments, there is provided a method of treating an immunotherapy-responsive solid tumor (such as carcinoma or adenocarcinoma, such as cancers with aberrant TIGIT expression, activity and/or signaling), comprising administering to the individual an effective amount of a pharmaceutical composition comprising an isolated anti-TIGIT construct comprising a monoclonal antibody specifically recognizing TIGIT (such as anti-TIGIT full-length IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody). In some embodiments, the cancer is a solid tumor (such as colon cancer). In some embodiments, the pharmaceutical composition is administered systemically (such as intravenously). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

In some embodiments, the method is suitable for treating cancers with aberrant CD155 or TIGIT expression, activity and/or signaling include, by way of non-limiting example, hematological cancer and/or solid tumors. Some cancers whose growth can be inhibited using the antibodies of the invention include cancers typically responsive to immunotherapy. Non-limiting examples of other cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth can be inhibited using the antibodies of the invention. Examples of other cancers that can be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The application is also useful for treatment of metastatic cancers, especially metastatic cancers that express TIGIT (Iwai et al. (2005) Int. Immunol. 17:133-144).

Thus, in some embodiments, there is provided a method of treating an immunotherapy-responsive solid tumor (such as carcinoma or adenocarcinoma, such as cancers with aberrant TIGIT expression, activity and/or signaling, and/or aberrant CTLA-4, PD-L1, TIM-3 and LAG-3 expression, activity and/or signaling), comprising administering to the individual an effective amount of a pharmaceutical composition comprising an isolated anti-TIGIT construct comprising a full-length IgG specifically recognizing TIGIT fused to a CTLA-4, PD-L1, TIM-3 or LAG-3 sdAb. In some embodiments, there is provided a method of treating an immunotherapy-responsive solid tumor (such as carcinoma or adenocarcinoma, such as cancers with aberrant TIGIT expression, activity and/or signaling, and/or aberrant CTLA-4, PD-L1, TIM-3, LAG-3 expression, activity and/or signaling), comprising administering to the individual an effective amount of a pharmaceutical composition comprising an isolated anti-TIGIT construct comprising a full-length IgG specifically recognizing TIGIT fused to a CTLA-4, PD-L1, TIM-3 or LAG-3 sdAb.

In some embodiments, the method described herein is suitable for treating a colorectal cancer, such as adenocarcinoma, gastrointestinal carcinoid tumor, gastrointestinal stromal tumor, Leiomyosarcoma, melanoma, or squamous cell carcinoma.

Dosages and desired drug concentrations of pharmaceutical compositions of the present application can vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the anti-TIGIT construct comprising an anti-TIGIT mAb described herein are used, normal dosage amounts can vary from about 10 ng/kg up to about 100 mg/kg of mammal body weight or more per day, preferably about 1 mg/kg/day to 10 mg/kg/day, such as about 1-3 mg/kg/day, about 2-4 mg/kg/day, about 3-5 mg/kg/day, about 4-6 mg/kg/day, about 5-7 mg/kg/day, about 6-8 mg/kg/day, about 6-6.5 mg/kg/day, about 6.5-7 mg/kg/day, about 7-9 mg/kg/day, or about 8-10 mg/kg/day, depending upon the route of administration. It is within the scope of the present application that different formulations will be effective for different treatments and different disorders, and that administration intended to treat a specific organ or tissue can necessitate delivery in a manner different from that to another organ or tissue. Moreover, dosages can be administered by one or more separate administrations, or by continuous infusion. For repeated administrations over several days or longer, depending on the condition, the treatment is sustained until a desired suppression of disease symptoms occurs. However, other dosage regimens can be useful. The progress of this therapy is easily monitored by conventional techniques and assays.

In some embodiments, the pharmaceutical composition is administered for a single time (e.g. bolus injection). In some embodiments, the pharmaceutical composition is administered for multiple times (such as any of 2, 3, 4, 5, 6, or more times). If multiple administrations, they can be performed by the same or different routes and can take place at the same site or at alternative sites. The pharmaceutical composition can be administered twice per week, 3 times per week, 4 times per week, 5 times per week, daily, daily without break, once per week, weekly without break, once per 2 weeks, once per 3 weeks, once per month, once per 2 months, once per 3 months, once per 4 months, once per 5 months, once per 6 months, once per 7 months, once per 8 months, once per 9 months, once per 10 months, once per 11 months, or once per year. The interval between administrations can be about any one of 24 h to 48 h, 2 days to 3 days, 3 days to 5 days, 5 days to 1 week, 1 week to 2 weeks, 2 weeks to 1 month, 1 month to 2 months, 2 month to 3 months, 3 months to 6 months, or 6 months to a year. Intervals can also be irregular (e.g. following tumor progression). In some embodiments, there is no break in the dosing schedule. In some embodiments, the pharmaceutical composition is administered every 4 days for 4 times. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment with the anti-TIGIT construct described herein, preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized anti-TIGIT construct described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions can be injected using a syringe. However, other devices for administration of the pharmaceutical compositions are available such as injection devices; injector pens; auto-injector devices, needleless devices; and subcutaneous patch delivery systems.

In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., *New Eng. J. of Med.* 319: 1676 (1988)).

The anti-TIGIT construct comprising mAb specifically recognizing TIGIT as described herein (such as anti-TIGIT full-length IgG, anti-TIGIT/CTLA-4 bispecific antibody, anti-TIGIT/PD-L1 bispecific antibody, anti-TIGIT/TIM-3 bispecific antibody or anti-TIGIT/LAG-3 bispecific antibody), and the compositions (such as pharmaceutical compositions) thereof are also useful in diagnosis or molecular assays. For example, the antibody or antigen binding fragment can be used for the detection or quantification of TIGIT in a biological sample, thereby detecting or monitoring the progress or treatment of a disease, such as those described above, related to TIGIT.

V. Methods of Preparation

The anti-TIGIT construct (such as anti-TIGIT monoclonal antibody) described herein can be prepared using any methods known in the art or as described herein.

Rodent monoclonal antibodies can be obtained using methods known in the art such as by immunizing a rodent species (such as mouse or rat) and obtaining hybridomas therefrom, or by cloning a library of Fab fragment or single chain Fc (scFv) using molecular biology techniques known in the art and subsequent selection by ELISA with individual clones of unselected libraries or by using phage display.

For recombinant production of the monoclonal antibodies, the nucleic acids encoding the monoclonal antibodies are isolated or synthesized and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

EMBODIMENTS

The invention provides also the following non-limiting embodiments.

Embodiment 1 comprises an isolated antibody, preferably a mAb, or an antigen-binding fragment thereof, comprising:
(a) a heavy chain variable domain (VH) comprising:
  i. a heavy chain complementarity determining region 1 (CDR1) comprising an amino acid sequence selected from the group consisting of SEQ ID NOs:27-39;
  ii. a heavy chain CDR2 comprising an amino acid sequence selected from the group consisting of SEQ ID NOs:40-52; and
  iii. a heavy chain CDR3 comprising an amino acid sequence selected from the group consisting of SEQ ID NOs:53-65, respectively; and
(b) a light chain variable domain (VL) comprising:
  i. a light chain CDR1 comprising an amino acid sequence selected from the group consisting of SEQ ID NOs:66-78;
  ii. a light chain CDR2 comprising an amino acid sequence selected from the group consisting of SEQ ID NOs:79-91; and
  iii. a light chain CDR3 comprising an amino acid sequence selected from the group consisting of SEQ ID NOs:92-104, respectively;
  wherein the antibody or antigen-binding fragment thereof is capable of specifically binding to a TIGIT, preferably a human TIGIT.

Embodiment 2 is the isolated antibody or antigen-binding fragment thereof of embodiment 1, wherein:
(1) the VH comprises the heavy chain CDR1, CDR2, and CDR3 sequences having the amino acid sequences of SEQ ID NOs:27, 40, and 53, respectively, and the VL comprises the light chain CDR1, CDR2, and CDR3 having the amino acid sequences of SEQ ID NOs:66, 79, and 92, respectively;
(2) the VH comprises the heavy chain CDR1, CDR2, and CDR3 sequences having the amino acid sequences of SEQ ID NOs:28, 41, and 54, respectively, and the VL comprises the light chain CDR1, CDR2, and CDR3 having the amino acid sequences of SEQ ID NOs:67, 80, and 93, respectively;
(3) the VH comprises the heavy chain CDR1, CDR2, and CDR3 sequences having the amino acid sequences of SEQ ID NOs:29, 42, and 55, respectively, and the VL comprises the light chain CDR1, CDR2, and CDR3 having the amino acid sequences of SEQ ID NOs:68, 81, and 94, respectively;
(4) the VH comprises the heavy chain CDR1, CDR2, and CDR3 sequences having the amino acid sequences of SEQ ID NOs:30, 43, and 56, respectively, and the VL comprises the light chain CDR1, CDR2, and CDR3 having the amino acid sequences of SEQ ID NOs:69, 82, and 95, respectively;
(5) the VH comprises the heavy chain CDR1, CDR2, and CDR3 sequences having the amino acid sequences of SEQ ID NOs:31, 44, and 57, respectively, and the VL comprises the light chain CDR1, CDR2, and CDR3 having the amino acid sequences of SEQ ID NOs:70, 83, and 96, respectively;
(6) the VH comprises the heavy chain CDR1, CDR2, and CDR3 sequences having the amino acid sequences of SEQ ID NOs:32, 45, and 58, respectively, and the VL comprises the light chain CDR1, CDR2, and CDR3 having the amino acid sequences of SEQ ID NOs:71, 84, and 97, respectively;
(7) the VH comprises the heavy chain CDR1, CDR2, and CDR3 sequences having the amino acid sequences of SEQ ID NOs:33, 46, and 59, respectively, and the VL comprises the light chain CDR1, CDR2, and CDR3 having the amino acid sequences of SEQ ID NOs:72, 85, and 98, respectively;
(8) the VH comprises the heavy chain CDR1, CDR2, and CDR3 sequences having the amino acid sequences of SEQ ID NOs:34, 47, and 60, respectively, and the VL comprises the light chain CDR1, CDR2, and CDR3 having the amino acid sequences of SEQ ID NOs:73, 86, and 99, respectively;
(9) the VH comprises the heavy chain CDR1, CDR2, and CDR3 sequences having the amino acid sequences of SEQ ID NOs:35, 48, and 61, respectively, and the VL comprises the light chain CDR1, CDR2, and CDR3 having the amino acid sequences of SEQ ID NOs:74, 87, and 100, respectively;
(10) the VH comprises the heavy chain CDR1, CDR2, and CDR3 sequences having the amino acid sequences of SEQ ID NOs:36, 49, and 62, respectively, and the VL comprises the light chain CDR1, CDR2, and CDR3 having the amino acid sequences of SEQ ID NOs:75, 88, and 101, respectively;
(11) the VH comprises the heavy chain CDR1, CDR2, and CDR3 sequences having the amino acid sequences of SEQ ID NOs:37, 50, and 63, respectively, and the VL comprises the light chain CDR1, CDR2, and CDR3 having the amino acid sequences of SEQ ID NOs:76, 89, and 102, respectively;
(12) the VH comprises the heavy chain CDR1, CDR2, and CDR3 sequences having the amino acid sequences of SEQ ID NOs:38, 51, and 64, respectively, and the VL comprises the light chain CDR1, CDR2, and CDR3 having the amino acid sequences of SEQ ID NOs:77, 90, and 103, respectively; or
(13) the VH comprises the heavy chain CDR1, CDR2, and CDR3 sequences having the amino acid sequences of SEQ ID NOs:39, 52, and 65, respectively, and the VL comprises the light chain CDR1, CDR2, and CDR3 having the amino acid sequences of SEQ ID NOs:78, 91, and 104, respectively.

Embodiment 3 is the isolated antibody or antigen-binding fragment thereof of embodiment 2, wherein the VH comprises the heavy chain CDR1, CDR2, and CDR3 sequences having the amino acid sequences of SEQ ID NOs: 38, 51, and 64, respectively, and the VL comprises the light chain CDR1, CDR2, and CDR3 having the amino acid sequences of SEQ ID NOs: 77, 90, and 103, respectively.

Embodiment 4 is the isolated antibody or antigen-binding fragment thereof of embodiment 2, wherein the VH comprises the heavy chain CDR1, CDR2, and CDR3 sequences having the amino acid sequences of SEQ ID NOs: 39, 52, and 65, respectively, and the VL comprises the light chain CDR1, CDR2, and CDR3 having the amino acid sequences of SEQ ID NOs: 78, 91, and 104.

Embodiment 5 is the isolated antibody or antigen-binding fragment thereof of any one of embodiments 1-4, wherein the VH comprises an amino acid sequence of any one of SEQ ID NOs:1-13, or a variant thereof having at least about 80%, at least about 90%, or at least about 95% sequence identity to any one of SEQ ID NOs:1-13, and the VL comprises an amino acid sequence of any one of SEQ ID NOs:14-26, or a variant thereof having at least about 80%, at least about 90%, or at least about 95% sequence identity to any one of SEQ ID NOs:14-26, respectively.

Embodiment 6 is the isolated antibody or antigen-binding fragment thereof of embodiment 5, wherein the VH comprises the amino acid sequence selected from the group consisting of SEQ ID NOs: 1-13, or a variant thereof comprising up to about 3 amino acid substitutions in the VH; and the VL comprises the amino acid sequence selected from the group consisting of SEQ ID NOs: 14-26, or a variant thereof comprising up to about 3 amino acid substitutions in the VL.

Embodiment 7 is the isolated antibody or antigen-binding fragment thereof of embodiment 5 or 6, wherein:
(1) the VH comprises an amino acid sequence of SEQ ID NO:1, and the VL comprises an amino acid sequence of SEQ ID NO:14;
(2) the VH comprises an amino acid sequence of SEQ ID NO:2, and the VL comprises an amino acid sequence of SEQ ID NO:15;
(3) the VH comprises an amino acid sequence of SEQ ID NO:3, and the VL comprises an amino acid sequence of SEQ ID NO:16;
(4) the VH comprises an amino acid sequence of SEQ ID NO:4, and the VL comprises an amino acid sequence of SEQ ID NO:17;
(5) the VH comprises an amino acid sequence of SEQ ID NO:5, and the VL comprises an amino acid sequence of SEQ ID NO:18;
(6) the VH comprises an amino acid sequence of SEQ ID NO:6, and the VL comprises an amino acid sequence of SEQ ID NO:19;
(7) the VH comprises an amino acid sequence of SEQ ID NO:7, and the VL comprises an amino acid sequence of SEQ ID NO:20;
(8) the VH comprises an amino acid sequence of SEQ ID NO:8, and the VL comprises an amino acid sequence of SEQ ID NO:21;
(9) the VH comprises an amino acid sequence of SEQ ID NO:9, and the VL comprises an amino acid sequence of SEQ ID NO:22;
(10) the VH comprises an amino acid sequence of SEQ ID NO:10, and the VL comprises an amino acid sequence of SEQ ID NO:23;
(11) the VH comprises an amino acid sequence of SEQ ID NO:11, and the VL comprises an amino acid sequence of SEQ ID NO:24;
(12) the VH comprises an amino acid sequence of SEQ ID NO:12, and the VL comprises an amino acid sequence of SEQ ID NO:25; or
(13) the VH comprises an amino acid sequence of SEQ ID NO:13, and the VL comprises an amino acid sequence of SEQ ID NO:26.

Embodiment 8 is the isolated antibody or antigen-binding fragment thereof of embodiment 7, wherein the VH comprises the amino acid sequence of SEQ ID NO:12, and the VL comprises the amino acid sequence of SEQ ID NO:25.

Embodiment 9 is the isolated antibody or antigen-binding fragment thereof of embodiment 7, wherein the VH comprises the amino acid sequence of SEQ ID NO:13, and the VL comprises the amino acid sequence of SEQ ID NO:26.

Embodiment 10 is the isolated antibody or antigen-binding fragment thereof of any one of embodiments 1-9, wherein the VH is fused to a heavy chain constant region of an immunoglobulin.

Embodiment 11 is the isolated antibody or antigen-binding fragment thereof of any one of embodiments 1-10, wherein the VL is fused to a light chain constant region (CL) of an immunoglobulin.

Embodiment 12 is the isolated antibody or antigen-binding fragment thereof of any one of embodiments 1-11, wherein the $K_D$ of the binding between the antibody or antigen-binding fragment thereof and the TIGIT is $10^{-7}$ M to about $10^{-12}$ M, preferably about $10^{-8}$ M to about $10^{-12}$ M, more preferably about $10^{-9}$ M to about $10^{-12}$ M.

Embodiment 13 is the isolated antibody or antigen-binding fragment thereof of any one of embodiments 1-12, being rodent, chimeric, human, partially humanized, or fully humanized.

Embodiment 14 is the isolated antibody or antigen-binding fragment thereof of embodiment 13, being humanized.

Embodiment 15 is the isolated antibody or antigen-binding fragment thereof of embodiment 14, wherein the VH comprises the amino acid sequence selected from the group consisting of SEQ ID NOs:105-112, and the VL comprises the amino acid sequence selected from the group consisting of SEQ ID NOs:113-118.

Embodiment 16 is the isolated antibody or antigen-binding fragment thereof of any one of embodiments 1-15, further comprising a second antibody moiety, wherein the second antibody moiety is capable of specifically binding to a second antigen.

Embodiment 17 is the isolated antibody or antigen-binding fragment thereof of embodiment 16, wherein the second antibody moiety is a Fab, a Fab', a (Fab')$_2$, an Fv, a single chain Fv (scFv), an scFv-scFv, a minibody, a diabody, an sdAb, or an antibody mimetic.

Embodiment 18 is the isolated antibody or antigen-binding fragment thereof of embodiment 17, wherein the second antibody moiety is an sdAb.

Embodiment 19 is the isolated antibody or antigen-binding fragment thereof of any one of embodiments 16-18, wherein the second antibody moiety is capable of specifically binding to CTLA-4, preferably, the second antibody moiety is an sdAb capable of specifically binding to CTLA-4.

Embodiment 20 is the isolated antibody or antigen-binding fragment thereof of any one of embodiments 16-18, wherein the second antibody moiety is capable of specifically binding to PD-L1, preferably, the second antibody moiety is an sdAb capable of specifically binding to PD-L1.

Embodiment 21 is the isolated antibody or antigen-binding fragment thereof of any one of embodiments 16-18, wherein the second antibody moiety is capable of specifically binding to TIM-3, preferably, the second antibody moiety is an sdAb capable of specifically binding to TIM-3.

Embodiment 22 is the isolated antibody or antigen-binding fragment thereof of any one of embodiments 16-18, wherein the second antibody moiety is capable of specifically binding to LAG-3, preferably, the second antibody moiety is an sdAb capable of specifically binding to LAG-3.

Embodiment 23 is the isolated antibody or antigen-binding fragment thereof of any one of embodiments 19-22, wherein the amino-terminus of the heavy chain or light chain of a full-length IgG capable of specifically recognizing TIGIT is fused, optionally via a peptide linker, to the carboxyl-terminus of the sdAb capable of specifically binding to CTLA-4, PD-L1, TIM-3, or LAG-3.

Embodiment 24 is the isolated antibody or antigen-binding fragment thereof of any one of embodiments 19-22, wherein the carboxyl-terminus of the heavy chain or light chain or a full-length IgG capable of specifically recognizing TIGIT is fused, optionally via a peptide linker, to the amino-terminus of the sdAb capable of specifically binding to CTLA-4, PD-L1, TIM-3, or LAG-3.

Embodiment 25 is the isolated antibody or antigen-binding fragment thereof of embodiment 23 or 24, wherein the full-length IgG capable of specifically recognizing TIGIT is fused to the sdAb capable of specifically binding to CTLA-4, PD-L1, TIM-3, or LAG-3 via a peptide linker having the amino acid sequence of one of SEQ ID NOs: 119-121.

Embodiment 26 is a second isolated antibody or antigen-binding fragment thereof capable of specifically binding to TIGIT competitively with the isolated antibody or antigen-binding fragment thereof of any one of embodiments 1-25.

Embodiment 27 is a pharmaceutical composition comprising the isolated antibody or antigen-binding fragment thereof of any one of embodiments 1-25 or the second isolated antibody or antigen-binding fragment thereof of embodiment 26, and a pharmaceutically acceptable carrier.

Embodiment 28 is the isolated antibody or antigen-binding fragment thereof of any one of embodiments 1-25, the second isolated antibody or antigen-binding fragment thereof of embodiment 26, or the pharmaceutical composition of embodiment 27, for use in treating a TIGIT related disease in a subject in need thereof.

Embodiment 29 is the isolated antibody or antigen-binding fragment thereof or pharmaceutical composition for use of embodiment 28, wherein the TIGIT related disease is a cancer.

Embodiment 30 is the isolated antibody or antigen-binding fragment thereof or pharmaceutical composition for use of embodiment 29, wherein the cancer is a solid tumor.

Embodiment 31 is the isolated antibody or antigen-binding fragment thereof or pharmaceutical composition for use of embodiment 29, wherein the cancer is a colon cancer.

Embodiment 32 is the isolated antibody or antigen-binding fragment thereof or pharmaceutical composition for use of any one of embodiments 28-31 in combination with an additional cancer therapy.

Embodiment 33 is the isolated antibody or antigen-binding fragment thereof or pharmaceutical composition for use of embodiment 32, wherein the additional cancer therapy is a surgery, radiation, chemotherapy, immunotherapy, hormone therapy, or a combination thereof.

Embodiment 34 is the isolated antibody or antigen-binding fragment thereof or pharmaceutical composition for use of embodiment 28, wherein the TIGIT related disease is a pathogenic infection.

Embodiment 35 is the isolated antibody or antigen-binding fragment thereof or pharmaceutical composition for use of any one of embodiments 28-34, wherein the isolated antibody or antigen-binding fragment or pharmaceutical composition is for systemic or local administration.

Embodiment 36 is the isolated antibody or antigen-binding fragment thereof or pharmaceutical composition for use of any one of embodiments 28-34, wherein the isolated antibody or antigen-binding fragment or pharmaceutical composition is for intravenous administration.

Embodiment 37 is the isolated antibody or antigen-binding fragment thereof or pharmaceutical composition for use of any one of embodiments 28-34, wherein the isolated antibody or antigen-binding fragment or pharmaceutical composition is for intratumoral administration.

Embodiment 38 is the isolated antibody or antigen-binding fragment thereof or pharmaceutical composition for use of any one of embodiments 28-37, wherein the subject is human.

Embodiment 39 is a method of treating a TIGIT-related disease in a subject in need thereof, comprising administering to the subject an effective amount of the pharmaceutical composition of embodiment 27.

Embodiment 40 is the method of embodiment 39, wherein the TIGIT-related disease is cancer.

Embodiment 41 is the method of embodiment 40, wherein the cancer is a solid tumor.

Embodiment 42 is the method of embodiment 40 or 41, wherein the cancer is a colon cancer.

Embodiment 43 is the method of any one of embodiments 40-42, further comprising administering to the individual an additional cancer therapy.

Embodiment 44 is the method of embodiment 43, wherein the additional cancer therapy is surgery, radiation, chemotherapy, immunotherapy, hormone therapy, or a combination thereof.

Embodiment 45 is the method of embodiment 39, wherein the TIGIT-related disease is a pathogenic infection.

Embodiment 46 is the method of any one of embodiments 39-45, wherein the pharmaceutical composition is administered systemically or locally.

Embodiment 47 is the method of any one of embodiments 39-45, wherein the pharmaceutical composition is administered intravenously.

Embodiment 48 is the method of any one of embodiments 39-45, wherein the pharmaceutical composition is administered intratumorally.

Embodiment 49 is the method of any one of embodiments 39-48, wherein the individual is a human.

EXAMPLES

The examples below are intended to be purely exemplary of the invention and should therefore not be considered to limit the invention in any way. The following examples and detailed description are offered by way of illustration and not by way of limitation.

Example 1: Generation of Mouse Anti-Human TIGIT Hybridoma Cell Lines and Monoclonal Antibodies In this disclosure, the mouse anti-human TIGIT monoclonal antibodies, 70A11A8E6, 11D8E12A4, 16F10H12C11, 8F2D8E7, 48B5G4E12, 139E2C2D2, 128E3G7F5, 121C2F10B5, 104G12E12G2, 83G6H11C12, 92E9D4B4, 100C4E7D11, and 64G1E9B4 were obtained through the following immunization methods.

Figure 1B:
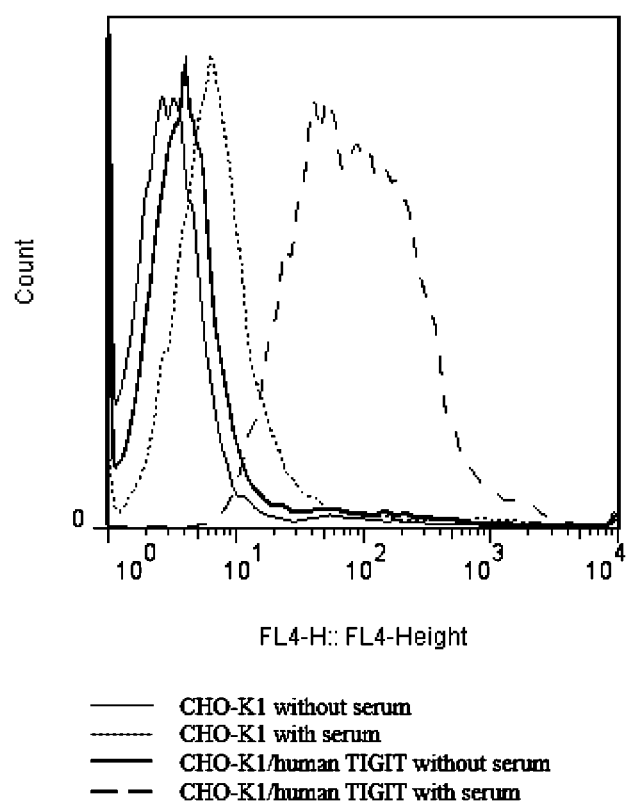
Figure 1C:
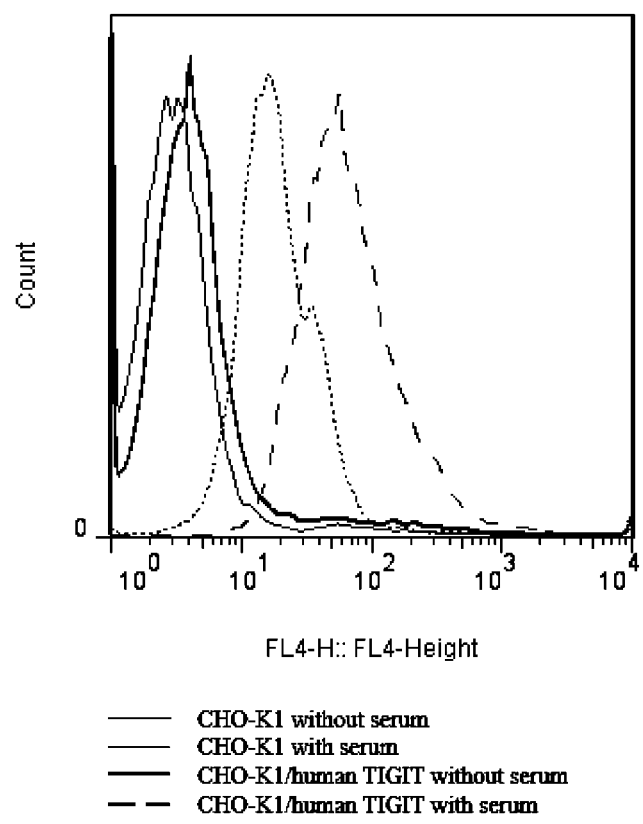
Figure 2A:
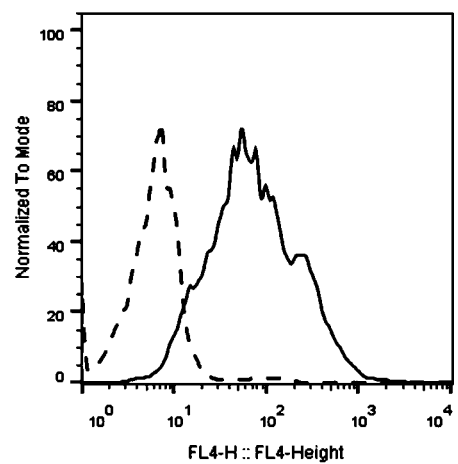
FIGS. 2A-2M depict the bindings of the supernatants from hybridoma subclones on human TIGIT (FIG. 2A: 8F2D8E7.
Figure 2B:
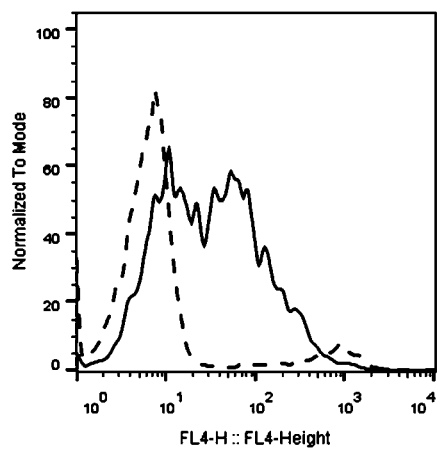
Figure 2C:
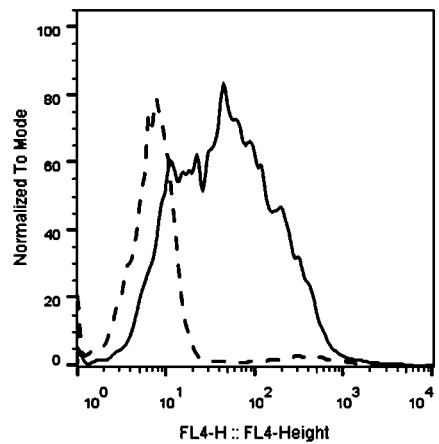
Figure 2D:
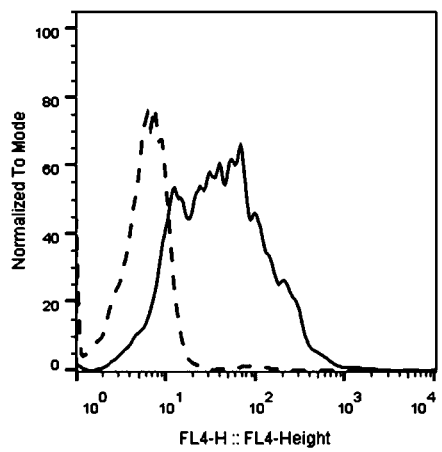
Figure 2E:
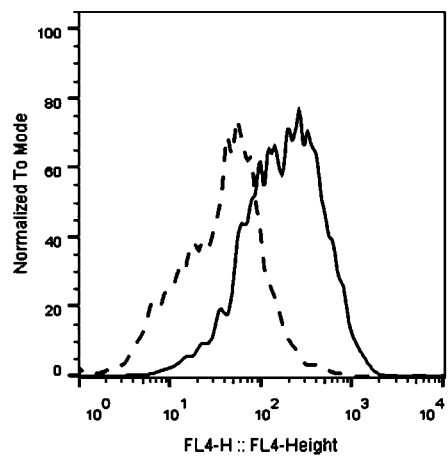
Figure 2F:
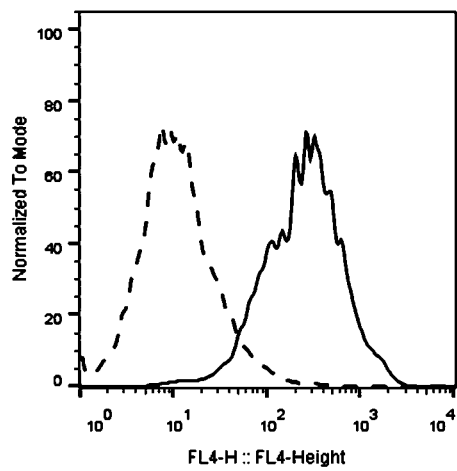
Figure 2G:
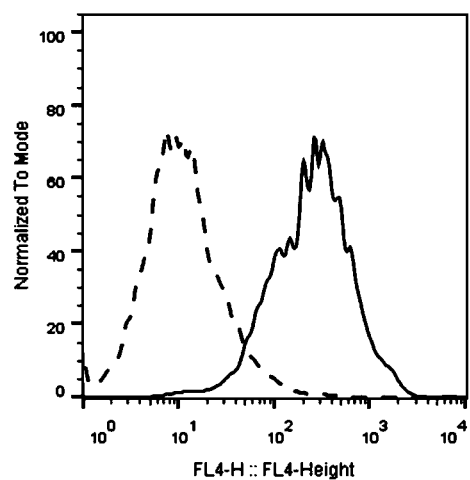
Figure 2H:
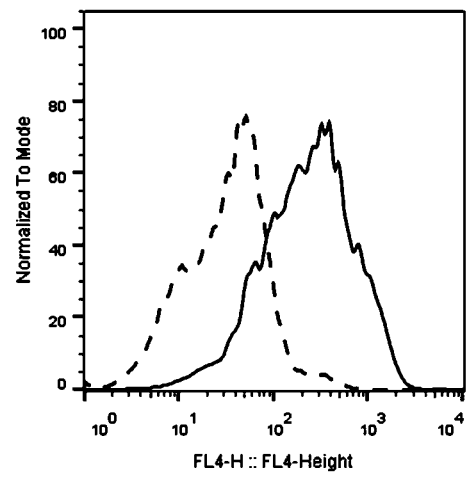
Figure 2I:
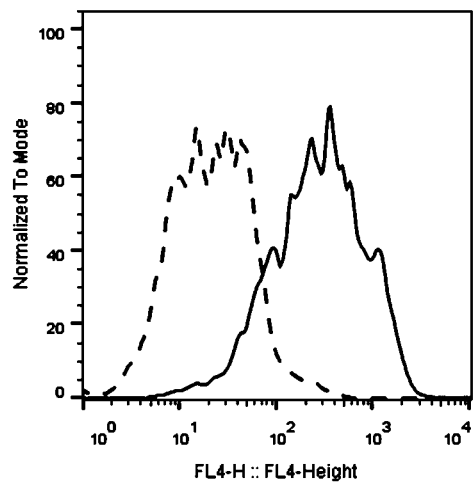
Figure 2J:
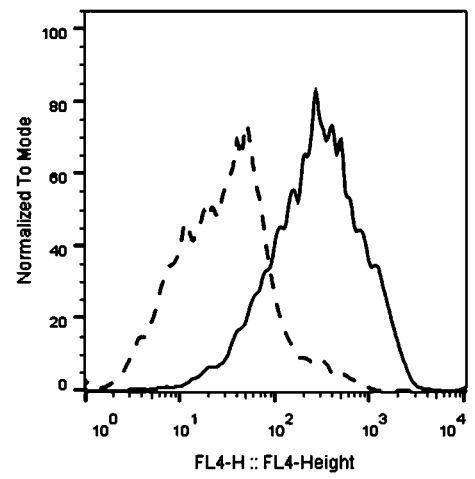
Figure 2K:
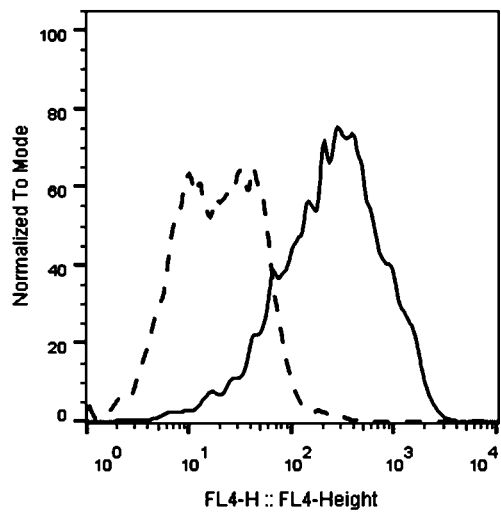
Figure 2L:
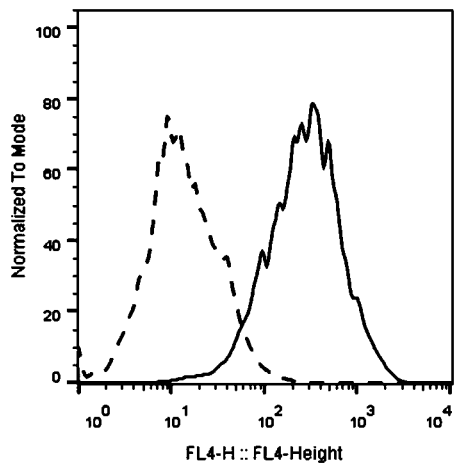
Figure 2M:
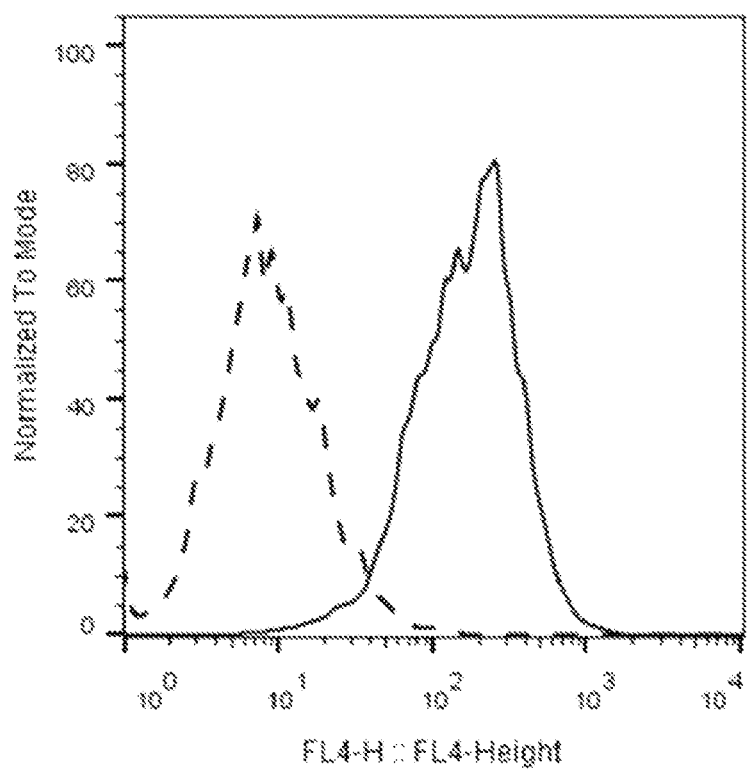

For animal immunization, the immunogen is the fusion protein of Fe tag human TIGIT protein (Acro Bioscience: TIT-5254). 50 μg TIGIT Fc fusion protein were mixed 1:1 with Freud complete adjuvant (Sigma-Aldrich) in 200 μl to immunize female Balb/c mice. Then, mice were boosted intraperitoneally with 25 μg TIGIT Fc fusion protein mixed 1:1 with Freud incomplete adjuvant every two weeks up to 3 times. 4 days before fusion, the three mice (#8087, #8100, and #8771) with high TIGIT binding signal in a flow cytometry study by fluorescence-activated cell sorting (FACS, FIGS. 1A-1C) were selected for final boost with 25 μg TIGIT Fc fusion protein (no adjuvant) intraperitoneally. FACS binding tests were applied to evaluate the binding ability of the antibodies in hybridoma supernatants to TIGIT protein expressed on the surface of CHO-K1 cells (GenScript). Both CHO-K1 parental cells and CHO-K1 overexpressed with human TIGIT were collected and washed with PBS three times. $2.5 \times 10^5$ cells and 100 hybridoma supernatants were added into each well of 96-well plates to incubate at 4° C. for 1 hour. Then the plates were washed 3 times using PBS. 100 μl iFluor labeled goat anti-mouse IgG was added and incubated at 4° C. for 45 min. Finally, the cells were washed 3 times with PBS, and the signal was read out by FACS BD Calibur.

For hybridoma fusion and screening, isolated spleens were made into homogenized single cell suspension, and the single cell suspensions were also made for the myeloma cells (SP 2/0 cells). $8.9 \times 10^7$ spleen cell and $4.1 \times 10^7$ SP 2/0 cells were fusion through electrofusion method. The fused cells from each hybridoma fusion were re-suspend in 100 ml DMEM/10% FBS medium containing thymus nucleoside pyrimidine, hypoxanthine and aminopterin hybridoma selective reagent. The cell suspension was distributed 100 each into fifty 96 wells. The 96 well plates were cultured in 37° C. incubator with 6% $CO_2$ concentration for 7 days. Then the hybridoma supernatants were tested by ELISA binding, blocking and FACS binding to detect the existence of the anti-human TIGIT antibody by ELISA binding test.

ELISA binding tests: indirect ELISA was applied to access the binding ability of the antibodies in supernatants to human TIGIT Fc fusion protein. 0.5 μg/ml recombinant TIGIT Fc fusion protein or human IgG1 was coated in ELISA Plate with 100 in PBS per well at 4° C. overnight. PBST (0.05% tween) were used to wash the plate. PBST containing 1% BSA was used to block the plate in 2001 per well for 0.5 hour. The blocking buffer was discarded later and hybridoma supernatants were added in 100 per well to incubate at room temperature for 1 hour. The plates were then washed with PBST for 3 times. Goat anti-mouse IgG (Fab specific) HRP were added in 100 μl per well and incubated at 37° C. for half hour. The plates were then washed with PBST 5 times, and TMB buffer (GenScript) were added into the well and incubated at room temperature for 15 min. 1M HCL (Sigma) stopping buffer was added at 50 μl per well to stop the reaction and the plates were read at 450 nm.

The hybridoma with the OD value difference between the reading from its supernatant ELISA test on human TIGIT Fc fusion protein and human IgG1 over 500 was selected for further hybridoma subcloning. The subcloning was performed by limited dilution. The cells were counted and serial diluted in DMEM/10% FBS medium containing thymus nucleoside pyrimidine, hypoxanthine and aminopterin hybridoma selective reagent to a concentration of 5-15 cells per ml. For each hybridoma clone, 200 hybridoma suspension was transferred into 96 wells at a concentration of 1-3 cells per well. The plates were incubated at 37° C. with 5% $CO_2$ for 1 week. And the supernatants were then used in FACS binding study to evaluate the existence of the anti-human TIGIT antibodies. The hybridoma supernatants from 70A11A8E6, 11D8E12A4, 16F10H12C11, 8F2D8E7, 48B5G4E12, 139E2C2D2, 128E3G7F5, 121C2F10B5, 104G12E12G2, 83G6H11C12, 92E9D4B4, 100C4E7D11, and 64G1E9B4 were confirmed to bind human TIGIT with specificity by a FACS study (FIGS. 2A-2M).

Example 2: Sequencing and Expression of Mouse Anti-Human TIGIT Hybridoma Cell Lines and Monoclonal Antibodies The express mouse isotype ELISA kit (Clonotyping System-HRP, SouthernBiotech; Birmingham, Ala.) was used to identify the isotype of the monoclonal antibodies. TRIzol (Ambion) was then used to extract total RNA of the monoclones from $3 \times 10^6$-$5 \times 10^6$ of the hybridoma cells. Isotype specific primer and universal primer (PrimeScript™ 1stStrand cDNA Synthesis Kit, Takara; Mountain View, Calif.) were used to reverse transcribe the RNA into cDNA, then RACE PCR (GenScript) was applied to amplify the variable region of the antibody heavy chain and light chain, and PCR products were subcloned into the pMD18-T vector system (Takara). Vector specific primers were used to validate and sequence of the inserted segment. Finally, variable region DNA/protein sequence of 70A11A8E6, 11D8E12A4, 16F10H12C11, 8F2D8E7, 48B5G4E12, 139E2C2D2, 128E3G7F5, 121C2F10B5, 104G12E12G2, 83G6H11C12, 92E9D4B4, 100C4E7D11, and 64G1E9B4 was obtained.

DNA fragments of heavy chain or light chain variable and constant regions from each of above clones were synthesized and inserted into pTT5 expression vectors. The constructed plasmids were used to transfect HEK293-6E cells, and the HEK293-6E cells were cultured in shaking flasks at 37° C. for 10 days. The supernatants were then collected for purification. Before purification, the pipes and protein A columns were treated with 0.2M NaOH to remove pyrogen. Then, the columns were re-balanced with 0.05M Tris and 1.5M NaCl (pH 8.0). The supernatants collected before were mixed 1:1 with the balance buffer and filtered to keep sterile. The filtered supernatants were incubated with the protein A column at room temperature for 2 hours, and washed with the 1× balance buffer. The IgGs were eluted with sterile 0.1M sodium citrate (pH 3.5). The elution solution was neutralized with 1/9 volume of the 1M Tris-HCl (pH 9.0). The neutralized solution was changed into PBS (pH 7.4) buffer to remove other buffer contents and the final sample solution was concentrated under aseptic conditions. The concentration was then determined through OD280 nm with 1.43 extinction coefficient Ec (0.1%). The purified antibodies were tested by SDS-PAGE using a 10% pre-made gel (GenScript) on a BioRad electrophoresis system. The gel was stained with Estain 2.0 (GenScript) and the purity and molecular weight were estimated by comparing with the protein ladder (GenScript).

Example 3: Binding of the Mouse Anti-Human TIGIT Monoclonal Antibodies to Human TIGIT Recombinant Protein Binding kinetics of mouse anti-human TIGIT monoclonal antibodies to human TIGIT were determined using a Surface Plasmon Resonance (SPR) biosensor, BIACORE® T200 (GE Healthcare; Little Chalfont, United Kingdom). Different concentrations of the mouse anti-human TIGIT monoclonal antibodies were prepared starting at 50 nM with 3-fold serial dilution. Each mouse anti-human TIGIT monoclonal antibody was immobilized on the sensor chip through the Fc capture method. Human TIGIT protein with HIS tag was used as the analyte. The dissociation ($k_d$) and association ($k_a$) rate constants were obtained using the BIACORE® T200 evaluation software. The apparent equilibrium dissociation constants ($K_D$) were calculated from the ratio of $k_d$ over $k_a$. As shown in Table 3, the mouse anti-human TIGIT monoclonal antibodies had comparable binding kinetics to human TIGIT protein (Table 3).

TABLE 3

Binding of mouse anti-human TIGIT monoclonal antibodies on human TIGIT

| Antibody | ka (1/Ms) | kd (1/s) | KD (M) | Rmax (RU) | Chi$^2$ (RU$^2$) |
| --- | --- | --- | --- | --- | --- |
| 70A11A8E6 | 8.6E+05 | 4.4E−03 | 5.2E−09 | 56.5 | 0.306 |
| 11D8E12A4 | 6.4E+05 | 8.7E−03 | 1.4E−08 | 15.6 | 1.34 |
| 16F10H12C11 | 6.7E+07 | 1.2E+00 | 1.8E−08 | 35.1 | 1.91 |
| 8F2D8E7 | 1.3E+06 | 3.3E−03 | 2.6E−09 | 53.9 | 1.16 |
| 48B5G4E12 | 8.4E+05 | 8.8E−03 | 1.1E−08 | 78.3 | 3.19 |
| 139E2C2D2 | 2.1E+06 | 6.2E−03 | 3.0E−09 | 43.5 | 0.116 |
| 128E3G7F5 | 1.2E+06 | 8.0E−03 | 6.7E−09 | 52.8 | 0.198 |
| 121C2F10B5 | 1.3E+06 | 9.3E−04 | 7.2E−10 | 57.3 | 2.82 |
| 104G12E12G2 | 3.7E+05 | 8.3E−04 | 2.3E−09 | 48.4 | 0.104 |
| 83G6H11C12 | 6.1E+05 | 4.3E−04 | 7.0E−10 | 59.6 | 0.457 |
| 92E9D4B4 | 7.1E+05 | 4.1E−04 | 5.7E−10 | 53.3 | 0.362 |
| 100C4E7D11 | 6.5E+05 | 3.3E−04 | 5.1E−10 | 50.7 | 0.412 |
| 64G1E9B4 | 6.5E+05 | 1.5E−04 | 2.3E−10 | 54 | 0.174 |

Figure 3A:
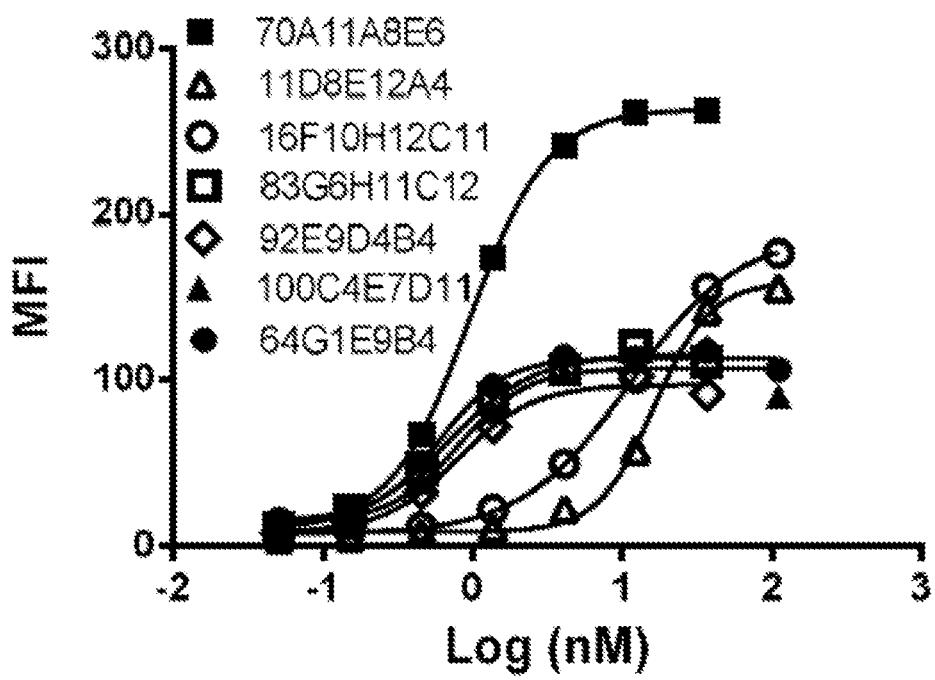
FIGS. 3A-3C depict the binding of the mouse anti-human TIGIT monoclonal antibodies to human or cynomolgus TIGIT expressed in CHO-K1 cells. The binding to human TIGIT was shown in FIG. 3A and FIG. 3B. The binding to cynomolgus TIGIT was shown in FIG. 3C.
Figure 3B:
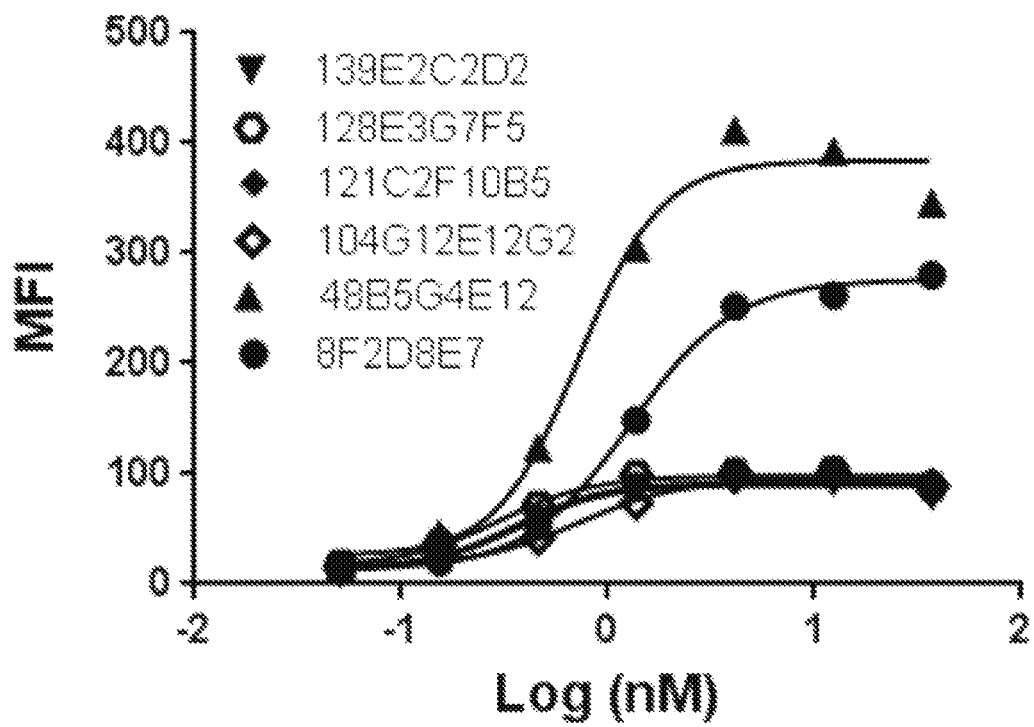
Figure 3C:
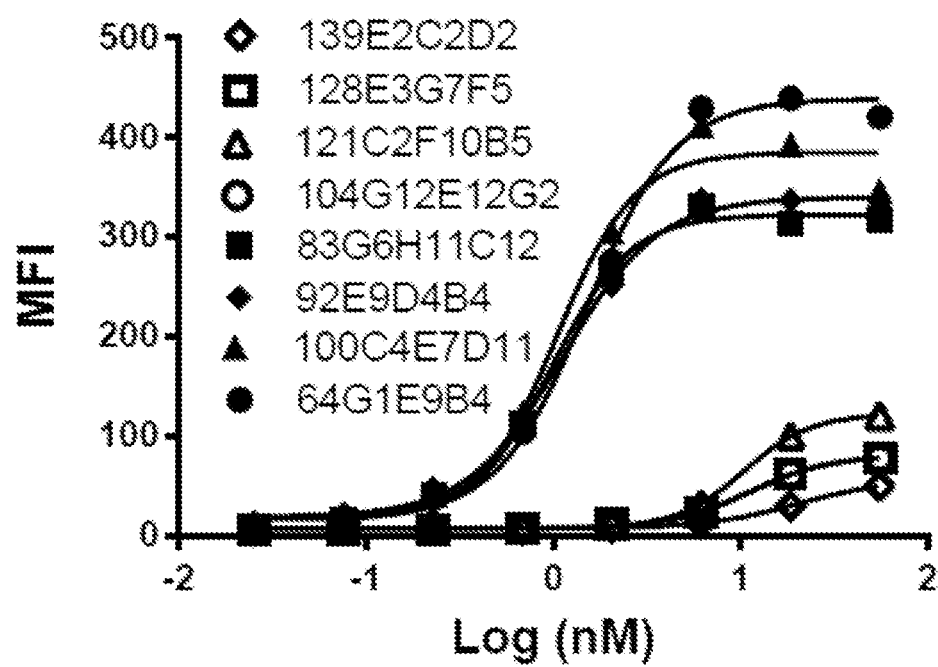

Example 4: Binding of the Mouse Anti-Human TIGIT Monoclonal Antibodies to Human or Cynomolgus TIGIT Expressed in CHO-K1 Cells Binding affinities of the mouse anti-human TIGIT monoclonal antibodies to human or cynomolgus TIGIT overexpressed on CHO-KI cells were determined using a fluorescence-activated cell sorting (FACS)-based assay. The mouse anti-human TIGIT monoclonal antibodies were prepared (starting at 111 µM for human TIGIT and 55.6 µM for cynomolgus TIGIT, 3-fold serial dilution with 9 concentrations) as primary antibodies for FACS analysis. CHO-K1 cells expressing human TIGIT were dissociated from adherent culture flasks and mixed with varying concentrations of the mouse anti-human TIGIT monoclonal antibodies (both in a 96-well plate). The mixture was equilibrated for 30 minutes at room temperature and washed three times with FACS buffer (PBS containing 1% BSA). iFluor labeled goat anti-mouse IgG as the secondary antibody was added and incubated at room temperature for 45 min. Finally, the cells were washed 3 time with PBS, and the signal was read by FACS BD Calibur. Data was analyzed with PRISM™ (GraphPad Software, San Diego, Calif.) using non-linear regression and $EC_{50}$ values were calculated. As shown in FIGS. 3A-3C and Table 4, the FACS study demonstrated that the mouse anti-human TIGIT monoclonal antibodies bound to human TIGIT over-expressed in CHO-K1 cells with $EC_{50}$ values ranging from 0.3 nM to 16.3 nM.

TABLE 4

Anti-human TIGIT monoclonal antibodies binding on CHO-K1/human TIGIT cells

| Antibody | Best-fit values | | |
| --- | --- | --- | --- |
| | Bottom | Top | $EC_{50}$ (nM) |
| 70A11A8E6 | 11.02 | 263.2 | 0.96 |
| 11D8E12A4 | 8.30 | 158.8 | 16.32 |
| 16F10H12C11 | 6.83 | 188.2 | 11.25 |
| 8F2D8E7 | 12.92 | 276.2 | 1.28 |
| 48B5G4E12 | 9.18 | 346.1 | 3.15 |
| 139E2C2D2 | 13.78 | 89.9 | 0.37 |
| 128E3G7F5 | 16.18 | 98.7 | 0.30 |
| 121C2F10B5 | 14.16 | 92.7 | 0.36 |
| 104G12E12G2 | 15.49 | 96.9 | 0.73 |
| 83G6H11C12 | 9.57 | 115.4 | 0.68 |

TABLE 4-continued

Anti-human TIGIT monoclonal antibodies
binding on CHO-K1/human TIGIT cells

| Antibody | Best-fit values | | |
|---|---|---|---|
| | Bottom | Top | EC$_{50}$ (nM) |
| 92E9D4B4 | 7.99 | 97.0 | 0.80 |
| 100C4E7D11 | 13.97 | 107.0 | 0.81 |
| 64G1E9B4 | 15.32 | 112.9 | 0.61 |

Among the mouse anti-human TIGIT monoclonal antibodies tested, only 139E2C2D2, 128E3G7F5, 121C2F10B5, 104G12E12G2, 83G6H11C12, 92E9D4B4, 100C4E7D11, and 64G1E9B4 bound to cynomolgus TIGIT. As shown in FIGS. 3A-3C and Table 5, the FACS study demonstrated that some of the mouse anti-human TIGIT monoclonal antibodies bound to cynomolgus TIGIT over-expressed in CHO-K1 cells with EC$_{50}$ values range 1 nM to 18.5 nM.

TABLE 5

Anti-human TIGIT monoclonal antibodies binding
on CHO-K1/cynomolgus TIGIT cells

| Antibody | Best-fit values | | |
|---|---|---|---|
| | Bottom | Top | EC$_{50}$ (nM) |
| 139E2C2D2 | 7.6 | 53.8 | 18.54 |
| 128E3G7F5 | 7.5 | 66.2 | 8.38 |
| 121C2F10B5 | 7.6 | 120.5 | 10.24 |
| 104G12E12G2 | 7.0 | 80.6 | 11.12 |
| 83G6H11C12 | 16.1 | 325.6 | 1.00 |
| 92E9D4B4 | 17.7 | 348.0 | 1.16 |
| 100C4E7D11 | 16.9 | 410.2 | 1.16 |
| 64G1E9B4 | 15.3 | 455.1 | 1.58 |

Figure 4A:
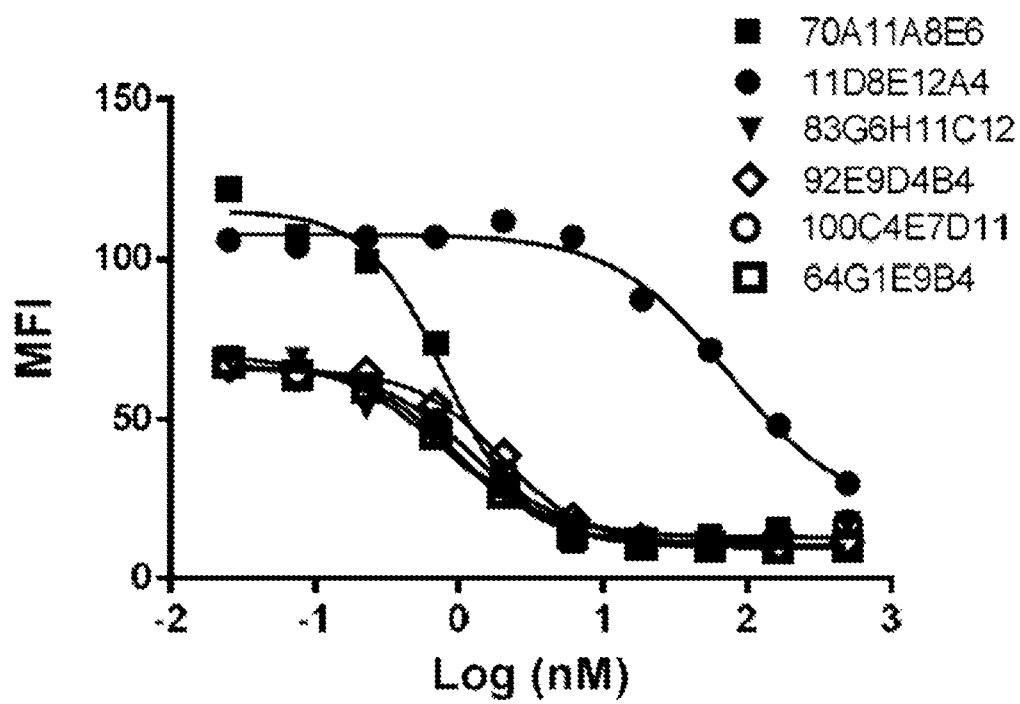
FIGS. 4A-4B depict the competitive binding on human TIGIT between the mouse anti-human TIGIT monoclonal antibodies and PVR recombinant protein.
Figure 4B:
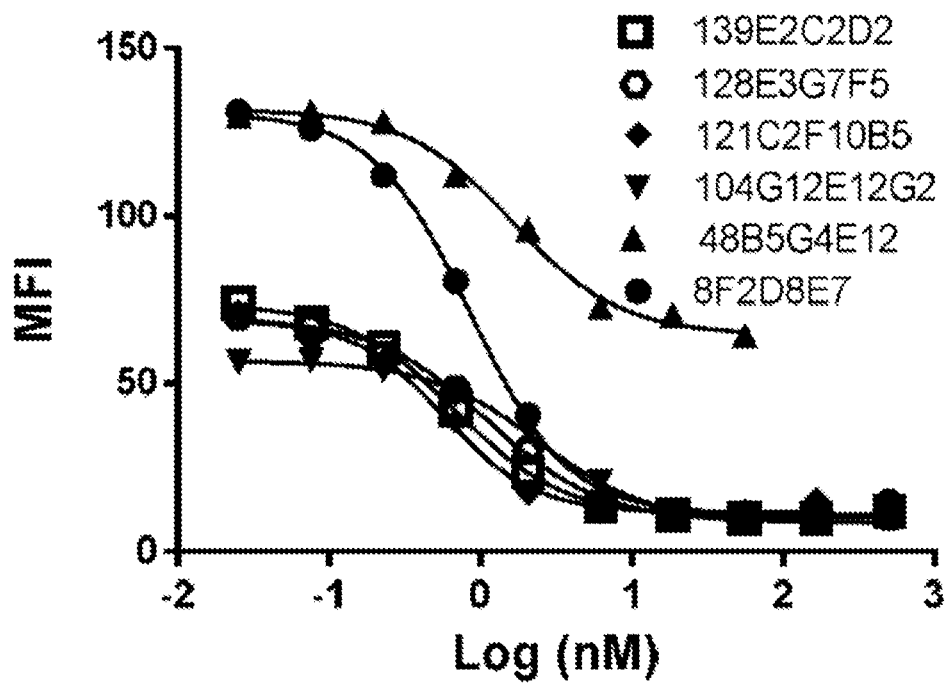

Example 5: The Competitive Binding on Human TIGIT Over-Expressed in CHO-K1 Cells Between the Mouse Anti-Human TIGIT Monoclonal Antibodies and PVR Recombinant Protein The competitive binding on human TIGIT between the mouse anti-human TIGIT monoclonal antibodies and PVR recombinant protein was assessed using a FACS assay. To assess the competitive binding on human TIGIT between the mouse anti-human TIGIT monoclonal antibodies and PVR, the mouse anti-human TIGIT monoclonal antibody samples were prepared (starting at 500 nM, 3-fold serial dilution with 10 concentrations). CHO cells expressing human TIGIT were dissociated from adherent culture flasks and mixed with varying concentrations of each mouse anti-human TIGIT monoclonal antibody and 5 μg/ml human TIGIT-Fc fusion protein having a biotin label. The mixture was equilibrated for 30 minutes at room temperature, and washed three times with FACS buffer (PBS containing 1% BSA). PE/Cy5 Streptavidin secondary antibody was then added to the mixtures and incubated for 15 minutes at room temperature. Subsequently, the cells were washed with FACS buffer and analyzed by flow cytometry. Data was analyzed with PRISM™ (GraphPad Software, San Diego, Calif.) using non-linear regression, and IC$_{50}$ values were calculated (FIGS. 4A-4B and Table 6). The competition FACS study demonstrated the ability of the mouse anti-human TIGIT monoclonal antibodies to block the binding between human TIGIT and human PVR with IC$_{50}$ values range from 0.6 nM to 73.5 nM, except for 16F10H12C11.

TABLE 6

Anti-human TIGIT monoclonal antibodies'
blocking on binding of TIGIT/PVR

| Antibody | Best-fit values | | |
|---|---|---|---|
| | Bottom | Top | IC$_{50}$ (nM) |
| 70A11A8E6 | 19.6 | 113.4 | 0.7 |
| 11D8E12A4 | 21.2 | 107.9 | 73.5 |
| 16F10H12C11 | | N.A | |
| 8F2D8E7 | 11.2 | 130.6 | 0.9 |
| 48B5G4E12 | 64.6 | 131.7 | 1.6 |
| 139E2C2D2 | 10.4 | 73.8 | 0.7 |
| 128E3G7F5 | 8.8 | 69.7 | 1.1 |
| 121C2F10B5 | 11.8 | 68.8 | 0.6 |
| 104G12E12G2 | 8.9 | 56.9 | 2.4 |
| 83G6H11C12 | 12.9 | 70.2 | 0.7 |
| 92E9D4B4 | 10.3 | 65.5 | 2.0 |
| 100C4E7D11 | 12.9 | 66.5 | 1.2 |
| 64G1E9B4 | 9.5 | 67.1 | 1.0 |

Example 6: Epitope Binding of the Mouse Anti-Human TIGIT Monoclonal Antibodies Against Human TIGIT An epitope binding test on 128E3G7F5, 121C2F10B5, 104G12E12G2, 83G6H11C12, 92E9D4B4, 100C4E7D11, and 64G1E9B4 was performed on an Octet RED96 instrument (ForteBio; Menlo Park, Calif.). All measurements were performed at 30° C. One antibody of interest was immobilized onto the biosensors using amine coupling method. The antigen protein TIGIT was diluted in PBST buffer (1x PBS, pH 7.4, and 0.05% Tween-20) as used as analyte 1. The mixture of antigen protein TIGIT (concentration same as in analyte 1) and the second antibody was used as analyte 2. The coated biosensors were first dipped into analyte 1 and then dipped into analyte 2 after regeneration and equilibration. The sensorgrams of analyte 1 and analyte 2 were compared. If the binding level of analyte 1 is significantly higher than that of analyte 2, the second antibody was considered to be able to compete with the immobilized antibody for binding the target protein TIGIT. If the binding level of analyte 1 is significantly lower than that of analyte 2, the second antibody was considered not able to compete with the immobilized antibody for binding the target protein TIGIT. The experiment was repeated until all the antibodies were analyzed. 128E3G7F5, 121C2F10B5, 104G12E12G2, 83G6H11C12, 92E9D4B4, 100C4E7D11, and 64G1E9B4 were mapped into three groups (Table 7). The mouse anti-human TIGIT monoclonal antibodies in each group have the closely related or same epitope on human TIGIT.

TABLE 7

Epitope binding of the mouse anti-human
TIGIT antibodies against human TIGIT

| Antibody ID | Group |
|---|---|
| 64G1E9B4 | I |
| 100C4E7D11 | II |
| 83G6H11C12 | II |
| 92E9D4B4 | II |
| 104G12E12G2 | I |
| 121C2F10B5 | III |
| 128E3G7F5 | III |

Figure 5A:
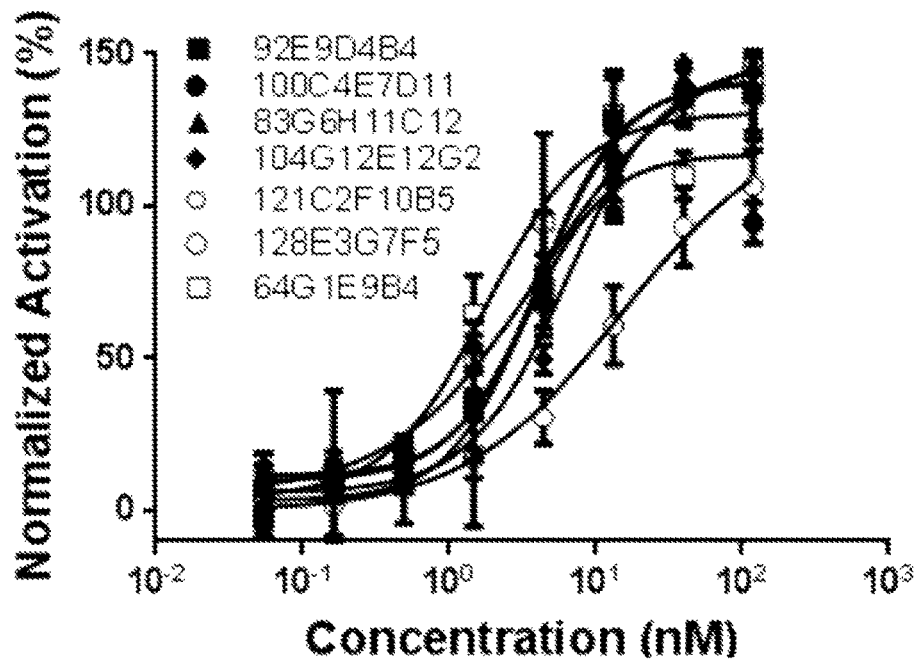
FIGS. 5A-5B depict the neutralization effects of the mouse anti-human TIGIT antibodies on T cell activations inhibited by binding of PVR on TIGIT overexpressed in T cells. The T cell activation indicated by luciferase reporter signal was shown in FIG. 5A and the T cell activation indicated by IL-2 secretion was shown in FIG. 5B.
Figure 5B:
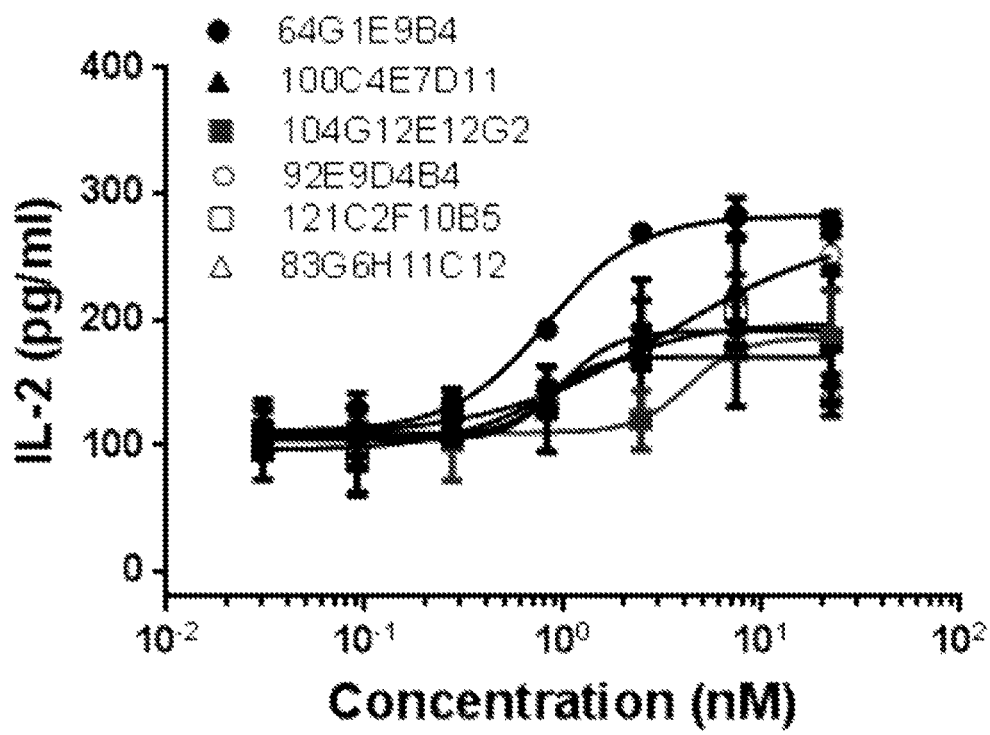

Example 7: The Neutralization Effects of the Mouse Anti-Human TIGIT Antibodies on T Cell Activations Inhibited by Binding of PVR on TIGIT Overexpressed in T Cells CHO-K1 cells were engineered to be the artificial dendritic cells (APC) by stably transfecting a T cell receptor (TCR) activator. CHO-K1 APC was then overexpressed with PVR. The Jurkat cell line was stably transfected with an NFAT-inducible Lucia reporter construct to generate a Jurkat/NFAT reporter cell line. The Jurkat/NFAT reporter cell line was then overexpressed with human TIGIT. The CHO-K1 APC/PVR cells were co-cultured with the Jurkat/NFAT reporter/TIGIT cells to evaluate the neutralization activities of the mouse anti-human TIGIT monoclonal antibodies. The Jurkat/NFAT reporter/TIGIT cells were pre-incubated with serial dilution of each mouse anti-human TIGIT monoclonal antibodies for 30 minutes before adding the CHO-K1 APC/PVR cells. After a couple hours of interaction, 20 µl of supernatant were collected from each well for IL-2 measurement and then ONE-STEP™ Luciferase reagent was added to the system for measuring the NFAT activity. The activation of Jurkat/NFAT reporter/TIGIT cells was evaluated by the intensity of luciferase signal or the secretion of IL-2. The binding of PVR on TIGIT between two cells inhibited Jurkat/NFAT reporter/TIGIT cells activation. The mouse anti-human TIGIT monoclonal antibodies blocked the interaction between PVR and TIGIT, and then neutralized the inhibition of PVR on TIGIT. The more neutralization antibody was added, the more Jurkat/NFAT reporter/TIGIT cells were activated, the more luciferase signal or the more IL-2 was secreted (FIGS. 5A-5B, Table 8, and Table 9). Data was analyzed with PRISM™ (GraphPad Software, San Diego, Calif.) using non-linear regression, and $EC_{50}$ values were calculated on both normalized luciferase signal and IL-2 secretion.

TABLE 8

The mouse anti-human TIGIT antibodies on luciferase signal in T cell activations

| Antibody | Best-fit values | | |
|---|---|---|---|
| | Bottom | Top | $EC_{50}$ (nM) |
| 64G1E9B4 | 5.7 | 124.2 | 1.64 |
| 100C4E7D11 | 11.6 | 117.0 | 3.46 |
| 83G6H11C12 | 9.6 | 145.0 | 4.40 |
| 92E9D4B4 | 3.4 | 140.7 | 3.90 |
| 104G12E12G2 | 6.0 | 147.0 | 6.42 |
| 121C2F10B5 | 5.4 | 152.7 | 4.38 |
| 128E3G7F5 | 4.5 | 99.0 | 8.54 |

TABLE 9

The mouse anti-human TIGIT antibodies on IL-2 secretion in T cell activations

| Antibody | Best-fit values | | |
|---|---|---|---|
| | Bottom | Top | $EC_{50}$ (nM) |
| 64G1E9B4 | 111.4 | 282.6 | 0.82 |
| 100C4E7D11 | 107.1 | 191.4 | 0.98 |
| 83G6H11C12 | 104.3 | 170.7 | 0.83 |
| 92E9D4B4 | 106.1 | 274.1 | 3.36 |
| 104G12E12G2 | 108.2 | 189.2 | 3.31 |
| 121C2F10B5 | 96.18 | 197.2 | 1.02 |

Example 8: Binding of the Chimeric Anti-Human TIGIT Monoclonal Antibodies or Humanized Anti-Human TIGIT Monoclonal Antibodies to Human TIGIT Recombinant Protein The chimeric anti-human TIGIT monoclonal antibodies (100C4E7D11 chimeric or 64G1E9B4 chimeric) were made by fusing variable domains of the heavy and light chains of 100C4E7D11 or 64G1E9B4 with the constant region of human IgG1.

The humanized anti-human TIGIT monoclonal antibody (100C4E7D11VH1_VL1) of 100C4E7D11 was made by fusing the humanized variable domains of the heavy chain (SEQ ID NO: 105) and light chain (SEQ ID NO: 113) of 100C4E7D11 with the constant region of human IgG1.

The humanized anti-human TIGIT monoclonal antibody (64G1E9B4VH1_VL1.M1) of 64G1E9B4 was made by fusing the humanized variable domains of the heavy chain (SEQ ID NO: 109) and light chain (SEQ ID NO: 118) of 64G1E9B4 with the constant region of human IgG1. The humanized 64G1E9B4VH1VL1.M1 monoclonal antibody comprises one amino acid substitution in the light chain CDR of SEQ ID NO: 78, wherein the substitution is made at position 1K, and wherein residue 1K is substituted to R (VL: SEQ ID NO: 135; VL CDR1: SEQ ID NO: 131).

The humanized anti-human TIGIT monoclonal antibody (64G1E9B4VH1.M1_VL1.M1) of 64G1E9B4 was made by fusing the humanized variable domains of the heavy chain (SEQ ID NO: 109) and light chain (SEQ ID NO:118) of 64G1E9B4 with the constant region of human IgG1. The humanized 64G1E9B4VH1.M1_VL1.M1 monoclonal antibody comprises one amino acid substitution in the heavy chain CDR of SEQ ID NO:52, wherein the substitution is made at position 7D, and wherein residue 7D is substituted to G (VH: SEQ ID NO: 134; VH CDR2: SEQ ID NO: 128). It also comprises one amino acid substitution in the light chain CDR of SEQ ID NO: 78, wherein the substitution is made at position 1K, and wherein residue 1K is substituted to R (VL: SEQ ID NO: 135;VL CDR1:SEQ ID NO: 131).

Binding kinetics of the chimeric anti-human TIGIT monoclonal antibodies and the humanized anti-human TIGIT monoclonal antibodies to human TIGIT were determined using a Surface Plasmon Resonance (SPR) biosensor, BIACORE® T200 (GE Healthcare). Different concentrations of the chimeric anti-human TIGIT monoclonal antibodies or humanized anti-human TIGIT monoclonal antibodies were prepared starting at 50 nM with a 3-fold serial dilution. Each chimeric anti-human TIGIT monoclonal antibody or each humanized anti-human TIGIT monoclonal antibody was immobilized on the sensor chip through the Fc capture method. Human TIGIT protein with a HIS tag was used as the analyte. The dissociation ($k_d$) and association ($k_a$) rate constants were obtained using the BIACORE® T200 evaluation software. The apparent equilibrium dissociation constants ($K_D$) were calculated from the ratio of $k_d$ over $k_a$. As shown in Table 10, the chimeric anti-human TIGIT monoclonal antibodies and the humanized anti-human TIGIT monoclonal antibodies had comparable binding kinetics to human TIGIT protein (Table 10).

TABLE 10

Binding of chimeric or humanized anti-human TIGIT antibodies on human TIGIT

| Antibody | $k_a$ (1/Ms) | $k_d$ (1/s) | $K_D$ (M) | Rmax (RU) | Chi$^2$ (RU$^2$) |
|---|---|---|---|---|---|
| 64G1 Chimeric | 9.10E+05 | 6.40E−05 | 7.00E−11 | 31.36 | 0.037 |
| 64G1VH1_VL1.M1 | 5.90E+05 | 8.80E−05 | 1.50E−10 | 45.42 | 0.038 |
| 64G1VH1.M1_VL1.M1 | 6.30E+05 | 1.00E−04 | 1.70E−10 | 40.16 | 0.041 |
| 100C4 Chimeric | 9.10E+05 | 1.60E−04 | 1.70E−10 | 39.53 | 0.098 |
| 100C4VH1_VL1 | 6.10E+05 | 3.50E−04 | 5.70E−10 | 34.68 | 0.092 |

Figure 6A:
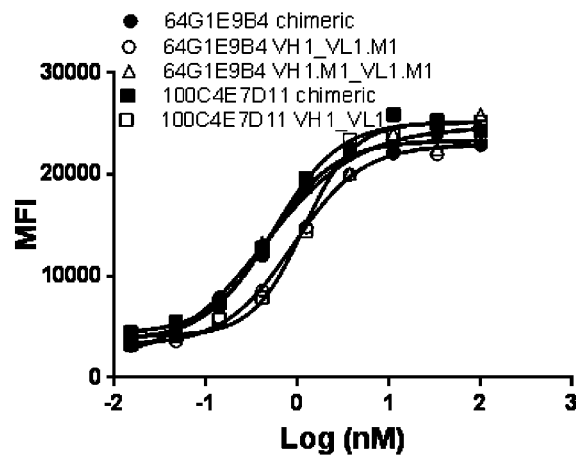
FIGS. 6A-6B depict the binding of the chimeric anti-human TIGIT monoclonal antibodies or the humanized anti-human TIGIT monoclonal antibodies to human or cynomolgus TIGIT expressed in CHO-K1 cells. The binding to human TIGIT was shown in FIG. 6A and the binding to cynomolgus TIGIT was shown in FIG. 6B.

Example 9: Binding of the Chimeric Anti-Human TIGIT Monoclonal Antibodies and the Humanized Anti-Human TIGIT Monoclonal Antibodies to Human or Cynomolgus TIGIT Expressed in CHO-K1 Cells Binding affinities of the chimeric anti-human TIGIT monoclonal antibodies and the humanized anti-human TIGIT monoclonal antibodies to human or cynomolgus TIGIT over-expressed on CHO-K1 cells were determined using a fluorescence-activated cell sorting (FACS)-based assay. The chimeric anti-human TIGIT monoclonal antibodies and the humanized anti-human TIGIT monoclonal antibodies were prepared (starting at 100 µM for human TIGIT and 55.6 µM for cynomolgus TIGIT, 3-fold serial dilution with 10 concentrations) as primary antibodies for FACS analysis. CHO-K1 cells expressing human TIGIT were dissociated from adherent culture flasks and mixed with varying concentrations of the mouse anti-human TIGIT monoclonal antibodies (both in a 96-well plate). The mixture was equilibrated for 30 minutes at room temperature and washed three times with FACS buffer (PBS containing 1% BSA). iFluor labeled goat anti-mouse IgG as the secondary antibody was added and incubated at room temperature for 45 min. Finally, the cells were washed 3 time with PBS, and the signal was read by FACS BD Calibur. Data was analyzed with PRISM™ (GraphPad Software, San Diego, Calif.) using non-linear regression and EC$_{50}$ values were calculated. As shown in FIG. 6A and Table 11, the FACS study demonstrated that the chimeric anti-human TIGIT monoclonal antibodies and the humanized anti-human TIGIT monoclonal antibodies bound to human TIGIT over-expressed in CHO-K1 cells with EC$_{50}$ values ranging from 0.4 nM to 1.2 nM.

TABLE 11

Anti-human TIGIT monoclonal antibodies binding on CHO-K1/human TIGIT cells

| | Best-fit values | | |
|---|---|---|---|
| Antibody | Bottom | Top | EC$_{50}$ (nM) |
| 64G1E9B4 VH1_VL1.M1 | 3194 | 22935 | 0.89 |
| 64G1E9B4 VH1.M1_VL1.M1 | 1532 | 24690 | 0.43 |
| 100C4E7D11 VH1_VL1 | 4108 | 25171 | 1.15 |
| 64G1E9B4 chimeric | 3595 | 23371 | 0.47 |
| 100C4E7D11 chimeric | 4163 | 25618 | 0.58 |

Figure 6B:
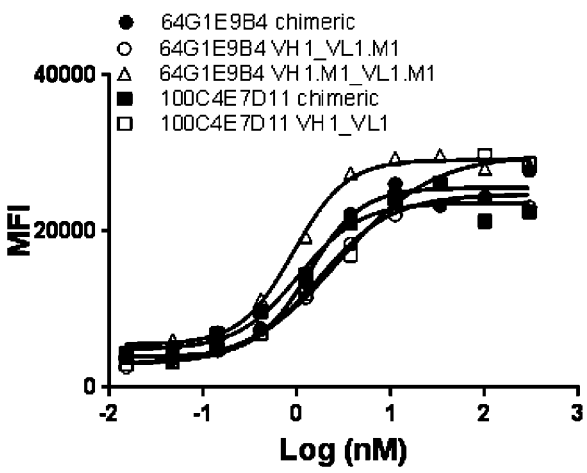

The chimeric anti-human TIGIT monoclonal antibodies and the humanized anti-human TIGIT monoclonal antibodies also bound to cynomolgus TIGIT. As shown in FIG. 6B and Table 12, the FACS study demonstrated that the chimeric anti-human TIGIT monoclonal antibodies and the humanized anti-human TIGIT monoclonal antibodies bound to cynomolgus TIGIT over-expressed in CHO-K1 cells with EC$_{50}$ values ranging from 0.9 to 2.9 nM.

TABLE 12

Anti-human TIGIT monoclonal antibodies binding on CHO-K1/cynomolgus TIGIT cells

| | Best-fit values | | |
|---|---|---|---|
| Antibody | Bottom | Top | EC$_{50}$ (nM) |
| 64G1E9B4 VH1_VL1.M1 | 3006 | 24732 | 1.65 |
| 64G1E9B4 VH1.M1_VL1.M1 | 5530 | 29184 | 0.91 |
| 100C4E7D11 VH1_VL1 | 2834 | 29839 | 2.85 |
| 64G1E9B4 chimeric | 3922 | 25591 | 1.33 |
| 100C4E7D11 chimeric | 4881 | 23687 | 1.03 |

Figure 7:
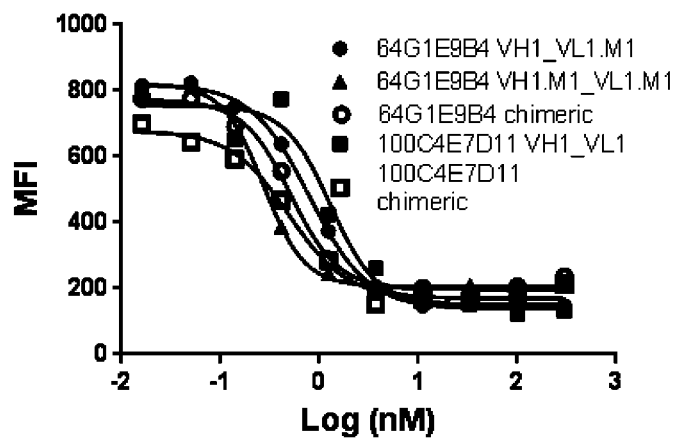
FIG. 7 depicts the competitive binding on human TIGIT between the chimeric anti-human TIGIT monoclonal antibodies or the humanized anti-human TIGIT monoclonal antibodies and PVR recombinant protein.

Example 10: The Competitive Binding on Human TIGIT Over-Expressed in CHO-K1 Cells Between the Chimeric Anti-Human TIGIT Monoclonal Antibodies or the Humanized Anti-Human TIGIT Monoclonal Antibodies and PVR Recombinant Protein The competitive binding on human TIGIT between the chimeric anti-human TIGIT monoclonal antibodies or the humanized anti-human TIGIT monoclonal antibodies and PVR recombinant protein was assessed using a FACS assay. To assess the competitive binding on human TIGIT between the chimeric anti-human TIGIT monoclonal antibodies or the humanized anti-human TIGIT monoclonal antibodies and PVR, the chimeric anti-human TIGIT monoclonal antibody or the humanized anti-human TIGIT monoclonal antibody samples were prepared (starting at 300 nM, ≤3-fold serial dilution with 10 concentrations). CHO cells expressing human TIGIT were dissociated from adherent culture flasks and mixed with varying concentrations of each chimeric anti-human TIGIT monoclonal antibody or the humanized anti-human TIGIT monoclonal antibody and 5 µg/ml human TIGIT-Fc fusion protein having a biotin label. The mixture was equilibrated for 30 minutes at room temperature and washed three times with FACS buffer (PBS containing 1% BSA). PE/Cy5 Streptavidin secondary antibody was then added to the mixtures and incubated for 15 minutes at room temperature. Subsequently, the cells were washed with FACS buffer and analyzed by flow cytometry. Data was analyzed with PRISM™ (GraphPad Software, San Diego, Calif.) using non-linear regression, and IC$_{50}$ values were calculated (FIG. 7 and Table 13). The competition FACS study demonstrated the ability of the mouse anti-human TIGIT monoclonal antibodies' capabilities on blocking to the binding between human TIGIT and human PVR with IC$_{50}$ values ranging from 0.4 nM to 1.3 nM.

TABLE 13

Anti-human TIGIT monoclonal antibodies' blocking on binding of TIGIT/PVR

| | Best-fit values | | |
|---|---|---|---|
| Antibody | Bottom | Top | IC$_{50}$ (nM) |
| 64G1E9B4 VH1_VL1.M1 | 138.6 | 819.6 | 0.79 |
| 64G1E9B4 VH1.M1_VL1.M1 | 200.6 | 508.3 | 0.35 |
| 100C4E7D11 VH1_VL1 | 150.1 | 755.4 | 1.29 |
| 64G1E9B4 chimeric | 197.1 | 771.5 | 0.51 |
| 100C4E7D11 chimeric | 170.1 | 677.7 | 0.49 |

Figure 8:
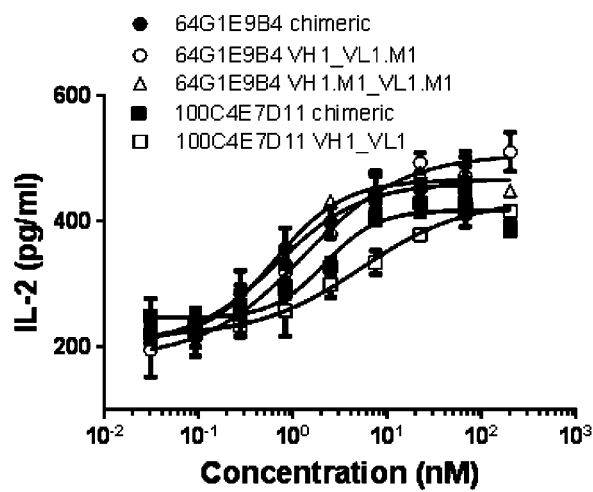
FIG. 8 depicts the neutralization effects of the chimeric anti-human TIGIT monoclonal antibodies or the humanized anti-human TIGIT monoclonal antibodies on T cell activations.

Example 11: The Neutralization Effects of the Chimeric Anti-Human TIGIT Monoclonal Antibodies and the Humanized Anti-Human TIGIT Monoclonal Antibodies on T Cell Activations Inhibited by Binding of PVR on TIGIT Overexpressed in T Cells CHO-K1 cells were engineered to be the artificial dendritic cells (APC) by stably transfecting a T cell receptor (TCR) activator. PVR was then overexpressed in the CHO-K1 APC. Human TIGIT was overexpressed in a Jurkat cell line. The CHO-K1 APC/PVR cells were co-cultured with the Jurkat/TIGIT cells to evaluate the neutralization activities of the chimeric anti-human TIGIT monoclonal antibodies and the humanized anti-human TIGIT monoclonal antibodies. The Jurkat/TIGIT cells were pre-incubated with serial dilution of each chimeric anti-human TIGIT monoclonal antibodies or each humanized anti-human TIGIT monoclonal antibodies for 30 minutes before adding the CHO-K1 APC/PVR cells. After a couple hours of interaction, 20 μl of supernatant were collected from each well for IL-2 measurement. The activation of Jurkat/TIGIT cells was evaluated by the secretion of IL-2. The binding of PVR on TIGIT between two cells inhibited Jurkat/TIGIT cells activation. The chimeric anti-human TIGIT monoclonal antibodies or the humanized anti-human TIGIT antibodies blocked the interaction between PVR and TIGIT, and then neutralized the inhibition of PVR on TIGIT. The more neutralization antibody added, the more Jurkat/TIGIT cells were activated, the more IL-2 was secreted (FIG. 8, and Table 14). Data was analyzed with PRISM™ (GraphPad Software, San Diego, Calif.) using non-linear regression, and EC$_{50}$ values were calculated on IL-2 secretion.

TABLE 14

The anti-human TIGIT antibodies on IL-2 secretion in T cell activations

| | Best-fit values | | |
|---|---|---|---|
| Antibody | Bottom | Top | EC$_{50}$ (nM) |
| 64G1E9B4 VH1_VL1.M1 | 182.1 | 507.5 | 1.27 |
| 64G1E9B4 VH1.M1_VL1.M1 | 209.4 | 466.8 | 0.63 |
| 100C4E7D11 VH1_VL1 | 217.2 | 435 | 5.21 |
| 64G1E9B4 chimeric | 204.3 | 462.3 | 0.66 |
| 100C4E7D11 chimeric | 246.6 | 418.6 | 2.14 |

Example 12: In Vivo Anti-Tumor Efficacy of Anti-TIGIT Antibodies

The mouse xenograft models were prepared by implanting MC38 tumor cells, a murine colon adenocarcinoma cell line, into C57BL/6 human TIGIT Knockin (KI) mice (Biocytogen; Worcester, Mass.). MC38 tumor cells were cultured, suspended in magnesium- and calcium-free HBSS−/−, and 1×10$^6$ cells were injected subcutaneously at the flank of female C57BL/6 human TIGIT KI mice at 6-8 weeks of age. Tumor volumes were measured using caliper and calculated with a formula (Length×Width×Width)/2. When average tumor volume reached 90-100 mm$^3$, mice were randomized to initiate treatment with the humanized anti-human TIGIT monoclonal antibodies. The humanized anti-human TIGIT monoclonal antibodies were dosed once every 4 days via i.p. (5 mg/kg). Body weight were measured throughout the study.

Figure 9A:
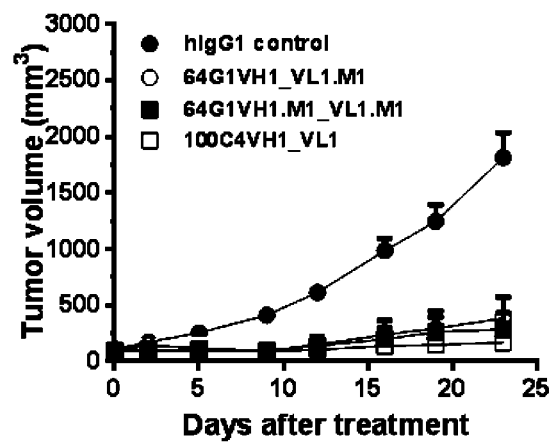
FIGS. 9A-9B show the results from an in vivo efficacy experiment of the humanized anti-human TIGIT monoclonal antibodies in MC38 syngeneic model in C57BL/6 mice with human TIGIT KI mice.
Figure 9B:
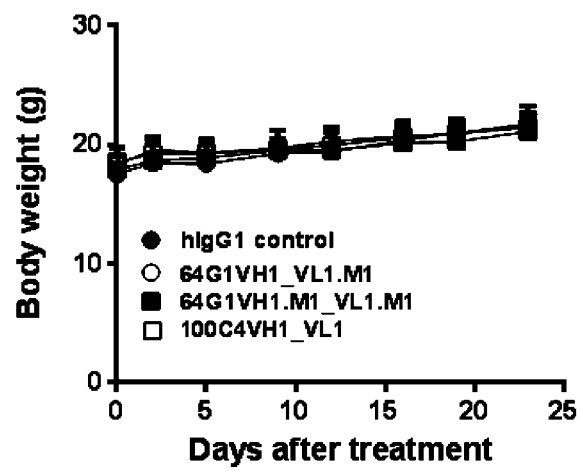

As shown in FIGS. 9A-9B, the humanized anti-human TIGIT monoclonal antibodies, 100C4E7D11VH1_VL1, 64G1E9B4VH1 VL1M1, and 64G1E9B4VH1M1_VL1M1 demonstrated the higher tumor inhibition efficacy compared to a human IgG control. The average body weight from each tested group did not demonstrate any significant difference during the days of the study.

TABLE 15

Heavy chain variable region (VH) sequences of mouse anti-TIGIT antibodies.

| mAb | ID | Sequence |
|---|---|---|
| 70A11A8E6 | 1 | DVQLQESGPGLVKPSQSLSLTCTVTGYSITSDYA WNWIRQFPGNKLEWMGYIIYSGSTSYNPSLKSRI SITRDTSKNQFFLQLNSVTTEDTATYYCARGWER RPDYWGQGTTLTVSS |
| 11D8E12A4 | 2 | EVLLQQSGPELVKPGASVKIPCKASGYTFTDYNM DWVKQSHGKSLEWIGDINPNNGGTIYNQKFKGKA TLTVDKSSSTAYMELRSLTSEDTAVYYCARRWLL LVYTMDYWGQGTSVTVSS |
| 16F10H12C11 | 3 | EVLLQQSGPELVKPGASVKIPCKASGYTFTDYNI DWVKQSHGKSLEWIGDINPNTGGTTYNQKFKGKA TLTVDKSSSTAYMELRSLTSEDTAVYYCARRWLL LVYAVDYWGQGTSVTVSS |
| 8F2D8E7 | 4 | QVQLQQSGAELVKPGASVKLSCKTSGYTFTSYWI QWIKQRPGQGLGWIGEIFPGTGTTYYNEKFKGKA TLTIDTSSSTAYMQLSSLTSEDSAVYSCARSRDG KVVDYWGQGTSVTVSS |
| 48B5G4E12 | 5 | QVQLQQPGAELVKPGASVKMSCKASGYTFTSYNM HWVKQTPGQGLEWIGGIYPGNGATSYNQKFKGKA TLTADKSSSTAYMQLSSLTSEDSAVYYCARSGLR AMDYWGQGTSVTVSS |
| 139E2C2D2 | 6 | EVQLVESGGDLVKPGGSLKLSCAASGETFSSYGM SWVRQTPDKRLEWVAIISSGGNYTYY PDSVKGRFTISRDNAKNTLYLQMSSLKSEDTAMY YCARQIHYFFAMDYWGQGTSVTVSS |
| 128E3G7F5 | 7 | EVLLQQSGPELVKTGASVKISCKASGYSFTAYYM HWVKQSHGKSLEWIGYISCYNGATTYNQKFKGKA TFTVDTSSTTAYMQENSLTSEDSAVYYCARRVYY GYDEALVYWGQGTSVTVSS |
| 121C2F10B5 | 8 | EVQLVESGGDLVKPGGSLKLSCAASGETFSTYGM SWVRQTPDKRLEWVATISSGGSYTYYPDSVKGRF TISRDNAKNTLYLQMSSLKSEDTAMYYCARQVHY FYAMDYWGQGTSVTVSS |
| 104G12E12G2 | 9 | EVQLQQSGPELVKPGASVKISCKASGYSFTGSYI HWVKQNHVKTLEWIGRINPHNGPTSYNQNFKGKA SLTVDLSSSTAYMEVHSLTSEDSAVYYCVRYDGY YGGALDYWGQGTSVTVSS |
| 83G6H11C12 | 10 | EVMLVESGGGLVKPGGSLKLSCAASGFTFSFYTM SWVRQTPEKRLEWVATISSGGGSTYYSDSVKGRF TISRDNAKNNLYLQMTSLRSEDTALYYCSRSLPV DYWGQGTTLTVSS |

TABLE 15-continued

Heavy chain variable region (VH) sequences of mouse anti-TIGIT antibodies.

| mAb | ID | Sequence |
|---|---|---|
| 92E9D4B4 | 11 | EVMLVESGGGLVKPGGSLKLSCAASGETFSFYTMSWVRQTPEKRLEWVATISGGGGDTYYPDNVKGRFTISRDNAKNNLYLQMSSLRSEDTALYYCARSLPVDFWGQGTTLTVSS |
| 100C4E7D11 | 12 | EVMLVESGGGLVKPGGSLKLSCAASGFTFSFYTMSWVRQTPEKRLEWVATISSGGGSTYYSDSVKGRFTISRDNAKNNLYLQMTSLRSEDTALYYCSRSLPVDYWGQGTTLTVSS |
| 64G1E9B4 | 13 | EVQLQQSGPELVKPGASVKISCKTSGYTFTEHVIHWVKQSHGKSLEWIGGFNPNHDGTTYNQIFRGKATLTVDKSSSTAYMELRSLTSEDSAVYFCTRAAKLLFAMDYWGQGTSVTVSS |

ID: SEQ ID NO

TABLE 16

Light chain variable region (VL) sequences of mouse anti-TIGIT antibodies

| mAb | ID | Sequence |
|---|---|---|
| 70A11A8E6 | 14 | DIVMTQSHEFMSTSLGDRVSITCKASQDVSTAVAWHQQKPGQSPKQLIYSASYRYTGVPDRFTGSGSGTDFTFTISNMQAEDLAVYYCQQHYSVPLTFGAGTKLELK |
| 11D8E12A4 | 15 | QIVLTQSPAIMSASPGEKVTISCSASSSVSYMYWYQQKPGSSPKPWIYRTSNLASGVPARFSGSGSGTSYSLTISSMEAEDAATYYCHQYHNYPPTEGGGTKLEIK |
| 16F10H12C11 | 16 | QIVLTQSPAIMSASPGEKVTISCSASSSVTYMYWYQQKAGSSPKPWIYRTSNLASGVPAREGGSGSGTSYSLTISSMEAEDAATYYCQQYHSEPPTEGGGTKLEIK |
| 8F2D8E7 | 17 | DVQMTQTTSSLSASLGDRVTISCRASQDISNFLNWYQQRPDGTVKLLIYYTSKLHSGVPSRFSGSGSGTDYSLTIRNLEKEDIATYFCQQGNTPPYTEGGGTKLEIK |
| 48B5G4E12 | 18 | QIVLTQSPAIMSASPGEKVTMTCSASSSVSYMYWYQQKTGSSPRLLIYDTSNLASGVPVRFSGSGSGTSYSLTISRMEAEDAATYYCQQWSSYPYTEGGGTKLEIK |
| 139E2C2D2 | 19 | DIQMTQSPASLSVSVGETVTITCRASENIYSNLAWYQQKQGKSPQLLVYAATNLADGAPSRFSGSRSGTQYSLKINSLQSEDEGSYYCQHFWGTAYTEGGGTKLEIK |
| 128E3G7F5 | 20 | DIVMTQSPSSLSVSAGEKVTMTCKSSQSLLNSGNQKNYLAWYQQKPGQPPKLLIYGASTRGSVPDRFTGSGSGTDFTLTISSVQAEDLAVYYCQNDHSYPYTEGGGTKLEIK |
| 121C2F10B5 | 21 | DIQMTQSPASLSVSVGETVTITCRASENIYSNLAWYQQKQGKSPQVLVYAATNLADGVPSRFSGSRSGTQYSLKINSLQSEDEGSYYCQHFWDNAYTEGGGTKLEIK |
| 104G12E12G2 | 22 | DIQMTQSPSSLSASLGERVSLTCRASQEISGYLSWLQQKPDGTIKRLIYAASTLDSGVPKRFSGSRSGSDYSLTISSLESEDFADYYCLQYASYPYTEGGGTKLEIK |
| 83G6H11C12 | 23 | QIVLTQSPAIMSASLGERVTMTCTASSSVSSSYLHWYQQKPGSSPKLWIYSTSNLASGVPARFSGSGSGTSYSLTISSMEAEDAATYYCHLYHHSPYTEGGGTKLEIK |
| 92E9D4B4 | 24 | QIVLTQSPAIMSASLGERVTMTCTASSSVSSTYLHWYQQKPGSSPKFWIYSTSNMASGVPARFSGSGSGTSYSLTISSMEAEDAATYYCHYYHRSPYTFGGGTKLEIK |
| 100C4E7D11 | 25 | QIVLTQSPAIMSASLGERVTMTCTASSSVSSTYLHWYQQKPGSSPKLWIYSTSNLASGVPARFSGSGSGTSYSLTISSMEAEDAATYYCHLYHHSPYTEGGGTKLEIK |
| 64G1E9B4 | 26 | DIVMTQSHKFMSTSIGDRVSITCKASQHVSNAVVWYQQKPGQSPKLLIYSPSYRFTGVPDRFTGSGSGTDFTFTISSVQAEDLAVYYCQQHYSTPWTFGGGTKLEIK |

ID: SEQ ID NO

TABLE 17

Heavy chain variable region (VH) CDR sequences.

| mAb | ID | CDR1 | ID | CDR2 | ID | CDR3 |
|---|---|---|---|---|---|---|
| 70A11A8E6 | 27 | GYSITSDYAWN | 40 | YIIYSGSTSYNPSLKS | 53 | GWFRRPDY |
| 11D8E12A4 | 28 | GYTFTDYNMD | 41 | DINPNNGGTIYNQKFKG | 54 | RWLLLVYTMDY |
| 16F10H12C11 | 29 | GYTFTDYNID | 42 | DINPNTGGTIYNQKFKG | 55 | RWLLLVYAVDY |
| 8F2D8E7 | 30 | GYTFTSYWIQ | 43 | EIFPGTGTTYYNEKFKG | 56 | SRDGKVVDY |
| 48B5G4E12 | 31 | GYTFTSYNMH | 44 | GIYPGNGATSYNQKFKG | 57 | SGLRAMDY |
| 139E2C2D2 | 32 | GFTFSSYGMS | 45 | IISSGGNYTYYPDSVKG | 58 | QIHYFFAMDY |
| 128E3G7F5 | 33 | GYSFTAYYMH | 46 | YISCYNGATTYNQKFKG | 59 | RVYYGYDEALVY |
| 121C2F10B5 | 34 | GFTFSTYGMS | 47 | TISSGGSYTYYPDSVKG | 60 | QVHYFYAMDY |
| 104G12E12G2 | 35 | GYSFTGSYIH | 48 | RINPHNGPTSYNQNFKG | 61 | YDGYYGGALDY |
| 83G6H11C12 | 36 | GFTFSFYTMS | 49 | TISSGGGSTYYSDSVKG | 62 | SLPVDY |

TABLE 17-continued

Heavy chain variable region (VH) CDR sequences.

| mAb | ID | CDR1 | ID | CDR2 | ID | CDR3 |
|---|---|---|---|---|---|---|
| 92E9D4B4 | 37 | GFTFSFYTMS | 50 | TISGGGGDTYYPDNVKG | 63 | SLPVDF |
| 100C4E7D11 | 38 | GFTFSFYTMS | 51 | TISSGGGSTYYSDSVKG | 64 | SLPVDY |
| 64G1E9B4 | 39 | GYTFTEHVIH | 52 | GFNPNHDGTIYNQIFRG | 65 | AAKLLFAMDY |

ID: SEQ ID NO; CDR: Complementarity Determining Region

TABLE 18

Light chain variable region (VL) CDR sequences.

| mAb | ID | CDR1 | ID | CDR2 | ID | CDR3 |
|---|---|---|---|---|---|---|
| 70A11A8E6 | 66 | KASQDVSTAVA | 79 | SASYRYT | 92 | QQHYSVPLT |
| 11D8E12A4 | 67 | SASSSVSYMY | 80 | RTSNLAS | 93 | HQYHNYPPT |
| 16F10H12C11 | 68 | SASSSVTYMY | 81 | RTSNLAS | 94 | QQYHSFPPT |
| 8F2D8E7 | 69 | RASQDISNFLN | 82 | YTSKLHS | 95 | QQGNTPPYT |
| 48B5G4E12 | 70 | SASSSVSYMY | 83 | DTSNLAS | 96 | QQWSSYPYT |
| 139E2C2D2 | 71 | RASENIYSNLA | 84 | AATNLAD | 97 | QHFWGTAYT |
| 128E3G7F5 | 72 | KSSQSLLNSGNQKNYLA | 85 | GASTRGS | 98 | QNDHSYPYT |
| 121C2F10B5 | 73 | RASENIYSNLA | 86 | AATNLAD | 99 | QHFWDNAYT |
| 104G12E12G2 | 74 | RASQEISGYLS | 87 | AASTLDS | 100 | LQYASYPYT |
| 83G6H11C12 | 75 | TASSSVSSSYLH | 88 | STSNLAS | 101 | HLYHHSPYT |
| 92E9D4B4 | 76 | TASSSVSSTYLH | 89 | STSNMAS | 102 | HYYHRSPYT |
| 100C4E7D11 | 77 | TASSSVSSTYLH | 90 | STSNLAS | 103 | HLYHHSPYT |
| 64G1E9B4 | 78 | KASQHVSNAVV | 91 | SPSYRFT | 104 | QQHYSTPWT |

ID: SEQ ID NO; CDR: Complenentarity Determining Region

TABLE 19

Humanized heavy chain variable region (VH) sequences.

| Humanized mAb | ID | Sequence |
|---|---|---|
| 100C4VH1 | 105 | EVQLVESGGGLVKPGGSLRLSCAASGFTFSFYTMSWVRQAPGKGLEWVSTISSGGGSTYYSDSVKGRFTISRDNAKNSLYLQMNSLRAEDTAVYYCARSLPVDYWGQGTTVTSS |
| 100C4VH2 | 106 | EVQLVESGGGLVKPGGSLRLSCAASGFTFSFYTMSWVRQAPGKGLEWVSTISSGGGSTYYSDSVKGRFTISRDNAKNSLYLQMNSLRAEDTAVYYCSRSLPVDYWGQGTTVTSS |
| 100C4VH3 | 107 | EVQLVESGGGLVKPGGSLRLSCAASGFTFSFYTMSWVRQAPGKGLEWVATISSGGGSTYYSDSVKGRFTISRDNAKNSLYLQMNSLRAEDTAVYYCSRSLPVDYWGQGTTVTSS |
| 100C4VH4 | 108 | EVQLVESGGGLVKPGGSLRLSCAASGFTFSFYTMSWVRQAPGKGLEWVATISSGGGSTYYSDSVKGRFTISRDNAKNSLYLQMNSLRAEDTAVYYCSRSLPVDYWGQGTTLTVSS |
| 64G1VH1 | 109 | EVQLVQSGAEVKKPGSSVKVSCKASGYTFTEHVIHWVRQAPGQGLEWMGGFNPNHDGTIYNQIFRGRVTITADKSTSTAYMELSSLRSEDTAVYYCARAAKLLFAMDYWGQGTTVTSS |
| 64G1VH2 | 110 | EVQLVQSGAEVKKPGSSVKVSCKASGYTFTEHVIHWVRQAPGQGLEWIGGFNPNHDGTIYNQIFRGRVTITADKSTSTAYMELSSLRSEDTAVYFCTRAAKLLFAMDYWGQGTTVTSS |
| 64G1VH3 | 111 | EVQLVQSGAEVKKPGSSVKVSCKASGYTFTEHVIHWVRQAPGQGLEWIGGFNPNHDGTIYNQIFRGRATLTVDKSTSTAYMELSSLRSEDTAVYFCTRAAKLLFAMDYWGQGTTVTSS |
| 64G1VH4 | 112 | EVQLVQSGAEVKKPGSSVKVSCKTSGYTFTEHVIHWVRQAPGQGLEWIGGFNPNHDGTIYNQIFRGRATLTVDKSTSTAYMELSSLRSEDTAVYFCTRAAKLLFAMDYWGQGTTVTSS |

TABLE 20

Humanized light chain variable region (VL) sequences.

| Humanized mAb | ID | Sequence |
|---|---|---|
| 100C4VL1 | 113 | EIVLTQSPGTLSLSPGERATLSCTASSSVSSTYLHWYQQKPGQAPRLLIYSTSNLASGIPDRFSGSGSGTDFTLTISRLEPEDFAVYYCHLYHHSPYTFGGGTKVEIK |
| 100C4VL2 | 114 | EIVLTQSPGTLSLSPGERATLSCTASSSVSSTYLHWYQQKPGQAPRLWIYSTSNLASGVPDRFSGSGSGTDFTLTISRLEPEDFAVYYCHLYHHSPYTFGGGTKVEIK |
| 100C4VL3 | 115 | EIVLTQSPGTLSLSPGERATLSCTASSSVSSTYLHWYQQKPGQAPRLWIYSTSNLASGVPDRFSGSGSGTDYTLTISRLEPEDFAVYYCHLYHHSPYTFGGGTKVEIK |
| 100C4VL4 | 116 | EIVLTQSPGTLSLSPGERVTMSCTASSSVSSTYLHWYQQKPGQAPRLWIYSTSNLASGVPDRFSGSGSGTDYTLTISRLEPEDFAVYYCHLYHHSPYTFGGGTKVEIK |
| 100C4VL5 | 117 | EIVLTQSPGTLSLSPGERVTMSCTASSSVSSTYLHWYQQKPGQAPRLWIYSTSNLASGVPDRFSGSGSGTDYTLTISRLEPEDAAVYYCHLYHHSPYTFGGGTKVEIK |
| 64G1VL1 | 118 | DIQMTQSPSSLSASVGDRVTITCKASQHVSNAVVWYQQKPGKAPKLLIYSPSYRFTGVPSRFSGSGSGTDFTLTISSLQPEDFATYYCQQHYSTPWTFGGGTKVEIK |

TABLE 21

Antigen Sequence

| antigen protein | ID | sequence |
|---|---|---|
| full-length human TIGIT | 122 | MRWCLLLIWAQGLRQAPLASGMMTGTIETTGNISAEKGGSIILQCHLSSTTAQVTQVNWEQQDQLLAICNADLGWHISPSFKDRVAPGPGLGLTLQSLTVNDTGEYFCIYHTYPDGTYTGRIFLEVLESSVAEHGARFQIPLLGAMAATLVVICTAVIVVVALTRKKKALRIHSVEGDLRRKSAGQEEWSPSAPSPPGSCVQAEAAPAGLCGEQRGEDCAELHDYFNVLSYRSLGNCSFFTETG |

TABLE 22

Peptide Linkers

| linker | ID | Sequence |
|---|---|---|
| G4SG3S | 119 | GGGGSGGGS |
| (G4S)3 | 120 | GGGGSGGGGSGGGGS |
| mutant hIgG1 hinge | 121 | EPKSSDKTHTSPPSP |

---

What is claimed is:

1. An isolated antibody or an antigen-binding fragment thereof, comprising:
a heavy chain variable domain (VH) comprising a heavy chain complementarity determining region 1 (HCDR1), a HCDR2, a HCDR3, and a light chain variable domain (VL) comprising a light chain complementarity determining region 1 (LCDR1), LCDR2, and LCDR3, wherein the HCDR1, HCDR2, HCDR3, LCDR1, LCDR2, and LCDR3 have the polypeptide sequences of:
(1) SEQ ID NOs: 27, 40, 53, 66, 79, and 92, respectively;
(2) SEQ ID NOs: 28, 41, 54, 67, 80, and 93, respectively;
(3) SEQ ID NOs: 29, 42, 55, 68, 81, and 94, respectively;
(4) SEQ ID NOs: 30, 43, 56, 69, 82, and 95, respectively;
(5) SEQ ID NOs: 31, 44, 57, 70, 83, and 96, respectively;
(6) SEQ ID NOs: 32, 45, 58, 71, 84, and 97, respectively;
(7) SEQ ID NOs: 33, 46, 59, 72, 85, and 98, respectively;
(8) SEQ ID NOs: 34, 47, 60, 73, 86, and 99, respectively;
(9) SEQ ID NOs: 35, 48, 61, 74, 87, and 100, respectively;
(10) SEQ ID NOs: 36, 49, 62, 75, 88, and 101, respectively;
(11) SEQ ID NOs: 37, 50, 63, 76, 89, and 102, respectively;
(12) SEQ ID NOs: 38, 51, 64, 77, 90, and 103, respectively;
(13) SEQ ID NOs: 39, 52, 65, 78, 91, and 104, respectively;

(14) SEQ ID NOs: 39, 128, 65, 131, 91, and 104, respectively; or

(15) SEQ ID NOs: 39, 52, 65, 131, 91, and 104, respectively;

wherein the antibody or antigen-binding fragment thereof is capable of specifically binding to a TIGIT.

2. The isolated antibody or antigen-binding fragment thereof of claim 1, wherein the VH comprises an amino acid sequence that is at least 90% identical to a sequence selected from the group consisting of SEQ ID NOs:1-13 and 132, and the VL comprises an amino acid sequence that is at least 90% identical to a sequence selected from the group consisting of SEQ ID NOs:14-26 and 133.

3. The isolated antibody or antigen-binding fragment thereof of claim 1, wherein:

(1) the VH comprises an amino acid sequence of SEQ ID NO:1, and the VL comprises an amino acid sequence of SEQ ID NO:14;

(2) the VH comprises an amino acid sequence of SEQ ID NO:2, and the VL comprises an amino acid sequence of SEQ ID NO:15;

(3) the VH comprises an amino acid sequence of SEQ ID NO:3, and the VL comprises an amino acid sequence of SEQ ID NO:16;

(4) the VH comprises an amino acid sequence of SEQ ID NO:4, and the VL comprises an amino acid sequence of SEQ ID NO:17;

(5) the VH comprises an amino acid sequence of SEQ ID NO:5, and the VL comprises an amino acid sequence of SEQ ID NO:18;

(6) the VH comprises an amino acid sequence of SEQ ID NO:6, and the VL comprises an amino acid sequence of SEQ ID NO:19;

(7) the VH comprises an amino acid sequence of SEQ ID NO:7, and the VL comprises an amino acid sequence of SEQ ID NO:20;

(8) the VH comprises an amino acid sequence of SEQ ID NO:8, and the VL comprises an amino acid sequence of SEQ ID NO:21;

(9) the VH comprises an amino acid sequence of SEQ ID NO:9, and the VL comprises an amino acid sequence of SEQ ID NO:22;

(10) the VH comprises an amino acid sequence of SEQ ID NO:10, and the VL comprises an amino acid sequence of SEQ ID NO:23;

(11) the VH comprises an amino acid sequence of SEQ ID NO:11, and the VL comprises an amino acid sequence of SEQ ID NO:24;

(12) the VH comprises an amino acid sequence of SEQ ID NO:12, and the VL comprises an amino acid sequence of SEQ ID NO:25;

(13) the VH comprises an amino acid sequence of SEQ ID NO:13, and the VL comprises an amino acid sequence of SEQ ID NO:26;

(14) the VH comprises an amino acid sequence of SEQ ID NO:132, and the VL comprises an amino acid sequence of SEQ ID NO:133; or

(15) the VH comprises an amino acid sequence of SEQ ID NO:13, and the VL comprises an amino acid sequence of SEQ ID NO:133.

4. The isolated antibody or antigen-binding fragment thereof of claim 1, wherein the VH is fused to a heavy chain constant region of an immunoglobulin and/or the VL is fused to a light chain constant region (CL) of an immunoglobulin.

5. The isolated antibody or antigen-binding fragment thereof of claim 1, wherein the $K_D$ of the binding between the antibody or antigen-binding fragment thereof and the TIGIT is $10^{-7}$ M to about $10^{-12}$ M.

6. The isolated antibody or antigen-binding fragment thereof of claim 1, being rodent, chimeric, human, partially humanized, or fully humanized.

7. The isolated antibody or antigen-binding fragment thereof of claim 6, wherein the VH comprises the amino acid sequence selected from the group consisting of SEQ ID NOs:105-112 and 134, and the VL comprises the amino acid sequence selected from the group consisting of SEQ ID NOs:113-118 and 135.

8. The isolated antibody or antigen-binding fragment thereof of claim 1, further comprising a second antibody moiety, wherein the second antibody moiety is capable of specifically binding to a second antigen.

9. The isolated antibody or antigen-binding fragment thereof of claim 8, wherein the second antibody moiety is a Fab, a Fab', a (Fab')$_2$, an Fv, a single chain Fv (scFv), an scFv-scFv, a minibody, a diabody, an sdAb, or an antibody mimetic.

10. The isolated antibody or antigen-binding fragment thereof of claim 8, wherein the second antibody moiety is capable of specifically binding to CTLA-4, PD-L1, TIM-3, or LAG-3, and wherein the second antibody moiety is a sdAb.

11. The isolated antibody or antigen-binding fragment thereof of claim 10, wherein the amino-terminus of the heavy chain or light chain of a full-length IgG capable of specifically recognizing TIGIT is fused to the carboxyl-terminus of the sdAb capable of specifically binding to CTLA-4, PD-L1, TIM-3, or LAG-3.

12. The isolated antibody or antigen-binding fragment thereof of claim 11, wherein the full-length IgG capable of specifically recognizing TIGIT is fused to the sdAb capable of specifically binding to CTLA-4, PD-L1, TIM-3, or LAG-3 via a peptide linker having the amino acid sequence of one of SEQ ID NOs:119-121 and 123-127.

13. A pharmaceutical composition comprising the isolated antibody or antigen-binding fragment thereof of claim 1 and a pharmaceutically acceptable carrier.

14. A method of treating a TIGIT related cancer or a pathogenic infection in a subject in need thereof, the method comprising administering to the subject in need thereof the pharmaceutical composition of claim 13.

15. The method of claim 14, wherein the pharmaceutical composition is administered to the subject in need thereof in combination with an additional cancer therapy, wherein the additional cancer therapy is a surgery, radiation, chemotherapy, immunotherapy, hormone therapy, or a combination thereof.

16. The method of claim 14, wherein the pharmaceutical composition is for systemic or local administration, and wherein the pharmaceutical composition is for intravenous or intratumoral administration.

17. The isolated antibody or antigen-binding fragment thereof of claim 10, wherein the carboxyl-terminus of the heavy chain or light chain of a full-length IgG capable of specifically recognizing TIGIT is fused to the amino-terminus of the sdAb capable of specifically binding to CTLA-4, PD-L1, TIM-3, or LAG-3.

18. The isolated antibody or antigen-binding fragment thereof of claim 1, wherein the HCDR1, HCDR2, HCDR3, LCDR1, LCDR2, and LCDR3 have the polypeptide sequences of SEQ ID NOs: 38, 51, 64, 77, 90, and 103, respectively.

19. The isolated antibody or antigen-binding fragment thereof of claim 1, wherein the HCDR1, HCDR2, HCDR3, LCDR1, LCDR2, and LCDR3 have the polypeptide sequences of SEQ ID NOs: 39, 52, 65, 78, 91, and 104, respectively.

20. The isolated antibody or antigen-binding fragment thereof of claim 1, wherein the HCDR1, HCDR2, HCDR3, LCDR1, LCDR2, and LCDR3 have the polypeptide sequences of SEQ ID NOs: 39, 128, 65, 131, 91, and 104, respectively.

21. The isolated antibody or antigen-binding fragment thereof of claim 1, wherein the HCDR1, HCDR2, HCDR3, LCDR1, LCDR2, and LCDR3 have the polypeptide sequences of SEQ ID NOs: 39, 52, 65, 131, 91, and 104, respectively.

22. The isolated antibody or antigen-binding fragment thereof of claim 7, wherein the VH comprises the amino acid sequence of SEQ ID NO: 105, and the VL comprises the amino acid sequence of SEQ ID NO: 113.

23. The isolated antibody or antigen-binding fragment thereof of claim 7, wherein the VH comprises the amino acid sequence of SEQ ID NO: 134, and the VL comprises the amino acid sequence of SEQ ID NO: 135.

* * * * *

UNITED STATES PATENT AND TRADEMARK OFFICE
CERTIFICATE OF CORRECTION

PATENT NO. : 11,708,410 B2
APPLICATION NO. : 15/733364
DATED : July 25, 2023
INVENTOR(S) : Xinpo Jiang, Shuai Yang and Chuan-Chu Chou Page 1 of 1

It is certified that error appears in the above-identified patent and that said Letters Patent is hereby corrected as shown below:

On the Title Page

Column 1 (Prior Publication Data), Line 2, Below "Apr. 1, 2021" insert -- (30) Foreign Application Priority Data Jan. 15, 2018 (CN)................... PCT/CN2018/072607 --

Signed and Sealed this
Fourteenth Day of November, 2023

Katherine Kelly Vidal
*Director of the United States Patent and Trademark Office*

SEQUENCE LISTING

```
<160> NUMBER OF SEQ ID NOS: 135

<210> SEQ ID NO 1
<211> LENGTH: 117
<212> TYPE: PRT
<213> ORGANISM: Artificial Sequence
<220> FEATURE:
<223> OTHER INFORMATION: Mouse VH

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ile Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Trp Phe Arg Arg Pro Asp Tyr Trp Gly Gln Gly Thr Thr
            100                 105                 110

Leu Thr Val Ser Ser
        115

<210> SEQ ID NO 2
<211> LENGTH: 120
<212> TYPE: PRT
<213> ORGANISM: Artificial Sequence
<220> FEATURE:
<223> OTHER INFORMATION: Mouse VH
```

```
<400> SEQUENCE: 2

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Arg Trp Leu Leu Leu Val Tyr Thr Met Asp Tyr Trp Gly Gln
            100                 105                 110

Gly Thr Ser Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Mouse VH

<400> SEQUENCE: 3

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Ile Asp Trp Val Lys Gln Ser His Gly Lys Ser Leu Glu Trp Ile
        35                  40                  45

Gly Asp Ile Asn Pro Asn Thr Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Arg Trp Leu Leu Leu Val Tyr Ala Val Asp Tyr Trp Gly Gln
            100                 105                 110

Gly Thr Ser Val Thr Val Ser Ser
        115                 120

<210> SEQ ID NO 4
<211> LENGTH: 118
<212> TYPE: PRT
<213> ORGANISM: Artificial Sequence
<220> FEATURE:
<223> OTHER INFORMATION: Mouse VH

<400> SEQUENCE: 4

Gln Val Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Thr Ser Tyr
            20                  25                  30

Trp Ile Gln Trp Ile Lys Gln Arg Pro Gly Gln Gly Leu Gly Trp Ile
        35                  40                  45
```

Gly Glu Ile Phe Pro Gly Thr Gly Thr Thr Tyr Tyr Asn Glu Lys Phe
        50                  55                  60

Lys Gly Lys Ala Thr Leu Thr Ile Asp Thr Ser Ser Thr Ala Tyr
65                  70                  75                  80

Met Gln Leu Ser Ser Leu Thr Ser Glu Asp Ser Ala Val Tyr Ser Cys
                85                  90                  95

Ala Arg Ser Arg Asp Gly Lys Val Val Asp Tyr Trp Gly Gln Gly Thr
                100                 105                 110

Ser Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: Mouse VH

<400> SEQUENCE: 5

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
                35                  40                  45

Gly Gly Ile Tyr Pro Gly Asn Gly Ala Thr Ser Tyr Asn Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Leu Arg Ala Met Asp Tyr Trp Gly Gln Gly Thr Ser
                100                 105                 110

Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: Mouse VH

<400> SEQUENCE: 6

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Trp Val
                35                  40                  45

Ala Ile Ile Ser Ser Gly Gly Asn Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Ile His Tyr Phe Phe Ala Met Asp Tyr Trp Gly Gln Gly
                100                 105                 110

```
Thr Ser Val Thr Val Ser Ser
        115

<210> SEQ ID NO 7
<211> LENGTH: 121
<212> TYPE: PRT
<213> ORGANISM: Artificial Sequence
<220> FEATURE:
<223> OTHER INFORMATION: Mouse VH

<400> SEQUENCE: 7

Glu Val Leu Leu Gln Gln Ser Gly Pro Glu Leu Val Lys Thr Gly Ala
1               5                   10                  15

Ser Val Lys Ile Ser Cys Lys Ala Ser Gly Tyr Ser Phe Thr Ala Tyr
            20                  25                  30

Tyr Met His Trp Val Lys Gln Ser His Gly Lys Ser Leu Glu Trp Ile
        35                  40                  45

Gly Tyr Ile Ser Cys Tyr Asn Gly Ala Thr Thr Tyr Asn Gln Lys Phe
    50                  55                  60

Lys Gly Lys Ala Thr Phe Thr Val Asp Thr Ser Ser Thr Thr Ala Tyr
65                  70                  75                  80

Met Gln Phe Asn Ser Leu Thr Ser Glu Asp Ser Ala Val Tyr Tyr Cys
                85                  90                  95

Ala Arg Arg Val Tyr Tyr Gly Tyr Asp Glu Ala Leu Val Tyr Trp Gly
            100                 105                 110

Gln Gly Thr Ser Val Thr Val Ser Ser
        115                 120

<210> SEQ ID NO 8
<211> LENGTH: 119
<212> TYPE: PRT
<213> ORGANISM: Artificial Sequence
<220> FEATURE:
<223> OTHER INFORMATION: Mouse VH

<400> SEQUENCE: 8

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Val His Tyr Phe Tyr Ala Met Asp Tyr Trp Gly Gln Gly
            100                 105                 110

Thr Ser Val Thr Val Ser Ser
        115

<210> SEQ ID NO 9
<211> LENGTH: 120
<212> TYPE: PRT
<213> ORGANISM: Artificial Sequence
<220> FEATURE:
<223> OTHER INFORMATION: Mouse VH
```

```
<400> SEQUENCE: 9

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Ser
            20                  25                  30

Tyr Ile His Trp Val Lys Gln Asn His Val Lys Thr Leu Glu Trp Ile
        35                  40                  45

Gly Arg Ile Asn Pro His Asn Gly Pro Thr Ser Tyr Asn Gln Asn Phe
    50                  55                  60

Lys Gly Lys Ala Ser Leu Thr Val Asp Leu Ser Ser Ser Thr Ala Tyr
65                  70                  75                  80

Met Glu Val His Ser Leu Thr Ser Glu Asp Ser Ala Val Tyr Tyr Cys
                85                  90                  95

Val Arg Tyr Asp Gly Tyr Tyr Gly Ala Leu Asp Tyr Trp Gly Gln
                100                 105                 110

Gly Thr Ser Val Thr Val Ser Ser
            115                 120

<210> SEQ ID NO 10
<211> LENGTH: 115
<212> TYPE: PRT
<213> ORGANISM: Artificial Sequence
<220> FEATURE:
<223> OTHER INFORMATION: Mouse VH

<400> SEQUENCE: 10

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Ser Thr Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Thr Ser Leu Arg Ser Glu Asp Thr Ala Leu Tyr Tyr Cys
                85                  90                  95

Ser Arg Ser Leu Pro Val Asp Tyr Trp Gly Gln Gly Thr Thr Leu Thr
                100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: Mouse VH

<400> SEQUENCE: 11

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Thr Met Ser Trp Val Arg Gln Thr Pro Glu Lys Arg Leu Glu Trp Val
        35                  40                  45
```

Ala Thr Ile Ser Gly Gly Gly Asp Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Ser Leu Pro Val Asp Phe Trp Gly Gln Gly Thr Thr Leu Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: Mouse VH

<400> SEQUENCE: 12

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Ser Thr Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Thr Ser Leu Arg Ser Glu Asp Thr Ala Leu Tyr Tyr Cys
                85                  90                  95

Ser Arg Ser Leu Pro Val Asp Tyr Trp Gly Gln Gly Thr Thr Leu Thr
            100                 105                 110

Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: Mouse VH

<400> SEQUENCE: 13

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu His
            20                  25                  30

Val Ile His Trp Val Lys Gln Ser His Gly Lys Ser Leu Glu Trp Ile
        35                  40                  45

Gly Gly Phe Asn Pro Asn His Asp Gly Thr Ile Tyr Asn Gln Ile Phe
    50                  55                  60

Arg Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg Ala Ala Lys Leu Leu Phe Ala Met Asp Tyr Trp Gly Gln Gly

Thr Ser Val Thr Val Ser Ser
                115

<210> SEQ ID NO 14
<211> LENGTH: 107
<212> TYPE: PRT
<213> ORGANISM: Artificial Sequence
<220> FEATURE:
<223> OTHER INFORMATION: Mouse VL

<400> SEQUENCE: 14

Asp Ile Val Met Thr Gln Ser His Glu Phe Met Ser Thr Ser Leu Gly
1               5                   10                  15

Asp Arg Val Ser Ile Thr Cys Lys Ala Ser Gln Asp Val Ser Thr Ala
            20                  25                  30

Val Ala Trp His Gln Gln Lys Pro Gly Gln Ser Pro Lys Gln Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Gln Gln His Tyr Ser Val Pro Leu
                85                  90                  95

Thr Phe Gly Ala Gly Thr Lys Leu Glu Leu Lys
            100                 105

<210> SEQ ID NO 15
<211> LENGTH: 106
<212> TYPE: PRT
<213> ORGANISM: Artificial Sequence
<220> FEATURE:
<223> OTHER INFORMATION: Mouse VL

<400> SEQUENCE: 15

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Tyr His Asn Tyr Pro Pro Thr
                85                  90                  95

Phe Gly Gly Gly Thr Lys Leu Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Mouse VL

<400> SEQUENCE: 16

Gln Ile Val Leu Thr Gln Ser Pro Ala Ile Met Ser Ala Ser Pro Gly
1               5                   10                  15

```
Glu Lys Val Thr Ile Ser Cys Ser Ala Ser Ser Val Thr Tyr Met
                20                  25                  30

Tyr Trp Tyr Gln Gln Lys Ala Gly Ser Ser Pro Lys Pro Trp Ile Tyr
            35                  40                  45

Arg Thr Ser Asn Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Phe Pro Pro Thr
                85                  90                  95

Phe Gly Gly Gly Thr Lys Leu Glu Ile Lys
            100                 105
```

<210> SEQ ID NO 17
<211> LENGTH: 107
<212> TYPE: PRT
<213> ORGANISM: Artificial Sequence
<220> FEATURE:
<223> OTHER INFORMATION: Mouse VL

<400> SEQUENCE: 17

```
Asp Val Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
                20                  25                  30

Leu Asn Trp Tyr Gln Gln Arg Pro Asp Gly Thr Val Lys Leu Leu Ile
            35                  40                  45

Tyr Tyr Thr Ser Lys Leu His Ser Gly Val Pro Ser Arg Phe Ser Gly
    50                  55                  60

Ser Gly Ser Gly Thr Asp Tyr Ser Leu Thr Ile Arg Asn Leu Glu Lys
65                  70                  75                  80

Glu Asp Ile Ala Thr Tyr Phe Cys Gln Gln Gly Asn Thr Pro Pro Tyr
                85                  90                  95

Thr Phe Gly Gly Gly Thr Lys Leu Glu Ile Lys
            100                 105
```

<210> SEQ ID NO 18
<211> LENGTH: 106
<212> TYPE: PRT
<213> ORGANISM: Artificial Sequence
<220> FEATURE:
<223> OTHER INFORMATION: Mouse VL

<400> SEQUENCE: 18

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Thr Gly Ser Ser Pro Arg Leu Leu Ile Tyr
            35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys
```

```
                100             105

<210> SEQ ID NO 19
<211> LENGTH: 107
<212> TYPE: PRT
<213> ORGANISM: Artificial Sequence
<220> FEATURE:
<223> OTHER INFORMATION: Mouse VL

<400> SEQUENCE: 19

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Ala Pro Ser Arg Phe Ser Gly
    50                  55                  60

Ser Arg Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Ala Tyr
                85                  90                  95

Thr Phe Gly Gly Gly Thr Lys Leu Glu Ile Lys
            100                 105

<210> SEQ ID NO 20
<211> LENGTH: 113
<212> TYPE: PRT
<213> ORGANISM: Artificial Sequence
<220> FEATURE:
<223> OTHER INFORMATION: Mouse VL

<400> SEQUENCE: 20

Asp Ile Val Met Thr Gln Ser Pro Ser Ser Leu Ser Val Ser Ala Gly
1               5                   10                  15

Glu Lys Val Thr Met Thr Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Tyr Thr Phe Gly Gly Gly Thr Lys Leu Glu Ile
            100                 105                 110

Lys

<210> SEQ ID NO 21
<211> LENGTH: 107
<212> TYPE: PRT
<213> ORGANISM: Artificial Sequence
<220> FEATURE:
<223> OTHER INFORMATION: Mouse VL

<400> SEQUENCE: 21

Asp Ile Gln Met Thr Gln Ser Pro Ala Ser Leu Ser Val Ser Val Gly
1               5                   10                  15
```

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Val Leu Val
        35                  40                  45

Tyr Ala Ala Thr Asn Leu Ala Asp Gly Val Pro Ser Arg Phe Ser Gly
    50                  55                  60

Ser Arg Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Asp Asn Ala Tyr
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Mouse VL

<400> SEQUENCE: 22

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile Lys
            100                 105

<210> SEQ ID NO 23
<211> LENGTH: 108
<212> TYPE: PRT
<213> ORGANISM: Artificial Sequence
<220> FEATURE:
<223> OTHER INFORMATION: Mouse VL

<400> SEQUENCE: 23

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Leu Tyr His His Ser Pro
                85                  90                  95

Tyr Thr Phe Gly Gly Gly Thr Lys Leu Glu Ile Lys
            100                 105

```
<210> SEQ ID NO 24
<211> LENGTH: 108
<212> TYPE: PRT
<213> ORGANISM: Artificial Sequence
<220> FEATURE:
<223> OTHER INFORMATION: Mouse VL

<400> SEQUENCE: 24

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Thr
                20                  25                  30

Tyr Leu His Trp Tyr Gln Gln Lys Pro Gly Ser Ser Pro Lys Phe Trp
            35                  40                  45

Ile Tyr Ser Thr Ser Asn Met Ala Ser Gly Val Pro Ala Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Tyr Tyr His Arg Ser Pro
                85                  90                  95

Tyr Thr Phe Gly Gly Gly Thr Lys Leu Glu Ile Lys
                100                 105

<210> SEQ ID NO 25
<211> LENGTH: 108
<212> TYPE: PRT
<213> ORGANISM: Artificial Sequence
<220> FEATURE:
<223> OTHER INFORMATION: Mouse VL

<400> SEQUENCE: 25

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Thr
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Leu Tyr His His Ser Pro
                85                  90                  95

Tyr Thr Phe Gly Gly Gly Thr Lys Leu Glu Ile Lys
                100                 105

<210> SEQ ID NO 26
<211> LENGTH: 107
<212> TYPE: PRT
<213> ORGANISM: Artificial Sequence
<220> FEATURE:
<223> OTHER INFORMATION: Mouse VL

<400> SEQUENCE: 26

Asp Ile Val Met Thr Gln Ser His Lys Phe Met Ser Thr Ser Ile Gly
1               5                   10                  15

Asp Arg Val Ser Ile Thr Cys Lys Ala Ser Gln His Val Ser Asn Ala
                20                  25                  30
```

```
Val Val Trp Tyr Gln Gln Lys Pro Gly Gln Ser Pro Lys Leu Leu Ile
            35                  40                  45
Tyr Ser Pro Ser Tyr Arg Phe Thr Gly Val Pro Asp Arg Phe Thr Gly
    50                  55                  60
Ser Gly Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Ser Thr Pro Trp
                85                  90                  95
Thr Phe Gly Gly Gly Thr Lys Leu Glu Ile Lys
                100                 105

<210> SEQ ID NO 27
<211> LENGTH: 11
<212> TYPE: PRT
<213> ORGANISM: Artificial Sequence
<220> FEATURE:
<223> OTHER INFORMATION: Mouse VH CDR1

<400> SEQUENCE: 27

Gly Tyr Ser Ile Thr Ser Asp Tyr Ala Trp Asn
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 28

Gly Tyr Thr Phe Thr Asp Tyr Asn Met Asp
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 29

Gly Tyr Thr Phe Thr Asp Tyr Asn Ile Asp
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 30

Gly Tyr Thr Phe Thr Ser Tyr Trp Ile Gln
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 31

Gly Tyr Thr Phe Thr Ser Tyr Asn Met His
1               5                   10
```

<210> SEQ ID NO 32
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 32

Gly Phe Thr Phe Ser Ser Tyr Gly Met Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 33

Gly Tyr Ser Phe Thr Ala Tyr Tyr Met His
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 34

Gly Phe Thr Phe Ser Thr Tyr Gly Met Ser
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 35

Gly Tyr Ser Phe Thr Gly Ser Tyr Ile His
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 36

Gly Phe Thr Phe Ser Phe Tyr Thr Met Ser
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 37

Gly Phe Thr Phe Ser Phe Tyr Thr Met Ser
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 38

Gly Phe Thr Phe Ser Phe Tyr Thr Met Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 39

Gly Tyr Thr Phe Thr Glu His Val Ile His
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Mouse VH CDR2

<400> SEQUENCE: 40

Tyr Ile Ile Tyr Ser Gly Ser Thr Ser Tyr Asn Pro Ser Leu Lys Ser
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 41

Asp Ile Asn Pro Asn Asn Gly Gly Thr Ile Tyr Asn Gln Lys Phe Lys
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 42

Asp Ile Asn Pro Asn Thr Gly Gly Thr Ile Tyr Asn Gln Lys Phe Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 43

```
Glu Ile Phe Pro Gly Thr Gly Thr Thr Tyr Tyr Asn Glu Lys Phe Lys
1               5                   10                  15

Gly
```

<210> SEQ ID NO 44
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 44

```
Gly Ile Tyr Pro Gly Asn Gly Ala Thr Ser Tyr Asn Gln Lys Phe Lys
1               5                   10                  15

Gly
```

<210> SEQ ID NO 45
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 45

```
Ile Ile Ser Ser Gly Gly Asn Tyr Thr Tyr Tyr Pro Asp Ser Val Lys
1               5                   10                  15

Gly
```

<210> SEQ ID NO 46
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 46

```
Tyr Ile Ser Cys Tyr Asn Gly Ala Thr Thr Tyr Asn Gln Lys Phe Lys
1               5                   10                  15

Gly
```

<210> SEQ ID NO 47
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 47

```
Thr Ile Ser Ser Gly Gly Ser Tyr Thr Tyr Tyr Pro Asp Ser Val Lys
1               5                   10                  15

Gly
```

<210> SEQ ID NO 48
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 48

```
Arg Ile Asn Pro His Asn Gly Pro Thr Ser Tyr Asn Gln Asn Phe Lys
1               5                   10                  15

Gly
```

```
<210> SEQ ID NO 49
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 49

Thr Ile Ser Ser Gly Gly Gly Ser Thr Tyr Tyr Ser Asp Ser Val Lys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 50

Thr Ile Ser Gly Gly Gly Gly Asp Thr Tyr Tyr Pro Asp Asn Val Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 51

Thr Ile Ser Ser Gly Gly Gly Ser Thr Tyr Tyr Ser Asp Ser Val Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 52

Gly Phe Asn Pro Asn His Asp Gly Thr Ile Tyr Asn Gln Ile Phe Arg
1               5                   10                  15

Gly

<210> SEQ ID NO 53
<211> LENGTH: 8
<212> TYPE: PRT
<213> ORGANISM: Artificial Sequence
<220> FEATURE:
<223> OTHER INFORMATION: Mouse VH CDR3

<400> SEQUENCE: 53

Gly Trp Phe Arg Arg Pro Asp Tyr
1               5

<210> SEQ ID NO 54
<211> LENGTH: 11
<212> TYPE: PRT
<213> ORGANISM: Artificial Sequence
```

```
<220> FEATURE:
<223> OTHER INFORMATION: Mouse VH CDR3

<400> SEQUENCE: 54

Arg Trp Leu Leu Leu Val Tyr Thr Met Asp Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Mouse VH CDR3

<400> SEQUENCE: 55

Arg Trp Leu Leu Leu Val Tyr Ala Val Asp Tyr
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Mouse VH CDR3

<400> SEQUENCE: 56

Ser Arg Asp Gly Lys Val Val Asp Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: Mouse VH CDR3

<400> SEQUENCE: 57

Ser Gly Leu Arg Ala Met Asp Tyr
1               5

<210> SEQ ID NO 58
<211> LENGTH: 10
<212> TYPE: PRT
<213> ORGANISM: Artificial Sequence
<220> FEATURE:
<223> OTHER INFORMATION: Mouse VH CDR3

<400> SEQUENCE: 58

Gln Ile His Tyr Phe Phe Ala Met Asp Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Mouse VH CDR3

<400> SEQUENCE: 59

Arg Val Tyr Tyr Gly Tyr Asp Glu Ala Leu Val Tyr
1               5                   10

<210> SEQ ID NO 60
<211> LENGTH: 10
<212> TYPE: PRT
<213> ORGANISM: Artificial Sequence
<220> FEATURE:
```

```
<223> OTHER INFORMATION: Mouse VH CDR3

<400> SEQUENCE: 60

Gln Val His Tyr Phe Tyr Ala Met Asp Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Mouse VH CDR3

<400> SEQUENCE: 61

Tyr Asp Gly Tyr Tyr Gly Gly Ala Leu Asp Tyr
1               5                   10

<210> SEQ ID NO 62
<211> LENGTH: 6
<212> TYPE: PRT
<213> ORGANISM: Artificial Sequence
<220> FEATURE:
<223> OTHER INFORMATION: Mouse VH CDR3

<400> SEQUENCE: 62

Ser Leu Pro Val Asp Tyr
1               5

<210> SEQ ID NO 63
<211> LENGTH: 6
<212> TYPE: PRT
<213> ORGANISM: Artificial Sequence
<220> FEATURE:
<223> OTHER INFORMATION: Mouse VH CDR3

<400> SEQUENCE: 63

Ser Leu Pro Val Asp Phe
1               5

<210> SEQ ID NO 64
<211> LENGTH: 6
<212> TYPE: PRT
<213> ORGANISM: Artificial Sequence
<220> FEATURE:
<223> OTHER INFORMATION: Mouse VH CDR3

<400> SEQUENCE: 64

Ser Leu Pro Val Asp Tyr
1               5

<210> SEQ ID NO 65
<211> LENGTH: 10
<212> TYPE: PRT
<213> ORGANISM: Artificial Sequence
<220> FEATURE:
<223> OTHER INFORMATION: Mouse VH CDR3

<400> SEQUENCE: 65

Ala Ala Lys Leu Leu Phe Ala Met Asp Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Mouse VL CDR1
```

```
<400> SEQUENCE: 66

Lys Ala Ser Gln Asp Val Ser Thr Ala Val Ala
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Mouse VL CDR1

<400> SEQUENCE: 67

Ser Ala Ser Ser Ser Val Ser Tyr Met Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Mouse VL CDR1

<400> SEQUENCE: 68

Ser Ala Ser Ser Ser Val Thr Tyr Met Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 69

Arg Ala Ser Gln Asp Ile Ser Asn Phe Leu Asn
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Mouse VL CDR1

<400> SEQUENCE: 70

Ser Ala Ser Ser Ser Val Ser Tyr Met Tyr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 71

Arg Ala Ser Glu Asn Ile Tyr Ser Asn Leu Ala
1               5                   10

<210> SEQ ID NO 72
<211> LENGTH: 17
<212> TYPE: PRT
<213> ORGANISM: Artificial Sequence
<220> FEATURE:
<223> OTHER INFORMATION: Mouse VL CDR1
```

-continued

<400> SEQUENCE: 72

Lys Ser Ser Gln Ser Leu Leu Asn Ser Gly Asn Gln Lys Asn Tyr Leu
1               5                   10                  15

Ala

<210> SEQ ID NO 73
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 73

Arg Ala Ser Glu Asn Ile Tyr Ser Asn Leu Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 74

Arg Ala Ser Gln Glu Ile Ser Gly Tyr Leu Ser
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Mouse VL CDR1

<400> SEQUENCE: 75

Thr Ala Ser Ser Ser Val Ser Ser Ser Tyr Leu His
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Mouse VL CDR1

<400> SEQUENCE: 76

Thr Ala Ser Ser Ser Val Ser Ser Thr Tyr Leu His
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Mouse VL CDR1

<400> SEQUENCE: 77

Thr Ala Ser Ser Ser Val Ser Ser Thr Tyr Leu His
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Mouse VL CDR1

```
<400> SEQUENCE: 78

Lys Ala Ser Gln His Val Ser Asn Ala Val Val
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 79

Ser Ala Ser Tyr Arg Tyr Thr
1               5

<210> SEQ ID NO 80
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 80

Arg Thr Ser Asn Leu Ala Ser
1               5

<210> SEQ ID NO 81
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 81

Arg Thr Ser Asn Leu Ala Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 82

Tyr Thr Ser Lys Leu His Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 83

Asp Thr Ser Asn Leu Ala Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Mouse VL CDR2
```

-continued

<400> SEQUENCE: 84

Ala Ala Thr Asn Leu Ala Asp
1               5

<210> SEQ ID NO 85
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 85

Gly Ala Ser Thr Arg Gly Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 86

Ala Ala Thr Asn Leu Ala Asp
1               5

<210> SEQ ID NO 87
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 87

Ala Ala Ser Thr Leu Asp Ser
1               5

<210> SEQ ID NO 88
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 88

Ser Thr Ser Asn Leu Ala Ser
1               5

<210> SEQ ID NO 89
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 89

Ser Thr Ser Asn Met Ala Ser
1               5

<210> SEQ ID NO 90
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 90

```
Ser Thr Ser Asn Leu Ala Ser
1               5

<210> SEQ ID NO 91
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 91

Ser Pro Ser Tyr Arg Phe Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 92

Gln Gln His Tyr Ser Val Pro Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 93

His Gln Tyr His Asn Tyr Pro Pro Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 94

Gln Gln Tyr His Ser Phe Pro Pro Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 95

Gln Gln Gly Asn Thr Pro Pro Tyr Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 96
```

Gln Gln Trp Ser Ser Tyr Pro Tyr Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 97

Gln His Phe Trp Gly Thr Ala Tyr Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 98

Gln Asn Asp His Ser Tyr Pro Tyr Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 99

Gln His Phe Trp Asp Asn Ala Tyr Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 100

Leu Gln Tyr Ala Ser Tyr Pro Tyr Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 101

His Leu Tyr His His Ser Pro Tyr Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 102

His Tyr Tyr His Arg Ser Pro Tyr Thr

```
<210> SEQ ID NO 103
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 103

His Leu Tyr His His Ser Pro Tyr Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 104

Gln Gln His Tyr Ser Thr Pro Trp Thr
1               5

<210> SEQ ID NO 105
<211> LENGTH: 115
<212> TYPE: PRT
<213> ORGANISM: Artificial Sequence
<220> FEATURE:
<223> OTHER INFORMATION: Humanized VH

<400> SEQUENCE: 105

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ser Thr Ile Ser Ser Gly Gly Gly Ser Thr Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Pro Val Asp Tyr Trp Gly Gln Gly Thr Thr Val Thr
            100                 105                 110

Val Ser Ser
        115

<210> SEQ ID NO 106
<211> LENGTH: 115
<212> TYPE: PRT
<213> ORGANISM: Artificial Sequence
<220> FEATURE:
<223> OTHER INFORMATION: Humanized VH

<400> SEQUENCE: 106

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
```

```
                35                  40                  45
Ser Thr Ile Ser Ser Gly Gly Ser Thr Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ser Arg Ser Leu Pro Val Asp Tyr Trp Gly Gln Gly Thr Thr Val Thr
                100                 105                 110

Val Ser Ser
        115

<210> SEQ ID NO 107
<211> LENGTH: 115
<212> TYPE: PRT
<213> ORGANISM: Artificial Sequence
<220> FEATURE:
<223> OTHER INFORMATION: Humanized VH

<400> SEQUENCE: 107

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Phe Tyr
                 20                  25                  30

Thr Met Ser Trp Val Arg Gln Ala Pro Gly Lys Gly Leu Glu Trp Val
                 35                  40                  45

Ala Thr Ile Ser Ser Gly Gly Gly Ser Thr Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ser Arg Ser Leu Pro Val Asp Tyr Trp Gly Gln Gly Thr Thr Val Thr
                100                 105                 110

Val Ser Ser
        115

<210> SEQ ID NO 108
<211> LENGTH: 115
<212> TYPE: PRT
<213> ORGANISM: Artificial Sequence
<220> FEATURE:
<223> OTHER INFORMATION: Humanized VH

<400> SEQUENCE: 108

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Phe Tyr
                 20                  25                  30

Thr Met Ser Trp Val Arg Gln Ala Pro Gly Lys Gly Leu Glu Trp Val
                 35                  40                  45

Ala Thr Ile Ser Ser Gly Gly Gly Ser Thr Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ser Arg Ser Leu Pro Val Asp Tyr Trp Gly Gln Gly Thr Thr Leu Thr
            100                 105                 110

Val Ser Ser
        115

<210> SEQ ID NO 109
<211> LENGTH: 119
<212> TYPE: PRT
<213> ORGANISM: Artificial Sequence
<220> FEATURE:
<223> OTHER INFORMATION: Humanized VH

<400> SEQUENCE: 109

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu His
            20                  25                  30

Val Ile His Trp Val Arg Gln Ala Pro Gly Gln Gly Leu Glu Trp Met
        35                  40                  45

Gly Gly Phe Asn Pro Asn His Asp Gly Thr Ile Tyr Asn Gln Ile Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Lys Leu Leu Phe Ala Met Asp Tyr Trp Gly Gln Gly
            100                 105                 110

Thr Thr Val Thr Val Ser Ser
        115

<210> SEQ ID NO 110
<211> LENGTH: 119
<212> TYPE: PRT
<213> ORGANISM: Artificial Sequence
<220> FEATURE:
<223> OTHER INFORMATION: Humanized VH

<400> SEQUENCE: 110

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu His
            20                  25                  30

Val Ile His Trp Val Arg Gln Ala Pro Gly Gln Gly Leu Glu Trp Ile
        35                  40                  45

Gly Gly Phe Asn Pro Asn His Asp Gly Thr Ile Tyr Asn Gln Ile Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ala Ala Lys Leu Leu Phe Ala Met Asp Tyr Trp Gly Gln Gly
            100                 105                 110

Thr Thr Val Thr Val Ser Ser
        115

<210> SEQ ID NO 111
<211> LENGTH: 119
<212> TYPE: PRT
<213> ORGANISM: Artificial Sequence

```
<220> FEATURE:
<223> OTHER INFORMATION: Humanized VH

<400> SEQUENCE: 111

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu His
                20                  25                  30

Val Ile His Trp Val Arg Gln Ala Pro Gly Gln Gly Leu Glu Trp Ile
            35                  40                  45

Gly Gly Phe Asn Pro Asn His Asp Gly Thr Ile Tyr Asn Gln Ile Phe
    50                  55                  60

Arg Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ala Ala Lys Leu Leu Phe Ala Met Asp Tyr Trp Gly Gln Gly
            100                 105                 110

Thr Thr Val Thr Val Ser Ser
        115

<210> SEQ ID NO 112
<211> LENGTH: 119
<212> TYPE: PRT
<213> ORGANISM: Artificial Sequence
<220> FEATURE:
<223> OTHER INFORMATION: Humanized VH

<400> SEQUENCE: 112

Glu Val Gln Leu Val Gln Ser Gly Ala Glu Val Lys Lys Pro Gly Ser
1               5                   10                  15

Ser Val Lys Val Ser Cys Lys Thr Ser Gly Tyr Thr Phe Thr Glu His
                20                  25                  30

Val Ile His Trp Val Arg Gln Ala Pro Gly Gln Gly Leu Glu Trp Ile
            35                  40                  45

Gly Gly Phe Asn Pro Asn His Asp Gly Thr Ile Tyr Asn Gln Ile Phe
    50                  55                  60

Arg Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ala Ala Lys Leu Leu Phe Ala Met Asp Tyr Trp Gly Gln Gly
            100                 105                 110

Thr Thr Val Thr Val Ser Ser
        115

<210> SEQ ID NO 113
<211> LENGTH: 108
<212> TYPE: PRT
<213> ORGANISM: Artificial Sequence
<220> FEATURE:
<223> OTHER INFORMATION: Humanized VL

<400> SEQUENCE: 113

Glu Ile Val Leu Thr Gln Ser Pro Gly Thr Leu Ser Leu Ser Pro Gly
1               5                   10                  15

Glu Arg Ala Thr Leu Ser Cys Thr Ala Ser Ser Ser Val Ser Ser Thr
                20                  25                  30
```

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys His Leu Tyr His His Ser Pro
                 85                  90                  95

Tyr Thr Phe Gly Gly Gly Thr Lys Val Glu Ile Lys
                100                 105

<210> SEQ ID NO 114
<211> LENGTH: 108
<212> TYPE: PRT
<213> ORGANISM: Artificial Sequence
<220> FEATURE:
<223> OTHER INFORMATION: Humanized VL

<400> SEQUENCE: 114

Glu Ile Val Leu Thr Gln Ser Pro Gly Thr Leu Ser Leu Ser Pro Gly
 1               5                  10                  15

Glu Arg Ala Thr Leu Ser Cys Thr Ala Ser Ser Val Ser Ser Thr
                20                  25                  30

Tyr Leu His Trp Tyr Gln Gln Lys Pro Gly Gln Ala Pro Arg Leu Trp
        35                  40                  45

Ile Tyr Ser Thr Ser Asn Leu Ala Ser Gly Val Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys His Leu Tyr His His Ser Pro
                 85                  90                  95

Tyr Thr Phe Gly Gly Gly Thr Lys Val Glu Ile Lys
                100                 105

<210> SEQ ID NO 115
<211> LENGTH: 108
<212> TYPE: PRT
<213> ORGANISM: Artificial Sequence
<220> FEATURE:
<223> OTHER INFORMATION: Humanized VL

<400> SEQUENCE: 115

Glu Ile Val Leu Thr Gln Ser Pro Gly Thr Leu Ser Leu Ser Pro Gly
 1               5                  10                  15

Glu Arg Ala Thr Leu Ser Cys Thr Ala Ser Ser Val Ser Ser Thr
                20                  25                  30

Tyr Leu His Trp Tyr Gln Gln Lys Pro Gly Gln Ala Pro Arg Leu Trp
        35                  40                  45

Ile Tyr Ser Thr Ser Asn Leu Ala Ser Gly Val Pro Asp Arg Phe Ser
 50                  55                  60

Gly Ser Gly Ser Gly Thr Asp Tyr Thr Leu Thr Ile Ser Arg Leu Glu
 65                  70                  75                  80

Pro Glu Asp Phe Ala Val Tyr Tyr Cys His Leu Tyr His His Ser Pro
                 85                  90                  95

Tyr Thr Phe Gly Gly Gly Thr Lys Val Glu Ile Lys
                100                 105

<210> SEQ ID NO 116

```
<211> LENGTH: 108
<212> TYPE: PRT
<213> ORGANISM: Artificial Sequence
<220> FEATURE:
<223> OTHER INFORMATION: Humanized VL

<400> SEQUENCE: 116

Glu Ile Val Leu Thr Gln Ser Pro Gly Thr Leu Ser Leu Ser Pro Gly
1               5                   10                  15

Glu Arg Val Thr Met Ser Cys Thr Ala Ser Ser Val Ser Ser Thr
            20                  25                  30

Tyr Leu His Trp Tyr Gln Gln Lys Pro Gly Gln Ala Pro Arg Leu Trp
        35                  40                  45

Ile Tyr Ser Thr Ser Asn Leu Ala Ser Gly Val Pro Asp Arg Phe Ser
50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Leu Tyr His His Ser Pro
                85                  90                  95

Tyr Thr Phe Gly Gly Gly Thr Lys Val Glu Ile Lys
            100                 105

<210> SEQ ID NO 117
<211> LENGTH: 108
<212> TYPE: PRT
<213> ORGANISM: Artificial Sequence
<220> FEATURE:
<223> OTHER INFORMATION: Humanized VL

<400> SEQUENCE: 117

Glu Ile Val Leu Thr Gln Ser Pro Gly Thr Leu Ser Leu Ser Pro Gly
1               5                   10                  15

Glu Arg Val Thr Met Ser Cys Thr Ala Ser Ser Val Ser Ser Thr
            20                  25                  30

Tyr Leu His Trp Tyr Gln Gln Lys Pro Gly Gln Ala Pro Arg Leu Trp
        35                  40                  45

Ile Tyr Ser Thr Ser Asn Leu Ala Ser Gly Val Pro Asp Arg Phe Ser
50                  55                  60

Gly Ser Gly Ser Gly Thr Asp Tyr Thr Leu Thr Ile Ser Arg Leu Glu
65                  70                  75                  80

Pro Glu Asp Ala Ala Val Tyr Tyr Cys His Leu Tyr His His Ser Pro
                85                  90                  95

Tyr Thr Phe Gly Gly Gly Thr Lys Val Glu Ile Lys
            100                 105

<210> SEQ ID NO 118
<211> LENGTH: 107
<212> TYPE: PRT
<213> ORGANISM: Artificial Sequence
<220> FEATURE:
<223> OTHER INFORMATION: Humanized VL

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Val Ser Asn Ala
            20                  25                  30

Val Val Trp Tyr Gln Gln Lys Pro Gly Lys Ala Pro Lys Leu Leu Ile
        35                  40                  45
```

```
Tyr Ser Pro Ser Tyr Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
                100                 105
```

<210> SEQ ID NO 119
<211> LENGTH: 9
<212> TYPE: PRT
<213> ORGANISM: Artificial Sequence
<220> FEATURE:
<223> OTHER INFORMATION: Peptide Linker

<400> SEQUENCE: 119

```
Gly Gly Gly Gly Ser Gly Gly Gly Ser
1               5
```

<210> SEQ ID NO 120
<211> LENGTH: 15
<212> TYPE: PRT
<213> ORGANISM: Artificial Sequence
<220> FEATURE:
<223> OTHER INFORMATION: Peptide Linker

<400> SEQUENCE: 120

```
Gly Gly Gly Gly Ser Gly Gly Gly Gly Ser Gly Gly Gly Gly Ser
1               5                   10                  15
```

<210> SEQ ID NO 121
<211> LENGTH: 15
<212> TYPE: PRT
<213> ORGANISM: Artificial Sequence
<220> FEATURE:
<223> OTHER INFORMATION: Peptide Linker

<400> SEQUENCE: 121

```
Glu Pro Lys Ser Ser Asp Lys Thr His Thr Ser Pro Pro Ser Pro
1               5                   10                  15
```

<210> SEQ ID NO 122
<211> LENGTH: 244
<212> TYPE: PRT
<213> ORGANISM: Artificial Sequence
<220> FEATURE:
<223> OTHER INFORMATION: TIGIT

<400> SEQUENCE: 122

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
                20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
        50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95
```

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 123
<211> LENGTH: 1
<212> TYPE: PRT
<213> ORGANISM: Artificial Sequence
<220> FEATURE:
<223> OTHER INFORMATION: Peptide Linker
<220> FEATURE:
<221> NAME/KEY: VARIANT
<222> LOCATION: 1
<223> OTHER INFORMATION: Can be present in repeats of any integer

<400> SEQUENCE: 123

Gly
1

<210> SEQ ID NO 124
<211> LENGTH: 2
<212> TYPE: PRT
<213> ORGANISM: Artificial Sequence
<220> FEATURE:
<223> OTHER INFORMATION: Peptide Linker
<220> FEATURE:
<221> NAME/KEY: VARIANT
<222> LOCATION: (1)..(2)
<223> OTHER INFORMATION: Can be present in repeats of any integer

<400> SEQUENCE: 124

Gly Ser
1

<210> SEQ ID NO 125
<211> LENGTH: 5
<212> TYPE: PRT
<213> ORGANISM: Artificial Sequence
<220> FEATURE:
<223> OTHER INFORMATION: Peptide Linker
<220> FEATURE:
<221> NAME/KEY: VARIANT
<222> LOCATION: (1)..(5)
<223> OTHER INFORMATION: Can be present in repeats of any integer

<400> SEQUENCE: 125

Gly Ser Gly Gly Ser
1               5

<210> SEQ ID NO 126
<211> LENGTH: 4
<212> TYPE: PRT
<213> ORGANISM: Artificial Sequence
<220> FEATURE:
<223> OTHER INFORMATION: Peptide Linker
<220> FEATURE:
<221> NAME/KEY: VARIANT
<222> LOCATION: (1)..(4)
<223> OTHER INFORMATION: Can be present in repeats of any integer

<400> SEQUENCE: 126

Gly Gly Gly Ser
1

<210> SEQ ID NO 127
<211> LENGTH: 5
<212> TYPE: PRT
<213> ORGANISM: Artificial Sequence
<220> FEATURE:
<223> OTHER INFORMATION: Peptide Linker
<220> FEATURE:
<221> NAME/KEY: VARIANT
<222> LOCATION: (1)..(5)
<223> OTHER INFORMATION: Can be present in repeats of any integer

<400> SEQUENCE: 127

Gly Gly Gly Gly Ser
1               5

<210> SEQ ID NO 128
<211> LENGTH: 17
<212> TYPE: PRT
<213> ORGANISM: Artificial Sequence
<220> FEATURE:
<223> OTHER INFORMATION: Humanized VH CDR2

<400> SEQUENCE: 128

Gly Phe Asn Pro Asn His Gly Gly Thr Ile Tyr Asn Gln Ile Phe Arg
1               5                   10                  15

Gly

<210> SEQ ID NO 129
<211> LENGTH: 10
<212> TYPE: PRT
<213> ORGANISM: Artificial Sequence
<220> FEATURE:
<223> OTHER INFORMATION: Humanized VH CDR3

<400> SEQUENCE: 129

Ala Ala Lys Leu Leu Phe Ala Phe Asp Tyr
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Humanized VH CDR3

<400> SEQUENCE: 130

Ala Ala Lys Leu Leu Phe Ala Leu Asp Tyr
1               5                   10

<210> SEQ ID NO 131
<211> LENGTH: 11

```
<212> TYPE: PRT
<213> ORGANISM: Artificial Sequence
<220> FEATURE:
<223> OTHER INFORMATION: Humanized VL CDR1

<400> SEQUENCE: 131

Arg Ala Ser Gln His Val Ser Asn Ala Val Val
1               5                   10

<210> SEQ ID NO 132
<211> LENGTH: 119
<212> TYPE: PRT
<213> ORGANISM: Artificial Sequence
<220> FEATURE:
<223> OTHER INFORMATION: Mouse VH

<400> SEQUENCE: 132

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu His
                20                  25                  30

Val Ile His Trp Val Lys Gln Ser His Gly Lys Ser Leu Glu Trp Ile
            35                  40                  45

Gly Gly Phe Asn Pro Asn His Gly Gly Thr Ile Tyr Asn Gln Ile Phe
        50                  55                  60

Arg Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg Ala Ala Lys Leu Leu Phe Ala Met Asp Tyr Trp Gly Gln Gly
                100                 105                 110

Thr Ser Val Thr Val Ser Ser
            115

<210> SEQ ID NO 133
<211> LENGTH: 107
<212> TYPE: PRT
<213> ORGANISM: Artificial Sequence
<220> FEATURE:
<223> OTHER INFORMATION: Mouse VL

<400> SEQUENCE: 133

Asp Ile Val Met Thr Gln Ser His Lys Phe Met Ser Thr Ser Ile Gly
1               5                   10                  15

Asp Arg Val Ser Ile Thr Cys Arg Ala Ser Gln His Val Ser Asn Ala
                20                  25                  30

Val Val Trp Tyr Gln Gln Lys Pro Gly Gln Ser Pro Lys Leu Leu Ile
            35                  40                  45

Tyr Ser Pro Ser Tyr Arg Phe Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
                100                 105

<210> SEQ ID NO 134
<211> LENGTH: 119
<212> TYPE: PRT
```

```
<213> ORGANISM: Artificial Sequence
<220> FEATURE:
<223> OTHER INFORMATION: Humanized VH

<400> SEQUENCE: 134

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu His
                20                  25                  30

Val Ile His Trp Val Arg Gln Ala Pro Gly Gln Gly Leu Glu Trp Met
            35                  40                  45

Gly Gly Phe Asn Pro Asn His Gly Gly Thr Ile Tyr Asn Gln Ile Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Lys Leu Leu Phe Ala Met Asp Tyr Trp Gly Gln Gly
                100                 105                 110

Thr Thr Val Thr Val Ser Ser
        115

<210> SEQ ID NO 135
<211> LENGTH: 107
<212> TYPE: PRT
<213> ORGANISM: Artificial Sequence
<220> FEATURE:
<223> OTHER INFORMATION: Humanized VL

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Val Ser Asn Ala
                20                  25                  30

Val Val Trp Tyr Gln Gln Lys Pro Gly Lys Ala Pro Lys Leu Leu Ile
            35                  40                  45

Tyr Ser Pro Ser Tyr Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
                100                 105
```